(12) United States Patent
Trah et al.

(10) Patent No.: US 6,313,344 B1
(45) Date of Patent: *Nov. 6, 2001

(54) ORGANIC COMPOUNDS

(75) Inventors: Stephan Trah, Freiburg im Breisgau (DE); Henry Szczepanski, Wallbach (CH); Ottmar Franz Hüter, Lörrach (DE); Roger Graham Hall, Pfeffingen (CH); Saleem Farooq, Arisdorf (CH); Alfons Pascual, Basel (CH)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/085,283

(22) Filed: May 27, 1998

(51) Int. Cl.[7] .................................................. C07C 327/00
(52) U.S. Cl. ........................... 564/74; 564/153; 564/163; 564/164; 564/166; 564/167; 560/35; 560/51; 560/53; 560/60; 562/444; 562/450; 544/224; 544/242; 548/247; 548/255
(58) Field of Search .............................. 564/74, 153, 163, 564/164, 166, 167; 560/35, 51, 53, 60; 562/440, 450; 544/224, 242; 548/247, 255

(56) References Cited

U.S. PATENT DOCUMENTS

| | | |
|---|---|---|
| 5,194,662 | 3/1993 | Brand et al. . |
| 5,346,902 | 9/1994 | Clough et al. ............... 514/269 |
| 5,371,084 | 12/1994 | deFraine et al. ............. 514/241 |
| 5,387,607 | 2/1995 | Brand et al. ................ 514/513 |
| 5,712,650 | 1/1998 | Barlow . |
| 5,856,560 | 1/1999 | Bayer et al. . |
| 5,874,467 | 2/1999 | Bayer et al. . |
| 5,889,059 | 3/1999 | Bayer et al. . |
| 5,985,919 | 11/1999 | Grote et al. . |
| 5,985,921 | 11/1999 | Farooq . |

FOREIGN PATENT DOCUMENTS

| | | |
|---|---|---|
| 2043733 | 12/1991 | (CA) . |
| 2182406 | 8/1995 | (CA) . |
| 195 40 361 | 5/1997 | (DE) . |
| 2233258 | 5/1997 | (CA) . |
| 370629 | 5/1990 | (EP) . |
| 414 153 | 2/1991 | (EP) . |
| 460575 | 12/1991 | (EP) . |
| 463488 | 1/1992 | (EP) . |

(List continued on next page.)

*Primary Examiner*—Samuel Barts
(74) *Attorney, Agent, or Firm*—Joseph C. Gil

(57) ABSTRACT

Compounds of formula

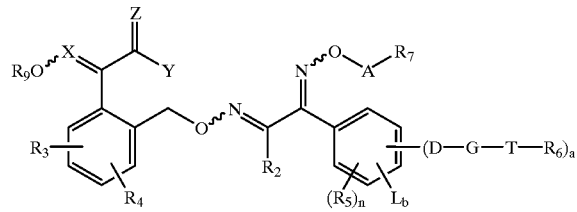

(I), wherein
either X is CH or N, Y is $OR_1$ and Z is O, or
X is N, Y is $NHR_8$ and Z is O, S or S(=O);
$R_1$, $R_2$ and $R_3$ are as defined according to the specification; m is 0, 1 or 2;
$R_5$ is, for example, halogen, $C_1$–$C_6$alkyl, halo-$C_1$–$C_6$alkyl or $C_3$–$C_6$cycloalkyl;
n is 0, 1, 2, 3 or 4; $R_9$ is methyl, fluoromethyl or difluoromethyl;
A and $R_7$ are as defined according to the specification;
D is O, S, —S(=O) or $S(=O)_2$; G is $C_1$–$C_6$aalkylene;
T—$R_6$ is $R_6$, —C(=N—O—$A_1$—$R_{77}$)—$R_6$; —$SiR_{14}$ ($R_{15}$)—$R_6$; —C(=O)—$R_6$; —C($R_{16}$)=C($R_{17}$)—$R_6$, —C≡C—$R_6$ or
—D—$R_6$;
$R_6$ is $C_1$–$C_4$alkyl or unsubstituted or substituted aryl or heteroaryl;
$A_1$ and $R_{77}$ are as defined above for A and $R_7$;
L is U—$R_{18}$, $P(OR)_vR_{11}R_{12}$, $P(S)_wR_{11}R_{12}$ or $N(aryl)R_{13}$; v and w are 0 or 1;
U—$R_{18}$ is —C(=O)—C(=O)—$R_{18}$; —C(OH)—C(OH)—$R_{18}$; —C(=N—O—$A_1$—$R_7$)—$R_{18}$;

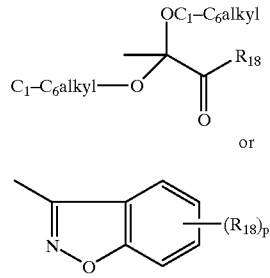

a is 0 or 1; b is 0 or 1;
$R_{11}$, $R_{12}$ and $R_{13}$ are, for example, $C_1$–$C_6$alkyl, halo-$C_1$–$C_6$alkyl or $C_3$–$C_6$cycloalkyl;
$R_{14}$ and $R_{15}$ are each independently of the other $C_1$–$C_4$alkyl;
$R_{16}$ and $R_{17}$ are each independently of the other hydrogen, $C_1$–$C_4$alkyl or halogen and $R_{18}$ is $R_5$;
and, where applicable, their possible E/Z isomers, mixtures of E/Z isomers and/or tautomers, in each case in free form or in salt form, a method of controlling pests, a process for the preparation of those compounds and their use are described.

16 Claims, No Drawings

FOREIGN PATENT DOCUMENTS

| | | |
|---|---|---|
| 472300 | 2/1992 | (EP) . |
| 506149 | 9/1992 | (EP) . |
| WO 90/07493 | 7/1990 | (WO) . |
| WO 92/13830 | 8/1992 | (WO) . |
| WO 92/18487 | 10/1992 | (WO) . |
| WO 92/18494 | 10/1992 | (WO) . |
| WO 95/18789 | 7/1995 | (WO) . |
| WO 95/21153 | 8/1995 | (WO) . |
| WO 95/21154 | 8/1995 | (WO) . |
| WO 95/21156 | 8/1995 | (WO) . |
| WO 95/34526 | 12/1995 | (WO) . |
| WO 96/11183 | 4/1996 | (WO) . |
| WO 96/16026 | 5/1996 | (WO) . |
| WO 96/35669 | 11/1996 | (WO) . |
| WO 97/20808 | 6/1997 | (WO) . |
| WO 97/20809 | 6/1997 | (WO) . |

ORGANIC COMPOUNDS

ORGANIC COMPOUNDS

The invention relates to compounds of formula

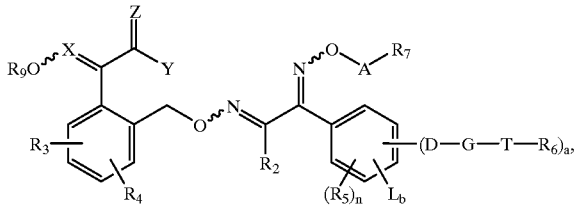

(I)

wherein either
X is CH or N, Y is OR, and Z is O, or
X is N, Y is $NHR_8$ and Z is O, S or S(=O);
$R_1$ is hydrogen or $C_1$-$C_4$alkyl;
$R_8$ is hydrogen or $C_1$-$C_4$alkyl;
$R_2$ is H, $C_1$-$C_4$alkyl, halo-$C_1$-$C_4$alkyl, $C_3$-$C_6$cycloalkyl, $C_1$-$C_4$alkoxymethyl, $C_1$-$C_4$alkoxy, halo-$C_1$-$C_4$alkoxy, $C_1$-$C_4$alkylthio, halo-$C_1$-$C_4$alkylthio or CN;
$R_3$ and $R_4$ are each independently of the other H, $C_1$-$C_4$alkyl, $C_1$-$C_4$alkoxy, OH, CN, $NO_2$, a ($C_1$-$C_4$alkyl)$_3$—Si group, the alkyl groups being the same or different, halogen, ($C_1$-$C_4$alkyl)S(=O)$_m$, (halo-$C_1$-$C_4$alkyl)S(=O)$_m$, halo-$C_1$-$C_4$alkyl or halo-$C_1$-$C_4$alkoxy;
m is 0, 1 or 2;
$R_5$ independently of any other is halogen, $C_1$-$C_6$alkyl, halo-$C_1$-$C_6$alkyl, $C_3$-$C_6$cycloalkyl, halo-$C_3$-$C_6$cycloalkyl, $C_1$-$C_6$alkoxy, halo-$C_1$-$C_6$alkoxy, $C_1$-$C_6$alkylthio, halo-$C_1$-$C_6$alkylthio, $C_1$-$C_6$alkylsulfinyl, halo-$C_1$-$C_6$alkylsulfinyl, $C_1$-$C_6$alkylsulfonyl, halo-$C_1$-$C_6$alkylsulfonyl, $C_1$-$C_6$alkylsulfonyloxy, halo-$C_1$-$C_6$alkylsulfonyloxy, $C_1$-$C_6$alkoxy-$C_1$-$C_6$alkyl, halo-$C_1$-$C_6$alkoxy-$C_1$-$C_6$alkyl, $C_1$-$C_6$alkylthio-$C_1$-$C_6$alkyl, halo-$C_1$-$C_6$alkylthio-$C_1$-$C_6$alkyl, $C_1$-$C_6$alkylsulfinyl-$C_1$-$C_6$alkyl, halo-$C_1$-$C_6$alkylsulfinyl-$C_1$-$C_6$alkyl, $C_1$-$C_6$alkylsulfonyl-$C_1$-$C_6$alkyl, halo-$C_1$-$C_6$alkylsulfonyl-$C_1$-$C_6$alkyl, $C_1$-$C_6$alkylcarbonyl, halo-$C_1$-$C_6$alkylcarbonyl, $C_1$-$C_6$-alkoxycarbonyl, halo-$C_1$-$C_6$alkoxycarbonyl, $C_1$-$C_6$alkylaminocarbonyl, $C_1$-$C_4$alkoxyiminomethyl, di($C_1$-$C_6$alkyl)aminocarbonyl, the alkyl groups being the same or different; $C_1$-$C_6$alkylaminothiocarbonyl, di($C_1$-$C_6$alyl)aminothiocarbonyl, the alkyl groups being the same or different; $C_1$-$C_6$alkylamino, di($C_1$-$C_6$alkyl)amino, the alkyl groups being the same or different; $NO_2$, CN, $SF_5$, thioamido, thiocyanatomethyl, trimethylsilyl; $C_1$-$C_4$alkylenedioxy or —CH=CH—CH=CH— each of which is unsubstituted or, depending on its substitution possibilities, mono- to tetra-substituted, the substituents of the $C_1$-$C_4$alkylenedioxy or —CH=CH—CH=CH— group being selected from the group consisting of $C_1$-$C_4$alkyl and halogen; a heterocyclyl, aryl-Q-$C_1$-$C_6$alkyl, aryl-Q—$C_2$-$C_6$alkenyl, heterocyclyl-Q—$C_1$-$C_6$alkyl or heterocyclyl-Q—$C_2$-$C_6$-alkenyl, or aryl-Q—, heterocycylyl-Q—, aryl-Q—$C_1$-$C_6$alkyl, aryl-Q—$C_2$-$C_6$alkenyl, heterocyclyl-Q—$C_1$-$C_6$-alkyl or heterocyclyl-Q—$C_2$-$C_6$alkenyl each of which is, depending on its substitution possibilities, mono- to penta-substituted in the aryl or heterocyclyl ring, the substituents being selected independently of one another from the group consisting of halogen, $C_1$-$C_6$alkyl, halo-$C_1$-$C_6$alkyl, $C_3$-$C_6$cycloalkyl, halo-$C_3$-$C_6$cycloalkyl, $C_1$-$C_6$alkoxy, halo-$C_1$-$C_6$alkoxy, CN, nitro and $C_1$-$C_6$alkoxycarbonyl; and, when n is greater than 1, the radicals $R_5$ are the same or different;
n is 0, 1, 2, 3 or, if either a or b is 0, 4;
Q is a direct bond, —CH(OH)—, —C(=O), —S—, —S(=O) or —S(=O)$_2$;
$R_9$ is methyl, fluoromethyl or difluoromethyl; either
A is a direct bond, $C_1$-$C_{10}$alkylene, —C(=O)—, —C(=S)— or halo-$C_1$-$C_{10}$alkylene and
$R_7$ is a radical $R_{10}$; or
A is $C_1$-$C_{10}$alkylene, —C(=O)—, —C(=S) or halo-$C_1$-$C_{10}$alkylene and
$R_7$ is —CN, $OR_{10}$, $N(R_{10})_2$, the radicals $R_{10}$ being the same or different, —$SR_{10}$, —S(=O)$R_{10}$ or —S(=O)$_2R_{10}$
$R_{10}$ is H, $C_1$-$C_6$alkyl, $C_2$-$C_6$alkenyl, $C_2$-$C_6$alkynyl or $C_3$-$C_6$cycloalkyl, or $C_1$-$C_6$alkyl, $C_2$-$C_8$-alkenyl, $C_2$-$C_8$alkynyl or $C_3$-$C_6$cycloalkyl each mono- or poly-substituted by substituents from the group consisting of halogen; —Si($C_1$-$C_4$alkyl)$_3$, the alkyl groups being the same or different; $C_1$-$C_6$alkoxycarbonyl or an aryl or heterocyclyl group that is unsubstituted or mono- or poly-substituted by substituents selected from the group consisting of halogen, $C_1$-$C_4$alkyl and halo-$C_1$-$C_4$alkyl; and
D is O, S, —S(=O) or S(=O)$_2$;
G is $C_1$-$C_8$alkylene;
T—$R_6$ is $R_6$; —C(=N—O—$A_1$—$R_{77}$)—$R_6$; —$SiR_{14}$($R_{15}$)—$R_6$; —C(=O)—$R_6$; C($R_{16}$)=C($R_{17}$)—$R_6$; —C≡C—$R_6$ or —D—$R_6$;
$R_6$ is $C_1$-$C_4$alkyl, aryl or heteroaryl; or aryl or heteroaryl each of which—depending on the substitution possibilities on the ring structure—is mono- to penta-substituted by substituents selected independently of one another from the group consisting of ($R_5$)$_s$; is, depending on the substitution possibilities on the ring, 0, 1, 2, 3, 4 or 5, the substituents $R_5$ being independent of one another when s is greater than 1;
$A_1$ and $R_{77}$ are as defined above for A and $R_7$;
a is 0 or 1;
L is U—$R_{18}$, P(O)$_v R_{11}R_{12}$, P(S)$_w R_{11}R_{12}$ or N(aryl)$R_{13}$, the aryl radical being either unsubstituted or mono- to penta-substituted by substituents selected independently of one another from the group consisting of $R_5$;
v and w are 0 or 1;
U—$R_{18}$ is —C(=O)—C(=O)—$R_{18}$; —C(OH)—C(OH)—$R_{18}$; —C(=N—O—$A_1$—$R_7$)—$R_{18}$;

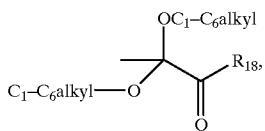

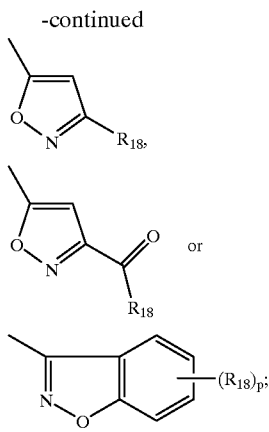

p is from 0 to 4;

$R_{11}$ and $R_{12}$ are each independently of the other $C_1$–$C_6$alkyl, halo-$C_1$–$C_6$alkyl, $C_3$–$C_6$cycloalkyl, halo-$C_3$–$C_6$cycloalkyl, $C_1$–$C_6$alkoxy, halo$_1$–$C_6$alkoxy, $C_1$–$C_6$alkylthio, halo-$C_1$–$C_6$alkylthio, aryl, heteroaryl, aryloxy, arylthio, heteroaryloxy or heteroarylthio; or aryl, heteroaryl, aryloxy, arylthio, heteroaryloxy or heteroarylthio each mono- to penta-substituted by $R_5$, the substituents $R_5$ being independent of one another;

b is 0 or 1, but a and b are not simultaneously 0;

$R_{13}$ is hydrogen, $C_1$–$C_6$alkyl, halo-$C_1$–$C_6$alkyl, $C_3$–$C_6$cycloalkyl, halo-$C_3$—$C_6$-cycloalkyl, $C_1$–$C_6$alkylsulfinyl, halo-$C_1$–$C_6$alkylsulfinyl, $C_1$–$C_6$alkylsulfonyl, halo-$C_1$–$C_6$alkylsulfonyl, $C_1$–$C_6$alkoxy-$C_1$–$C_6$alkyl, halo-$C_1$–$C_6$alkoxy-$C_1$–$C_6$alkyl, $C_1$–$C_6$alkylthio-$C_1$–$C_6$alkyl, halo-$C_1$–$C_6$alkylthio-$C_1$–$C_6$alky, $C_1$–$C_6$alkylsulfinyl-$C_1$–$C_6$alkyl, halo-$C_1$–$C_6$alkylsulfinyl-$C_1$–$C_6$alkyl, $C_1$–$C_6$alkylsulfonyl-$C_1$–$C_6$alkyl, halo-$C_1$–$C_6$alkylsulfonyl-$C_1$–$C_6$alkyl, formyl, $C_1$–$C_6$alkylcarbonyl, $C_1$–$C_6$alkyl-C(=S)—, $C_1$–$C_6$alkylthio-C(=S)—, halo-$C_1$–$C_6$alkylcarbonyl, $C_1$–$C_6$alkoxycarbonyl, halo-$C_1$–$C_6$alkoxycarbonyl, $C_1$–$C_6$alkylaminocarbonyl, $C_1$–$C_4$-alkoxyiminomethyl, di($C_1$–$C_6$alkyl)aminocarbonyl, the alkyl groups being the same or different; $C_1$–$C_6$alkylaminothiocarbonyl, di($C_1$–$C_6$alkyl) aminothiocarbonyl, the alkyl groups being the same or different; $C_1$–$C_6$alkyldicarbonyl, halo-$C_1$–$C_6$alkyldicarbonyl, $C_1$–$C_6$alkoxydicarbonyl, halo-$C_1$–$C_6$alkoxydicarbonyl, $C_1$–$C_6$alkylaminodicarbonyl, di($C_1$–$C_6$alkyl)aminodicarbonyl, the alkyl groups being the same or different; $C_1$–$C_6$alkylaminodithiocarbonyl, di($C_1$–$C_6$alkyl) aminodithiocarbonyl, the alkyl groups being the same or different; aryl, arylsulfinyl, aryl-$C_1$–$C_6$alkylsulfinyl, arylsulfonyl, aryl-$C_1$–$C_6$alkyl-sufonyl, aryloxy-$C_1$–$C_6$alkyl, arylthio-$C_1$–$C_6$alkyl, aryl-$C_1$–$C_6$alkylsulfinyl-$C_1$–$C_6$alkyl, aryl-$C_1$–$C_6$alkylsulfonyl-$C_1$–$C_6$alkyl, arylcarbonyl, arylalkylcarbonyl, aryloxycarbonyl, arylalkoxycarbonyl, arylaminocarbonyl, aryloxyiminomethyl, di(aryl)aminocarbonyl, the aryl groups being the same or different; arylaminothiocarbonyl, di(aryl)aminothiocarbonyl, the aryl groups being the same or different; aryldicarbonyl, aryl-$C_1$–$C_6$alkyldicarbonyl, aryloxydicarbonyl, aryl-$C_1$–$C_6$alkoxydicarbonyl, arylaminodicarbonyl, di(aryl) aminodicarbonyl, the aryl groups being the same or different; arylaminodithiocarbonyl, di(arylaminodithiocarbonyl, the aryl groups being the same or different; and the aryl groups in the aforementioned substituents being unsubstituted or mono- to penta-substituted by substituents $R_5$, the substituents $R_5$ being independent of one another; unsubstituted or substituted heteroaryl, unsubstituted or substituted heteroarylcarbonyl, unsubstituted or substituted heteroarylsulfinyl, or unsubstituted or substituted heteroarylsulfonyl;

$R_{14}$ and $R_{15}$ are each independently of the other $C_1$–$C_4$alkyl;

$R_{16}$ and $R_{17}$ are each independently of the other hydrogen, $C_1$–$C_4$alkyl or halogen and $R_{18}$ is $R_6$;

and, where applicable, their possible E/Z isomers, mixtures of E/Z isomers and/or tautomers, in each case in free form or in salt form, with the proviso (P1) that G is not —$CH_2$— when $R_2$ is methyl, $R_3$ and $R_4$ are hydrogen, D is oxygen, a is 1, b is 0, and either in the group —$SiR_{14}(R_{14}(R_{15})$—$R_6$ the radicals $R_{14}$, $R_{15}$ and $R_6$ are methyl, or in the group —$C(R_{16})$=C ($R_{17}$)—$R_6$ the radical $R_6$ is methyl and the radical $R_{17}$ is hydrogen or methyl;

with the proviso (P2) that G is not $C_1C_3$alkylene when a is 1, b is 0, T is a direct bond and $R_6$ is $C_1$–$C_4$alkyl;

and with the further proviso (P3) that G is not —$CH_2$— when D is oxygen, a is 1, b is 0, $R_2$ is $C_1$–$C_6$alkyl or $C_3$–$C_6$cycloalkyl, T is a direct bond and $R_6$ is unsubstituted or substituted phenyl;

to pesticidal compositions, the active ingredient of which is selected from those compounds, E/Z isomers and tautomers, in each case in free form or in salt form; to a process for the preparation of those compositions and to the use thereof; to intermediates and, where applicable, their possible E/Z isomers, mixtures of E/Z isomers and/or tautomers, in free form or in salt form, for the preparation of those compounds, where applicable tautomers, in free form or in salt form, of those intermediates; and to a process for the preparation of those intermediates and their tautomers and to the use thereof.

In the literature a number of methoxyacrylic acid derivatives are proposed as active ingredients in pesticides. The biological properties of those known compounds are not, however, entirely satisfactory in the field of pest control and there is therefore a need to provide further compounds having pesticidal properties, especially for controlling insects and representatives of the order Acarina and especially for controlling phytopathogenic microorganisms. That problem is solved according to the invention by the provision of the present compounds of formula (I).

A number of compounds of formula (I), and of the formulae (III), (IV), (VI), (VIII), (IX), (XII), (XIII), (XV), (XVIII), (XXII), (XXIII) and (XXIV) given hereinafter, contain asymmetrical carbon atoms, as a result of which the compounds may occur in optically active form. By virtue of the presence of the C=X and oximino double bonds, the compounds may occur in the E and Z isomeric forms. Atropisomers of the compounds may also occur. The corresponding formulae are intended to include all those possible isomeric forms and also mixtures thereof, for example racemates or mixtures of E/Z isomers, and also, where applicable, salts thereof, even if this is not specifically mentioned every time.

Unless indicated to the contrary, the general terms used hereinbefore and hereinafter have the following meanings.

Unless indicated to the contrary, carbon-containing groups and compounds each contain from 1 up to and including 8, especially from 1 up to and including 6, more especially from 1 up to and including 4, very especially 1 or 2, carbon atoms.

Alkyl, as a group per se and also as a structural unit of other groups and compounds, such as of haloalkyl, alkoxy, alkylthio, alkylsulfinyl, alkylsulfonyl, alkylcarbonyl, alkoxycarbonyl, alkylamino, alkoxyiminomethyl, alkylaminocarbonyl and alkylaminothiocarbonyl, is, in each individual case giving due consideration to the number of carbon atoms contained in the group or compound in question, either straight-chain, that is to say methyl, ethyl, propyl, butyl, pentyl or hexyl, or branched, e.g. isopropyl, isobutyl, sec-butyl, tert-butyl, isopentyl, neopentyl or isohexyl.

Alkenyl, as a group per se and also as a structural unit of other groups and compounds, such as of haloalkenyl, is, in each individual case giving due consideration to the number of carbon atoms contained in the group or compound in question, either straight-chain, for example vinyl, 1-methylvinyl, allyl, 1-butenyl or 2-hexenyl, or branched, for example isopropenyl.

Alkynyl, as a group per se and also as a structural unit of other groups and compounds, such as of haloalkynyl, is, in each individual case giving due consideration to the number of carbon atoms contained in the group or compound in question, either straight-chain, for example propargyl, 2-butynyl or 5-hexynyl, or branched, for example 2-ethynylpropyl or 2-propargylisopropyl.

$C_3$–$C_6$Cycloalkyl is cyclopropyl, cyclobutyl, cyclopentyl or cyclohexyl.

Alkylene, as a group per se and also as a structural unit of other groups and compounds, such as of haloalkylene, is, in each individual case giving due consideration to the number of carbon atoms contained in the group or compound in question, either straight-chain, for example —$CH_2CH_2$—, —$CH_2CH_2CH_2$— or —$CH_2CH_2CH_2CH_2$—, or branched, for example —$CH(CH_3)$—, —$CH(C_2H_5)$—, —$C(CH_3)_2$—, —$CH(CH_3)CH_2$— or —$CH(CH_3)CH(CH_3)$—. Preference is given to —$CH_2CH_2$—, —$CH(CH_3)$—, —$CH(C_2H_5)$—, and —$CH_2CH_2CH_2$—.

Aryl is phenyl or naphthyl, especially phenyl.

Heterocyclyl is a 5- to 7-membered aromatic or nonaromatic ring having from one to three hetero atoms selected from the group consisting of N, O and S. Preference is given to aromatic 5- and 6-membered rings having a nitrogen atom as hetero atom and optionally a further hetero atom, preferably nitrogen or sulfur, especially nitrogen. Preferred heteroaryl moieties are pyrazinyl, 3'-pyridyl, 2'-pyridyl, 4-pyridyl, 2'-pyrimidinyl, 4'-pyrimidinyl, 5'-pyrimidinyl, 2'-thiazolyl, 2'-oxazolyl, 2'-thienyl, 3'-thienyl and 2'-thiazolyl.

Halogen, as a group per se and also as a structural unit of other groups and compounds, such as of haloalkyl, haloalkenyl and haloalkynyl, is fluorine, chlorine, bromine or iodine, especially fluorine, chlorine or bromine, more especially fluorine or chlorine, very especially fluorine. Halo-substituted carbon-containing groups and compounds, such as haloalkyl, haloalkenyl or haloalkynyl, may be partially halogenated or per-halogenated, it being possible in the case of poly-halogenation for the halogen substituents to be the same or different. Examples of haloalkyl, as a group per se and also as a structural unit of other groups and compounds, such as of haloalkenyl, are methyl that is mono- to tri-substituted by fluorine, chlorine and/or by bromine, such as $CHF_2$ or $CF_3$; ethyl that is mono- to penta-substituted by fluorine, chlorine and/or by bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl that is mono- to hepta-substituted by fluorine, chlorine and/or by bromine, such as $CH_2CHBrCH_2Br$, $CF_2CHFCF_3$, $CH_2CF_2CF_3$ or $CH(CF_3)_2$; and butyl, or an isomer thereof, that is mono- to hepta-substituted by fluorine, chlorine and/or by bromine, such as $CF(CF_3)CHFCF_3$ or $CH_2(CF_2)_2CF_3$. Haloalkenyl is, for example, $CH_2CH=CHCl$, $CH_2CH=CCl_2$, $CH_2CF=CF_2$ or $CH_2CH=CHCH_2Br$. Haloalkynyl is, for example, $CH_2C\equiv CF$, $CH_2C\equiv CCH_2Cl$ or $CF_2CF_2C\equiv CCH_2F$.

A number of compounds of formula (I), and of the formulae (III) to (XXIV) given hereinafter, may, as is known to the person skilled in the art, be present in the form of tautomers, especially when $R_7$ is H. Hereinbefore and hereinafter any reference to these compounds should therefore be understood as including also corresponding tautomers, even when the latter are not specifically mentioned in each case.

Compounds of formula (I), and of the formulae (III) to (XXIV) given hereinafter, that have at least one basic centre may, for example, form acid addition salts. Such salts are formed, for example, with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted or substituted, for example halo-substituted, $C_1$–$C_4$alkanecarboxylic acids, e.g. acetic acid, saturated or unsaturated dicarboxylic acids, e.g. oxalic acid, malonic acid, succinic acid, maleic acid, fumaric acid or phthalic acid, hydroxycarboxylic acids, e.g. ascorbic acid, lactic acid, malic acid, tartaric acid or citric acid, or benzoic acid, or with organic sulfonic acids, such as unsubstituted or substituted, for example halo-substituted, $C_1$–$C_4$alkane- or arylsulfonic acids, e.g. methane- or p-toluene-sulfonic acid. Furthermore, compounds of formula (I) having at least one acid group may form salts with bases. Suitable salts with bases are, for example, metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl or dimethyl-propyl-amine, or a mono-, di- or tri-hydroxy-lower alkylamine, e.g. mono-, di- or tri-ethanolamine. It may also be possible for corresponding internal salts to be formed. Within the context of the invention, preference is given to agrochemically advantageous salts; also included, however, are salts which cannot be agrochemically used, which are used however, for example, for isolating and/or purifying free compounds of formula (I) or agrochemically acceptable salts thereof. Hereinbefore and hereinafter any reference to the compounds of formula (I) in free form is to be understood as including also the salts of compounds of formula (I), and any reference to the salts is to be understood as including also the corresponding free compounds of formula (I), as appropriate and expedient. The same applies also to tautomers of compounds of formulae (I) and (III) to (XXIV) and salts thereof. In each case the free form is generally preferred.

Preferred embodiments within the context of the invention, in each case taking into consideration the provisos mentioned hereinbefore, are:

(1) a compound of formula (I) wherein X is CH and Z is O; especially wherein X is CH, Z is O and Y is —$OCH_3$;

(2) a compound of formula (I) wherein X is N and Z is O; especially wherein X is N, Z is O and Y is $NHCH_3$;

(3) a compound of formula (I) wherein Y is $OC_1$–$C_4$alkyl, preferably $C_1$—$C_2$alkoxy, especially methoxy;

(4) a compound of formula (I) wherein
R$_2$ is H, C$_1$–C$_4$alkyl, halo-C$_1$–C$_4$alkyl or C$_3$–C$_6$cycloalkyl, preferably C$_1$–C$_4$alkyl or halo-C$_1$–C$_4$alkyl, especially C$_1$–C$_2$alkyl, more especially methyl;

(5) a compound of formula (I) wherein
R$_3$ is H, C$_1$–C$_4$alkyl, C$_1$–C$_4$alkoxy, OH, CN, NO$_2$, halogen, halo-C$_1$–C$_4$alkyl or halo-C$_1$–C$_4$alkoxy, preferably H, C$_1$–C$_4$alkyl, C$_1$–C$_4$alkoxy or halogen, especially H, methyl, methoxy, chlorine or fluorine, more especially H;

(6) a compound of formula (I) wherein
R$_4$ is H, C$_1$–C$_4$alkyl, C$_1$–C$_4$alkoxy, OH, CN, NO$_2$, halogen, halo-C$_1$–C$_4$alkyl or halo-C$_1$–C$_4$alkoxy, preferably H, C$_1$–C$_4$alkyl, C$_1$–C$_4$alkoxy or halogen, especially H, methyl, methoxy, chlorine or fluorine, more especially H;

(7) a compound of formula (I) wherein
R$_8$ is H or C$_1$–C$_2$alkyl, preferably C$_1$–C$_2$alkyl, especially methyl;

(8) a compound of formula (I) wherein R$_9$ is methyl or fluoromethyl, preferably methyl;

(9) a compound of formula (I) wherein
A is a direct bond, C$_1$–C$_{10}$alkylene or halo-C$_1$–C$_{10}$alkylene, preferably a direct bond or C$_1$–C$_4$alkylene, especially a direct bond or methylene, and R$_7$ is a radical R$_{10}$;

(10) a compound of formula (I) wherein AR$_7$ is methyl or ethyl, especially ethyl;

(11) a compound of formula (I) wherein n is 0;

(12) a compound of formula (I) wherein a is 0, b is 1 and L is —C(=O)—C(=O)—R$_{18}$, —C(=NO—A$_1$—R$_{77}$)—R$_{18}$,

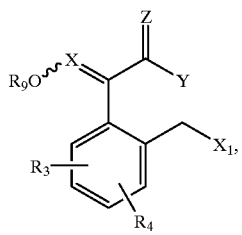

(13) a compound of formula (I) wherein R$_{18}$ is unsubstituted or substituted phenyl;

(14) a compound of formula (I) wherein a is 0, n is 0, b is 1 and L is POR$_{11}$R$_{12}$;

(15) a compound of formula (I) wherein R$_1$, and R$_{12}$ are each independently of the other C$_1$–C$_6$alkoxy, halo-C$_1$–C$_6$alkoxy, C$_1$–C$_6$alkylthio, halo-C$_1$–C$_6$alkylthio, aryl, aryloxy or arylthio;
or aryl, heteroaryl, aryloxy, arylthio, heteroaryloxy or heteroarylthio each mono- to tri-substituted by R$_5$, the substituents R$_5$ being independent of one another;

(16) a compound of formula (I) wherein a is 0, n is 0, b is 1, L is N(aryl)R$_{13}$ and R$_{13}$ is H, methyl, ethyl or formyl, especially H;

(17) a compound of formula (I) wherein a is 1, n is 0, b is 0 and D is oxygen;

(18) a compound of formula (I) wherein a is 1 and G is C$_1$–C$_4$alkylene, especially —CH$_2$—CH$_2$— or —CH(CH$_3$)—;

(19) a compound of formula (I) wherein a is 1, b is 0 and T is a direct bond, —C(=N—O—A$_1$—R$_7$)—, —SiR$_{14}$(R$_{15}$)— or —C , especially —SiR$_{14}$(R$_{15}$)—;

(20) a compound of formula (I) wherein R$_6$ is C$_1$–C$_4$alkyl, aryl, or aryl mono- to penta-substituted by substituents selected independently of one another from the group consisting of R$_5$;

R$_6$ being especially phenyl that is unsubstituted or mono- or di-substituted, especially mono-substituted, by halogen, C$_1$–C$_4$alkyl, halo-C$_1$–C$_4$alkyl or by halo-C$_1$–C$_4$alkoxy, especially mono-substituted by fluorine, chlorine, C$_1$–C$_4$alkyl, trifluoromethyl or by trifluoromethoxy.

Special preference is given to the compounds of Tables 1 to 15.

The invention relates also to a process for the preparation of the compounds of formula (I) and, where applicable, their E/Z isomers, mixtures of E/Z isomers and/or tautomers, in each case in free form or in salt form, which process comprises, for example, either a1) reacting a compound of formula

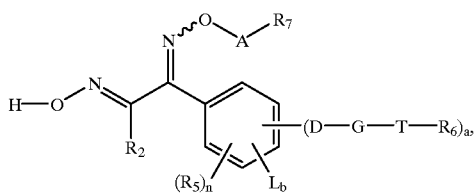

(II)

which is known or can be prepared in accordance with methods known per se and wherein X, Y, Z, R$_3$, R$_4$ and R$_9$ are as defined for formula (I) and X$_1$ is a leaving group, preferably in the presence of a base, With a compound of formula (III)

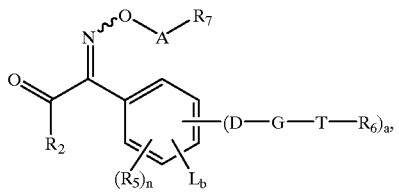

wherein a, b, n, A, D, G, T, L, R$_2$, R$_5$, R$_6$ and R$_7$ are as defined for formula (I) and wherein the provisos mentioned above for the compounds of formula (I) apply, or a2) reacting a compound of formula (IV)

wherein a, b, n, A, D, G, T, L, R$_2$, R$_5$, R$_6$ and R$_7$ are as defined for formula (I) and wherein the provisos mentioned above for the compounds of formula (I) apply, optionally in the presence of a base, with a compound of formula

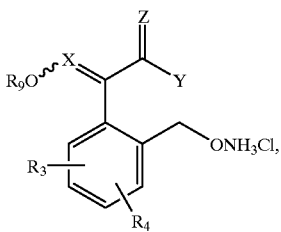

(V)

which is known or can be prepared in accordance with methods known per se and wherein X, Y, Z, $R_3$, $R_4$ and $R_9$ are as defined for formula (I), or b) to prepare a compound of formula (I) wherein Y is NHR: and Z is O, reacting a compound of formula (I) wherein Y is $OR_1$ with a compound of the formula $R_8NH_2$, which is known or can be prepared in accordance with methods known per se and wherein $R_8$ is as defined for formula (I), or c) to prepare a compound of formula (I) wherein Y is $NHR_8$ and Z is S, reacting a compound of formula (I) wherein Y is $R_8NH_2$ and Z is O with $P_4S_{10}$ or Lawesson's reagent (2,4bis-(methoxyphenyl)-1,3-dithia-2,4-diphosphetane-2,4-disulfide), or d) to prepare a compound of formula (I) wherein Z is SO, reacting a compound of formula (I) wherein Z is S with an oxidising agent, and, in each case, if desired, converting a compound of formula (I) obtainable according to the process or by a different method, or an E/Z isomer or tautomer thereof, in each case in free form or in salt form, into a different compound of formula (I) or an E/Z isomer or tautomer thereof, in each case in free form or in salt form, separating a mixture of E/Z isomers obtainable according to the process and isolating the desired isomer and/or converting a free compound of formula (I) obtainable according to the process or by a different method, or an E/Z isomer or tautomer thereof, into a salt, or converting a salt of a compound of formula (I), or of an E/Z isomer or tautomer thereof, obtainable according to the process or by a different method into the free compound of formula (I), or an E/Z isomer or tautomer thereof, or into a different salt.

The invention relates also to a process for the preparation of compounds of formula (III), in each case in free form or in salt form, which process comprises, for example, e) reacting a compound of formula (IV) wherein a, b, n, A, D, G, T, L, $R_2$, $R_5$, $R_6$ and $R_7$ are as defined for formula (I) and wherein the provisos mentioned above for the compounds of formula (I) apply, optionally in the presence of a base, with $H_2NOH$ or with a salt thereof, or f) reacting a compound of formula

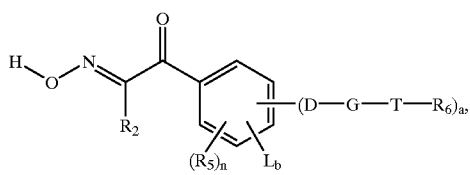

(VI)

wherein a, b, n, A, D, G, T, L, $R_2$, $R_5$, $R_6$ and $R_7$ are as defined for formula (I) and wherein the provisos mentioned above for the compounds of formula (i) apply, optionally in the presence of a base, with a compound of formula $R_7AONH_2$ (VII), which is known or can be prepared according to methods known per so and wherein A and $R_7$ are as defined for formula (I) and, in each case, if desired, converting a compound of formula (III) obtainable according to the process or by a different method, or an E/Z isomer or tautomer thereof, in each case in free form or in salt form, into a different compound of formula (III) or an E/Z isomer or tautomer thereof, in each case in free form or in salt form, separating a mixture of E/Z isomers obtainable according to the process and isolating the desired isomer and/or converting a free compound of formula (III) obtainable according to the process or by a different method, or an E/Z isomer or tautomer thereof, into a salt, or converting a salt of a compound of formula (III), or of an E/Z isomer or tautomer thereof, obtainable according to the process or by a different method into the free compound of formula (III), or an E/Z isomer or tautomer thereof, or into a different salt.

The invention relates also to a process for the preparation of a compound of formula

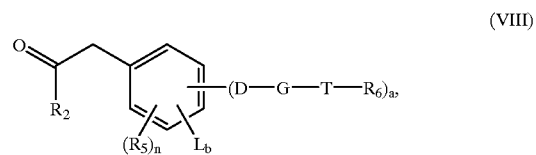

(VIII)

wherein a, b, n, D, G, T, L, $R_2$, $R_5$ and $R_6$ are as defined for formula (I), which process comprises g) in the case where L in formula (VIII) is a radical

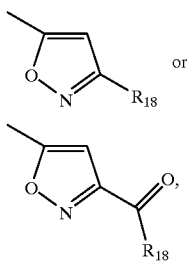

wherein $R_{18}$ is as defined above for formula (I), reacting a compound of formula

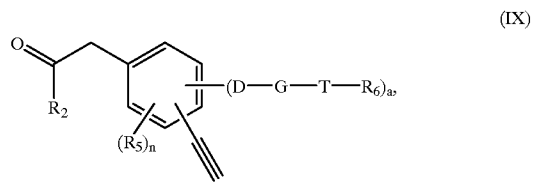

(IX)

wherein a, n, D, G, T and $R_5$ are as defined for formula (I), with a compound of formula $O_2N-CH_2-R_{18}$ (X), wherein $R_{18}$ is as defined for formula (I), in the presence of an isocyanate, especially a phenyl isocyanate; or reacting a compound of formula (IX) with a compound of formula $HO-N=C(Hal)-C(=O)-R_{18}$ (XI), wherein $R_{18}$ is as defined for formula (I) and Hal is a halogen atom, preferably chlorine; or h) when L in the compound of formula (VII) is a radical —C(=O)—C(=O)—R$_{18}$, oxidising a compound of formula

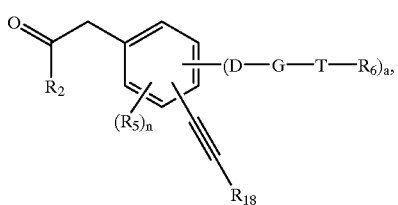

(XII)

wherein a, n, D, G, T, R$_5$ and R$_6$ are as defined for formula (I); or i) reacting a compound of formula

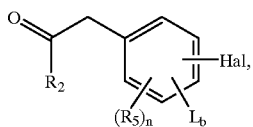

(XIII)

wherein b, n, L, R$_2$ and R$_5$ are as defined for formula (I) and Hal is a halogen atom, preferably fluorine, with a compound of formula R$_6$—T—(C$_1$-C$_8$alkylene)—D—H    (XIV), wherein R$_6$ and T are as defined for formula (I); or k) reacting a compound of formula

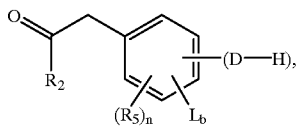

(XV)

wherein b, n, D, G, R$_2$ and R$_5$ are as defined for formula (I), with a compound of formula R$_6$—T—(C$_1$-C$_8$alkylene)—Hal    (XVI), wherein R$_6$ and T are as defined above for formula (I) and Hal is a halogen atom, preferably chlorine or bromine; or l) in the case where, in a compound of formula (VIII), T is —C≡C—, reacting a compound of formula

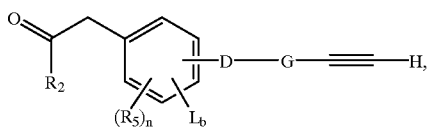

(XVII)

wherein R$_2$, R$_5$, L, D, G, n and b are as defined above for formula (I), with a compound of the formula Hal—R$_6$, which is known or can be prepared in accordance with methods known per se, and wherein Hal is halogen, preferably bromine or iodine, especially iodine, and R$_{18}$ is as defined for formula (I); or m) if L in the compound of formula (VIII) is P(O)$_v$R$_{11}$, R$_{12}$, P(S)$_w$R$_{11}$R$_{12}$ or N(aryl)R$_{13}$, reacting a compound of formula

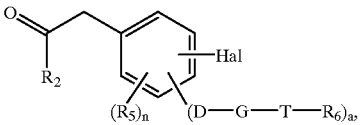

(XVIII)

which is known or can be prepared in accordance with methods known per se, and wherein a, n, D, G, T, R$_2$, R$_5$ and R$_6$ are as defined for formula (I) and Hal is a halogen atom, preferably bromine or iodine, with a compound of formula H—P(O)$_v$R$_{11}$R$_{12}$ (XIX), of formula H—P(S)$_w$R$_{11}$R$_{12}$ (XX), or of formula H—N(aryl)R$_{13}$    (XXI), which are known or can be prepared in accordance with methods known per se, and wherein v, w, R$_{11}$, R$_{12}$, R$_{13}$ and aryl are as defined for formula (I), preferably in the presence of a base and a catalyst, especially a transition metal catalyst, more especially a palladium catalyst or a ferrocene derivative;

and, in each case, if desired, converting a compound of formula (VIII) obtainable according to the process or by a different method, or an E/Z isomer or tautomer thereof, in each case in free form or in salt form, into a different compound of formula (VIII) or an E/Z isomer or tautomer thereof, in each case in free form or in salt form, separating a mixture of E/Z isomers obtainable according to the process and isolating the desired isomer and/or converting a free compound of formula (VIII) obtainable according to the process or by a different method, or an E/Z isomer or tautomer thereof, into a salt, or converting a salt of a compound of formula (VIII), or of an E/Z isomer or tautomer thereof, obtainable according to the process or by a different method into the free compound of formula (VIII), or an E/Z isomer or tautomer thereof, or into a different salt.

The other compounds of formula (VIII) are known or can be prepared in accordance with methods known per se; for example a compound of formula (VIII) wherein T—R$_6$ is —C(R$_{16}$)=C(R$_{17}$)— is obtained by partial hydrogenation of a compound of formula (VIII) wherein T—R$_6$ is —C≡C—R$_6$; a compound of formula (VIII) wherein T is a direct bond is obtained by complete hydrogenation of a compound of formula (VIII) wherein T—R$_6$ is —C≡C—R$_6$ or —C(R$_{16}$)=C(R$_{17}$)—R$_6$, as described in analogous manner in Example P8-1; and a compound of formula (VIII) wherein T—R$_6$ is —C(=N—O—A$_1$—R$_7$)—R$_6$ is obtained by reacting a compound of formula (VIII) wherein T—R$_6$ is —C(=O)—R with a compound of formula H—N—O—A$_1$—R$_7$, R$_6$, R$_7$, A$_1$ and R$_{14}$ to R$_{17}$ are as defined above for formula (I) and Hal is halogen, especially chlorine.

Further aspects of the invention are o) a process for the preparation of compound of formula

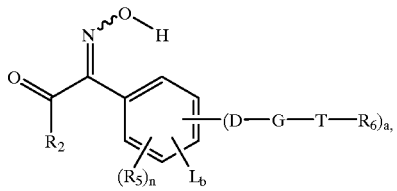

(XXII)

wherein $R_2$, $R_5$, $R_6$, L, D, G, T, a, b and n are as defined in formula (I), in each case in free form or in salt form, which process comprises reacting a compound of the formula (VIII) with a nitrite;

p) a process for the preparation of a compound of the formula (IV), which comprises reacting a compound of the formula (XXII) with a compound of the formula $X_1$—A—$R_7$, wherein $X_1$ is a leaving group such as toluenesulfonyloxy, trifluoromethanesulfonyloxy and halogen;

q) a process for the preparation of a compound of the formula (III), which comprises reacting a compound of the formula (IV) with hydroxylamine;

r) a process for the preparation of a compound of the formula

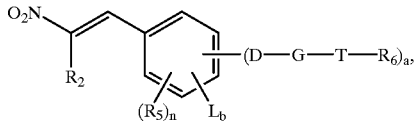

(XXIII)

wherein $R_2$, $R_5$, $R_6$, L, D, G, T, a, b and n are as defined in formula (I), which comprises reacting a compound of the formula

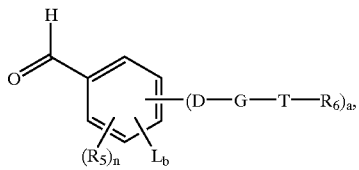

(XXIV)

wherein $R_5$, $R_6$, L, D, G, T, a, b and n are as defined in formula (I), with a nitroalkane;

s) a process for the preparation of a compound of the formula (VIII), which comprises reacting a compound of the formula (XXIII) with $Fe/FeCl_3$ in the presence of an acid, preferably hydrochloric acid.

The observations made above in respect of E/Z isomers and tautomers of compounds (I) apply analogously also in respect of the E/Z isomers and tautomers of starting materials mentioned hereinbefore and hereinafter.

The reactions described hereinbefore and hereinafter are carried out in a manner known per se, for example in the absence or usually in the presence of a suitable solvent or diluent or of a mixture thereof, the reactions being carried out, as required, with cooling, at room temperature or with heating, for example in a temperature range from approximately 0° C. to the boiling temperature of the reaction medium, preferably from approximately 20° C. to approximately +120° C., especially from 60° C. to 80° C., and, if required, in a closed vessel, under pressure, in an inert gas atmosphere and/or under anhydrous conditions. Especially advantageous reaction conditions may be found in the Examples.

In the various reactions, the reactants may be reacted with one another without the addition of a solvent or diluent, for example in molten form. Generally, however, the addition of an inert solvent or diluent or a mixture thereof is advantageous.

The products are isolated in accordance with customary methods, for example by filtration, crystallisation, distillation or chromatography, or any suitable combination of those methods.

Variant a1/a2): Suitable leaving groups $X_1$ in the compounds of formula (II) are, for example, hydroxy, $C_1$–$C_8$alkoxy, halo-$C_1$–$C_8$alkoxy, $C_1$–$C_8$alkanoyloxy, mercapto, $C_1$–$C_8$alkylthio, halo-$C_1$–$C_8$alkylthio, $C_1$–$C_8$alkanesulfonyloxy, halo-$C_1$–$C_8$alkanesulfonyloxy, benzenesulfonyloxy, toluenesulfonyloxy and halogen, preferably toluenesulfonyloxy, trifluoromethanesulfonyloxy and halogen, especially halogen.

Suitable bases for facilitating the reaction are, for example, alkali metal or alkaline earth metal hydroxides, hydrides, amides, alkanolates, acetates, carbonates, dialkylamides or alkylsilylamides, alkylamines, alkylenediamines, unsubstituted or N-alkylated, saturated or unsaturated cycloalkytamines, basic heterocycles, ammonium hydroxides and carbocyclic amines. There may be mentioned by way of example sodium hydroxide, hydride, amide, methanolate, acetate and carbonate, potassium tert-butanolate, hydroxide, carbonate and hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo-[5.4.0]undec-5-ene (DBU).

Examples of solvents or diluents include: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene and tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran and dioxane; ketones, such as acetone, methyl ethyl ketone and methyl isobutyl ketone; alcohols, such as methanol, ethanol, propanol, isopropanol, butanol, ethylene glycol and glycerol; amides, such as N,N-dimethylformamide, N,N-diethylformamide, N,N-dimethylacetamide, N-methylpyrrolidone and hexamethylphosphoric acid triamide; nitriles, such as acetonitrile and propionitrile; and sulfoxides, such as dimethyl sulfoxide. If the reaction is carried out in the presence of a base, bases used in excess, such as triethylamine, pyridine, N-methylmorpholine or N,N-diethylaniline, may also serve as solvents or diluents.

The reaction is carried out advantageously in a temperature range from approximately 0° C. to approximately 180° C., especially from approximately 10° C. to approximately 80° C., in many cases in the range from room temperature to the reflux temperature of the reaction mixture.

Preference is given to a reaction duration of from approximately 0.1 to approximately 24 hours, especially from approximately 0.5 to approximately 2 hours.

In a preferred embodiment of variant a1/a2), a compound of formula (II) is reacted with a compound of formula (III) at from 0° C. to 80° C., preferably from 10° C. to 30° C., in an inert solvent, preferably an amide, especially N,N-dimethylformamide, in the presence of a metal hydride, preferably sodium hydride.

Especially preferred conditions for the reaction are described in Examples P1-1 d), P1-2, P3f) and P5f).

Variant b): Examples of solvents or diluents include those mentioned in variant a1/a2).

The reaction is carried out advantageously in a temperature range from approximately 0° C. to approximately 180° C., especially from approximately 10° C. to approximately 80° C., in many cases in the range from room temperature to the reflux temperature of the reaction mixture. Preference is given to a reaction duration of from approximately 0.1 to approximately 24 hours, especially from approximately 0.5 to approximately 2 hours.

Especially preferred conditions for the reaction are described in Examples P1-3 and P5-1 g).

Variant c): Examples of solvents or diluents include: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene and tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran and dioxane; and sulfoxides, such as dimethyl sulfoxide.

The reaction is carried out advantageously in a temperature range from approximately 0° C. to approximately +120° C., preferably from approximately 80° C. to approximately +120° C.

Preference is given to a reaction duration of from approximately 0.1 to approximately 24 hours, especially from approximately 0.5 to approximately 2 hours.

Variant d): Suitable oxidising agents are, for example, inorganic peroxides, such as sodium perborate, or hydrogen peroxide, or organic peracids, such as perbenzoic acid or peracetic acid, or mixtures of organic acids and hydrogen peroxide, for example acetic acid/hydrogen peroxide.

Examples of solvents or diluents include: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene and tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran and dioxane; ketones, such as acetone, methyl ethyl ketone and methyl isobutyl ketone; alcohols, such as methanol, ethanol and propanol; amides, such as N,N-dimethylformamide, N,N-diethylformamide, N,N-dimethylacetamide, N-methylpyrrolidone and hexamethylphosphoric acid triamide; nitiles, such as acetonitrile and propionitrile; and sulfoxides, such as dimethyl sulfoxide. If the reaction is carried out in the presence of an organic acid or peracid, acids used in excess, for example strong organic carboxylic acids, such as unsubstituted or substituted, for example halo-substituted, $C_1$–$C_4$alkanecarboxylic acids, e.g. formic acid, acetic acid or propionic acid, may also serve as solvent or diluent.

The reaction is carried out advantageously in a temperature range from approximately 0° C. to approximately +120° C., preferably from approximately 0° C. to approximately +40° C.

Preference is given to a reaction duration of from approximately 0.1 to approximately 24 hours, especially from approximately 0.5 to approximately 2 hours.

Variant e): Suitable bases for facilitating the reaction are, for example, those mentioned in variant a1/a2).

Examples of solvents or diluents include those mentioned in variant a1/a2).

The reaction is carried out advantageously in a temperature range from approximately 0° C. to approximately 180° C., especially from approximately 10° C. to approximately 80° C., in many cases in the range from room temperature to the reflux temperature of the reaction mixture.

Preference is given to a reaction duration of from approximately 0.1 to approximately 24 hours, especially from approximately 0.5 to approximately 2 hours.

Especially preferred conditions may be found in Example P3 e).

Variant D): Suitable bases for facilitating the reaction are, for example, those mentioned in variant a1/a2).

Examples of solvents or diluents include those mentioned in variant a1/a2).

The reaction is carried out advantageously in a temperature range from approximately 0° C. to approximately 180° C., especially from approximately 10° C. to approximately 80° C., in many cases in the range from room temperature to the reflux temperature of the reaction mixture.

Preference is given to a reaction duration of from approximately 0.1 to approximately 24 hours, especially from approximately 0.5 to approximately 2 hours.

In a preferred embodiment of variant f), a compound of formula (VI) is reacted with a compound of formula (VII) at from 0° C. to 120° C., preferably from 60° C. to 120° C., in an inert solvent, preferably an amine, especially pyridine. Especially preferred conditions may be found in Example P1-1c) and also in the analogous reaction described in Example P3 e).

Especially preferred conditions for process variants g), h), i), k), l) and m) may be found in the Examples. In particular, the conditions for the process according to variant g) may be found in Examples P9-1 and P9-2; according to variant h) in Example P6-1; according to variant i) in Example P1-la); according to variant k) in Examples P3b) and P5b); according to variant 1) in Example P7-1; and according to variant m) in Examples P101 and P12-1 or applied analogously to those processes.

Some of the compounds of formulae (I) and (III) to (XXIV) may be in the form of one of the possible isomers or in the form of a mixture thereof, for example according to the number of asymmetric carbon atoms and the absolute and relative configuration thereof in the form of pure isomers, such as antipodes and/or diastereoisomers, or in the form of mixtures of isomers, such as mixtures of enantiomers, for example racemates, mixtures of diastereoisomers or mixtures of racemates; the invention relates both to the pure isomers and to all possible mixtures of isomers and this is to be understood accordingly hereinbefore and hereinafter, even if stereochemical details are not specifically mentioned in each case.

Mixtures of diastereoisomers and mixtures of racemates of compounds of formulae (I) and some of the compounds (III) to (XXIV) that are obtainable in accordance with the process depending upon the starting materials and procedures chosen, or by other means, can be separated into the pure diastereoisomers or racemates in known manner on the basis of the physicochemical differences between the constituents, for example by fractional crystallisation, distillation and/or chromatography.

Mixtures of enantiomers, such as racemates, so obtainable can be separated into the optical antipodes by known methods, for example by recrystallisation from an optically active solvent, by chromatography on chiral adsorbents, for example high-pressure liquid chromatography (HPLG) on acetyl cellulose, with the aid of suitable microorganisms, by cleavage with specific immobilised enzymes, and via the formation of inclusion compounds, for example using chiral crown ethers, in which case only one enantiomer is complexed.

Apart from by the separation of corresponding mixtures of isomers, it is possible according to the invention to obtain pure diastereoisomers or enantiomers also by generally known methods of diastereoselective or enantioselective synthesis, for example by carrying out the process according to the invention with starting materials having appropriate stereochemistry.

It is advantageous to isolate or synthesise the biologically more active isomer, for example enantiomer, or mixture of isomers, for example mixture of enantiomers, insofar as the individual components have different biological activity.

Some of the compounds (I) and (III) to (XXIV) can also be obtained in the form of their hydrates and/or may include other solvents, for example solvents that may have been used for the crystallisation of compounds in solid form.

The invention relates to all those embodiments of the process according to which a compound obtainable as starting material or intermediate at any stage of the process is used as starting material and all or some of the remaining steps are carried out, or a starting material is used in the form of a derivative or a salt and/or its racemates or antipodes, or, especially, is formed under the reaction conditions.

In the process of the present invention there are preferably used those starting materials and intermediates which result in the compounds of formula (I) described at the beginning as being especially valuable.

The invention relates especially to the preparation processes described in Examples P1 to P12.

The invention relates also to starting materials and intermediates used according to the invention in the preparation of compounds of formula (I), especially the compounds of formulae (III), (IV), (VI), (VIII), (IX), (XII), (XIII), (XV), (XVII), (XVIII), (XXII), (XXIII) and (XXIV), which are novel, to their use and to processes for the preparation thereof. In particular, the compounds of formulae (III) and (VI) can be prepared analogously to Examples P1 c) and P1 b), respectively.

The compounds of formulae (II), (V), (VII), (X), (XI), (XIV), (XVI) and (XIX) to (XXI) are known or can be prepared in accordance with methods known per se.

In the area of pest control, the compounds of formula (I) according to the invention are valuable preventive and/or curative active ingredients having a very advantageous biocidal spectrum even at low rates of concentration, while being well tolerated by warm-blooded animals, fish and plants. The compounds of the invention are effective against all or individual development stages of normally sensitive animal pests, but also of resistant animal pests, such as insects and representatives of the order Acarina, and phytopathogenic fungi. The insecticidal, ovicidal and/or acaricidal action of the compounds of the invention may manifest itself directly, i.e. in the mortality of the pests, which occurs immediately or only after some time, for example during moulting, or of their eggs, or indirectly, for example in reduced oviposition and/or hatching rate, good activity corresponding to a mortality of at least 50 to 60%.

The mentioned animal pests include, for example, those mentioned in European Patent Application EP-A-736 252. Accordingly, the said pests mentioned in EP-A-736 252 are included by reference in the subject matter of the present invention.

The mentioned phytopathogenic fungi include, for example:
of the class of the *Fungi imperfecti*, for example, Botrytis spp., Pyricularia spp., Helminthosporium spp., Fusarium spp., Septoria spp., Cereo spora spp. and Altemaria spp.;
of the class of the Basidiomycetes, for example, Rhizoctonia spp., Hemileia spp. and Puccinia spp.;
of the class of the Ascomycetes, for example, Venturia spp., Erysiphe spp., Podosphaera spp., Monilinia spp. and Uncinula spp.; and
of the class of the Oomycetes, for example, Phytophthora spp., Pythium spp. and Plasmopara spp..

With the compounds according to the invention it is possible to control, i.e. to inhibit or destroy, pests of the mentioned type occurring especially on plants, more especially on useful plants and ornamentals in agriculture, in horticulture and in forestry, or on parts of such plants, such as the fruit, blossom, leaves, stems, tubers or roots, while in some cases parts of the plants that grow later are also protected against those pests.

Target crops are especially cereals, such as wheat, barley, rye, oats, rice, maize and sorghum; beet, such as sugar beet and fodder beet; fruit, such as pomes, stone fruit and soft fruit, such as apples, pears, plums, peaches, almonds, cherries, or berries, for example strawberries, raspberries and blackberries; leguminous plants, such as beans, lentils, peas and soybeans; oil plants, such as rape, mustard, poppy, olives, sunflowers, coconut, castor oil plants, cocoa beans and groundnuts; cucurbitaceae, such as marrows, cucumber and melons; fibre plants, such as cotton, flax, hemp and jute; citrus fruit, such as oranges, lemons, grapefruit and mandarins; vegetables, such as spinach, lettuce, asparagus, cabbages, carrots, onions, tomatoes, potatoes and paprika; lauraceae, such as avocados, cinnamon and camphor; and tobacco, nuts, coffee, aubergines, sugar cane, tea, pepper, vines, hops, bananas and natural rubber plants, as well as ornamentals.

The compounds according to the invention are especially suitable for controlling insects and representatives of the order Acarina, especially plant-destructive feeding insects, such as *Anthonomus grandis, Diabrotica balteata, Heliothis virescens larvae, Plutella xylostella* and *Spodoptera littoralis larvae,* and spider mites, such as Tetranychus spp., in cotton, fruit, maize, soybean, rape and vegetable crops.

Further areas of use of the compounds according to the invention are the protection of stored goods and stocks and materials, and also in the hygiene sector, especially the protection of domestic animals and productive livestock against pests of the mentioned type.

The invention therefore relates also to pesticides, such as emulsifiable concentrates, suspension concentrates, directly sprayable or dilutable solutions, coatable pastes, dilute emulsions, wettable powders, soluble powders, dispersible powders, wettable powders, dusts, granules or encapsulations in polymer substances, comprising—at least—one of the compounds of the invention, the type of formulation being chosen in accordance with the intended objectives and prevailing circumstances.

The active ingredient is used in those compositions in pure form: a solid active ingredient, for example, in a specific particle size, or preferably together with—at least—one of the adjuvants customary in formulation technology, such as extenders, for example solvents or solid carriers, or surface-active compounds (surfactants).

Formulation adjuvants used are, e.g., solid carriers, solvents, stabilisers, "slow release" adjuvants, colorants and optionally surface-active substances (surfactants). Suitable carriers and adjuvants include any substances customarily used in plant protection compositions, especially in compositions for controlling slugs and snails. Suitable adjuvants, such as solvents, solid carriers, surface-active compounds, non-ionic surfactants, cationic surfactants, anionic surfactants and other adjuvants in the compositions used according to the invention include, for example, the same substances as those described in EP-A-736 252. Accordingly, the said adjuvants mentioned in EP-A-736 252 are included by reference in the subject matter of the present invention.

The compositions usually comprise 0.1 to 99%, preferably 0.1 to 95%, of active ingredient, and 1 to 99.9%, preferably 5 to 99.9%, of—at least—one solid or liquid adjuvant, it generally being possible for 0 to 25%, preferably 0.1 to 20%, of the composition to be surfactants (in each case percentages are by weight). Whereas commercial products will preferably be formulated as concentrates, the end user will normally employ dilute formulations which have substantially lower active ingredient concentrations. Preferred formulations have especially the following composition (%=percent by weight):

| Emulsifiable concentrates: | |
| --- | --- |
| active ingredient: | 1 to 90%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granules: | |
| active ingredient: | 0.5 to 30%, preferably 3 to 15% |
| solid carrier: | 99.5 to 70%, preferably 97 to 85% |

The activity of the compositions according to the invention can be substantially broadened and adapted to prevailing circumstances by the addition of other insecticidal, acaricidal and/or fungicidal active ingredients. Examples of suitable additional active ingredients include representatives of the following classes of compounds: organophosphorus compounds, nitrophenols and derivatives, formamidines, ureas, carbamates, pyrethroids, chlorinated hydrocarbons and *Bacillus thuringiensis* preparations. The compositions according to the invention may also comprise further solid or liquid adjuvants, such as stabilisers, for example vegetable oils or epoxidised vegetable oils (e.g. epoxidised coconut oil, rape oil or soybean oil), antifoams, for example silicone oil, preservatives, viscosity regulators, binders and/or tackifiers, as well as fertilisers or other active ingredients for obtaining special effects, for example bactericides, nematicides, molluscicides or selective herbicides.

The compositions according to the invention are prepared in known manner, in the absence of adjuvants, for example by grinding and/or sieving a solid active ingredient or mixture of active ingredients, for example to a specific particle size, or in the presence of at least one adjuvant, for example by intimately mixing and/or grinding the active ingredient or mixture of active ingredients with the adjuvant (s). The invention relates also to those processes for the preparation of the compositions according to the invention and to the use of the compounds of formula (I) in the preparation of those compositions.

The invention relates also to the methods of application of the compositions, i.e. the methods of controlling pests of the mentioned type, such as spraying, atomising, dusting, coating, dressing, scattering or pouring, which are selected in accordance with the intended objectives and prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of plant protection is application to the foliage of the plants (foliar application), the number of applications and the rate of application depending on the risk of infestation by the pest in question. However, the active ingredient can also penetrate the plants through the roots (systemic action) if the locus of the plants is impregnated with a liquid formulation or if the active ingredient is incorporated in solid form into the locus of the plants, for example into the soil, e.g. in granular form (soil application). In paddy rice crops, such granules may be applied in metered amounts to the flooded rice field.

The compositions according to the invention are also suitable for protecting plant propagation material, e.g. seed, such as fruit, tubers or grains, or plant cuttings, from fungal infections and animal pests. The propagation material can be treated with the formulation before planting: seed, for example, can be dressed before being sown. The compounds of the invention can also be applied to grains (coating), either by impregnating the grains with a liquid formulation or by coating them with a solid formulation. The formulation can also be applied to the planting site when the propagation material is being planted, for example to the seed furrow during sowing. The invention relates also to those methods of treating plant propagation material and to the plant propagation material thus treated.

The following Examples are intended to illustrate the invention. They do not limit the invention. Temperatures are given in degrees Celsius.

PREPARATION EXAMPLES

Example P1-1: 2-[[[(1-Methyl-2-(4(1-{4-chlorophenyl}-ethoxy)-phenyl)-[ethoximino]-ethylidene)amino]oxy]methyl]-α-(methoxymethylene)-phenylacetic acid methyl ester a) 1-[4-(1-{4-Chlorophenyl}ethoxy)-phenyl]propan-1-one 26.5 g of 1-(4-chlorophenyl)-ethanol are added dropwise to 7.9 g of sodium hydride (55% in oil) in 250 ml of dimethylacetamide and the mixture is stirred at room temperature for 30 minutes. 25.7 g of 4-fluoropropiophenone are then added dropwise; the mixture is heated to 100° C. and stirred for 90 minutes. After cooling, the reaction mixture is concentrated in vacua; the residue is taken up in ethyl acetate, washed twice with water and once with saturated sodium chloride solution and dried over sodium sulfate. The solvent is evaporated off in vacuo and the residue is purified by recrystallisation from hexane to yield the title compound having a melting point 70–71° C.

b) 1-(4(1-{4-Chlorophenyl}-ethoxy)phenyl-1,2-propanedione-2-oxime

Dry HCl gas is introduced into 200 ml of diethyl ether over a period of 0.5 minutes and 43.2 g of 1-[4-(1-{4-chlorophenyl}-ethoxy)-phenyl]-propan-1-one are then added. 21.0 g of isopentyl nitrite are then added dropwise and the reaction mixture is then stirred for 3 hours at room temperature. The reaction mixture is concentrated by evaporation in vacuo and the crude product is purified by chromatography on silica gel using ethyl acetate/hexane (1:3), yielding the title compound having a melting point of 88–90° C.

c) 1-[4-(1-{4-Chlorophenyl}-ethoxy)-phenyl]-1,2-propanedione-[ethyloxime]-2-oxime A mixture of 29.0 g of 1-(4-(1-{4-chlorophenyl}-ethoxy)-phenyl)-1,2-propanedione-2-oxime and 9.4 g of O-ethylhydroxylamine hydrochloride in 150 ml of pyridine is boiled at reflux for 1 hour. After cooling, the reaction mixture is concentrated by evaporation in vacuo. The residue is dissolved in ethyl acetate; the organic phase is washed twice with water and once with saturated sodium chloride solution, dried with sodium sulfate and concentrated by evaporation. The crude product is stirred together with hexane; filtration is carried out and the filter residue is dried, yielding the title product having a melting point of 132–134° C.

d) 2-[[[(1-Methyl-2-(4-(1-{4-chlorophenyl}-ethoxy)-phenyl)-[ethoxyimino]ethylidene)-amino]oxy]methyl]-α-(methoxymethylene)-phenylacetic acid methyl ester 7 g of 1-[4-(1-{4-chlorophenyl}-ethoxy)-phenyl]-1,2-propanedione-[ethyloxime]-2-oxime dissolved in 25 ml of N,N-dimethylformamide are added dropwise to a suspension of 0.9 g of sodium hydride (55% in oil) in 40 ml of N,N-dimethylformamide and the reaction mixture is then stirred for 10 minutes at room temperature. 5.5 g of 2-(bromomethyl)-α-(methoxymethylene)-phenylacetic acid methyl ester in 20 ml of N,N-dimethylformamide are then added dropwise and the reaction mixture is stirred for a further 1 hour at room temperature. The mixture is then rendered acidic with acetic acid and concentrated by evaporation in vacuo. The residue is dissolved in ethyl acetate and the solution is washed three times with water and once with saturated sodium chloride solution, dried with sodium sulfate and concentrated by evaporation in vacuo. Purification by flash chromatography (silica gel, ethyl acetate/hexane 1:3) yields the E isomer of the title compound having a melting point of 107–109° C. (compound 1-4.2).

Example P1-2: 2-[[[(1-Methyl-2-(4-(1-{4-chlorophenyl}-ethoxy)-phenyl)[ethoxyimino]ethylidene) amino]oxy] methyl]-α-(methoxyimino)-phenylacetic acid methyl ester In a manner analogous to that described in Example P1-1 d), 1-[4-(1-{4-chlorophenyl}ethoxy)-phenyl]-1,2-propanedione-[ethyloxime]-2-oxime and 2-(bromomethyl)-α-(methoxyimino)-phenylacetic acid methyl ester yield the title compound having a melting point of 111–113° C. (compound 2.4-2).

Example P1-3: 2-[[[(1-Methyl-2-(4-(1-{4-chlorophenyl}-ethoxy)-phenyl)-[ethoxyimino]ethylidene) amino]oxy] methyl]-α-(methoxyimino)-phenylacetic acid methylamide A mixture of 4.0 g of 2-[[[(1-methyl-2-(4-(1-{4-chlorophenyl}-ethoxy)-phenyl)-2-E-[ethoxyimino] ethylidene)amino]oxy]methyl]-α-(methoxyimino)-phenylacetic acid methyl ester and 5.3 ml of a 8M solution of methylamine in ethanol is left to stand at room temperature for 4 days. The mixture is then concentrated by evaporation in vacuo. The residue is taken up with methyl acetate; the solution is washed with water and saturated sodium chloride solution, dried over sodium sulfate and concentrated by evaporation in vacuo. The residue is recrystallised from methyl acetate/hexane 1:1 to yield the title compound having a melting point of 81–83° C. (compound 3-4.2).

Example P2: It is also possible to prepare the other compounds listed in Tables 1.1 to 3.26 in a manner analogous to that described in Example P1; c.propyl denotes cyclopropyl.

TABLE A

Compounds of general formula (I) wherein A-$R_7$ is defined as follows

| Number | A-$R_7$ |
|---|---|
| A.1 | $CH_3$ |
| A.2 | $C_2H_5$ |
| A.3 | n-$C_3H_7$ |
| A.4 | iso-$C_3H_7$ |
| A.5 | n-$C_4H_9$ |
| A.6 | n-$C_6H_{13}$ |
| A.7 | $CH_2F$ |
| A.8 | $CHF_2$ |
| A.9 | $CH_2CF_3$ |
| A.10 | $CH_2CH=CH_2$ |
| A.11 | $CH_2CH=CHCH_3$ |
| A.12 | $CH_2CH=C(CH_3)_2$ |
| A.13 | $CH_2CH=CHCl$ |
| A.14 | $CH_2CH=CCl_2$ |
| A.15 | $CH_2C(CH_3)=CH_2$ |
| A.16 | $CH_2C\equiv CH$ |
| A.17 | $CH_2Si(CH_3)_3$ |
| A.18 | $CH_2$-c.propyl-2,2-$Cl_2$ |
| A.19 | $CH_2$-c.propyl |
| A.20 | $CH_2CN$ |
| A.21 | $CH_2COOCH_3$ |
| A.22 | $CH_2COOC_2H_5$ |
| A.23 | $CH_2COO$-iso-$C_3H_7$ |
| A.24 | $CH(CH_3)COOC_2H_5$ |
| A.25 | $C(=O)OC_2H_5$ |
| A.26 | $C(=O)NHCH_3$ |
| A.27 | $C(=O)C(=O)OC_2H_5$ |
| A.28 | $CH_2C_6H_5$ |
| A.29 | $CH_2C_6H_4$-2-F |
| A.30 | $CH_2C_6H_4$-3-F |
| A.31 | $CH_2C_6H_4$-4-F |
| A.32 | $CH_2C_6H_4$-2-Cl |
| A.33 | $CH_2C_6H_4$-3-Cl |
| A.34 | $CH_2C_6H_4$-4-Cl |
| A.35 | $CH_2C_6H_4$-2-Br |
| A.36 | $CH_2C_6H_4$-3-Br |
| A.37 | $CH_2C_6H_4$-4-Br |
| A.38 | $CH_2C_6H_4$-2-$CF_3$ |
| A.39 | $CH_2C_6H_4$-3-$CF_3$ |
| A.40 | $CH_2C_6H_4$-4-$CF_3$ |

23

Table 1-1: Compounds of general formula

TABLE 1-1

Compounds of general formual (I.1)

structure: CH$_3$O-N=C(COOCH$_3$)-C$_6$H$_4$-CH$_2$-O-N=C(CH$_3$)-C$_6$H$_4$-O-CH(CH$_3$)-C$_6$H$_4$-(R$_5$)$_s$ with N-O-A-R$_7$ substituent wherein $(R_5)_S$ is 4-CF$_3$ and the substituent A—R$_7$ corresponds in each case to a line of Table A.

Table 1-2: Compounds of general formula (I.1) wherein $(R_5)_S$ is 3-CF$_3$ and the substituent A—R$_7$ corresponds in each case to a line of Table A.

Table 1-3: Compounds of general formula (I.1) wherein $(R_5)_S$ is 2-CF$_3$ and the substituent A—R$_7$ corresponds in each case to a line of Table A.

Table 1-4: Compounds of general formula (I.1) wherein $(R_5)_S$ is 4-Cl and the substituent A—R$_7$ corresponds in each case to a line of Table A.

Table 1-5: Compounds of general formula (I.1) wherein $(R_5)_S$ is 3-Cl and the substituent A—R$_7$ corresponds in each case to a line of Table A.

Table 1-6: Compounds of general formula (I.1) wherein $(R_5)_S$ is 2-Cl and the substituent A—R$_7$ corresponds in each case to a line of Table A.

Table 1-7: Compounds of general formula (I.1) wherein $(R_5)_S$ is 4-Br and the substituent A—R$_7$ corresponds in each case to a line of Table A.

Table 1-8: Compounds of general formula (I.1) wherein $(R_5)_S$ is 3-Br and the substituent A—R$_7$ corresponds in each case to a line of Table A.

Table 1-9: Compounds of general formula (I.1) wherein $(R_5)_S$ is 2-Br and the substituent A—R$_7$ corresponds in each case to a line of Table A.

Table 1-10: Compounds of general formula (I.1) wherein $(R_5)_S$ is 4-F and the substituent A—R$_7$ corresponds in each case to a line of Table A.

Table 1-11: Compounds of general formula (I.1) wherein $(R_5)_S$ is 3-F and the substituent A—R$_7$ corresponds in each case to a line of Table A.

Table 1-12: Compounds of general formula (I.1) wherein $(R_5)_S$ is 2-F and the substituent A—R$_7$ corresponds in each case to a line of Table A.

Table 1-13: Compounds of general formula (I.1) wherein $(R_5)_S$ is 2,4-Cl$_2$ and the substituent A—R$_7$ corresponds in each case to a line of Table A.

Table 1-14: Compounds of general formula (I.1) wherein $(R_5)_S$ is 3,4-C$_6$ and the substituent A—R$_7$ corresponds in each case to a line of Table A.

Table 1-15: Compounds of general formula (I.1) wherein $(R_5)_S$ is 4-O—CF$_3$ and the substituent A—R$_7$ corresponds in each case to a line of Table A.

Table 1-16: Compounds of general formula (I.1) wherein $(R_5)_S$ is 4-CH$_3$ and the substituent A—R$_7$ corresponds in each case to a line of Table A.

Table 1-17: Compounds of general formula (I.1) wherein $(R_5)_S$ is 4-C$_2$H$_5$ and the substituent A—R$_7$ corresponds in each case to a line of Table A.

Table 1-18: Compounds of general formula (I.1) wherein $(R_5)_S$ is 4-n-C$_3$H$_7$ and the substituent A—R$_7$ corresponds in each case to a line of Table A.

Table 1-19: Compounds of general formula (I.1) wherein $(R_5)_S$ is 4-iso-C$_3$H$_7$ and the substituent A—R$_7$ corresponds in each case to a line of Table A.

Table 1-20: Compounds of general formula (I.1) wherein $(R_5)_S$ is 4-n-C$_4$H$_9$ and the substituent A—R$_7$ corresponds in each case to a line of Table A.

Table 1-21: Compounds of general formula (I.1) wherein $(R_5)_S$ is 4-isobutyl and the substituent A—R$_7$ corresponds in each case to a line of Table A.

Table 1-22: Compounds of general formula (I.1) wherein $(R_5)_S$ is 4-sec-butyl and the substituent A—R$_7$ corresponds in each case to a line of Table A.

Table 1-23: Compounds of general formula (I.1) wherein $(R_5)_S$ is 4-tert-butyl and the substituent A—R$_7$ corresponds in each case to a line of Table A.

Table 1-24: Compounds of general formula (I.1) wherein $(R_5)_S$ is 4-CN and the substituent A—R$_7$ corresponds in each case to a line of Table A.

Table 1-25: Compounds of general formula (I.1) wherein $(R_5)_S$ is 4-O—CH$_3$ and the substituent A—R$_7$ corresponds in each case to a line of Table A.

Table 1-26: Compounds of general formula (I.1) wherein $(R_5)_S$ is 2,4-F$_2$ and the substituent A—R$_7$ corresponds in each case to a line of Table A.

Compound of formula (I.1) wherein A—R$_7$ is ethyl and $(R_5)_S$ is 4-chlorine: m.p.: 107–109° C. (compound 1-4.2).

TABLE 2-1

Compounds of general formula (I.2)

structure: CH$_3$O-N=C(COOCH$_3$)-C$_6$H$_4$-CH$_2$-O-N=C(CH$_3$)-C$_6$H$_4$-O-CH(CH$_3$)-C$_6$H$_4$-(R$_5$)$_s$ with N-O-A-R$_7$ substituent wherein $(R_5)_S$ is 4-CF$_3$ and the substituent A—R$_7$ corresponds in each case to a line of Table A.

Table 2-2: Compounds of general formula (I.2) wherein $(R_5)_S$ is 3-CF$_3$ and the substituent A—R$_7$ corresponds in each case to a line of Table A.

Table 2-3: Compounds of general formula (I.2) wherein $(R_5)_S$ is 2-CF$_3$ and the substituent A—R$_7$ corresponds in each case to a line of Table A.

Table 2-4: Compounds of general formula (I.2) wherein $(R_5)_S$ is 4-Cl and the substituent A—R$_7$ corresponds in each case to a line of Table A.

Table 2-5: Compounds of general formula (I.2) wherein $(R_5)_S$ is 3-Cl and the substituent A—R$_7$ corresponds in each case to a line of Table A.

Table 2-6: Compounds of general formula (I.2) wherein $(R_5)_S$ is 2-Cl and the substituent A—R$_7$ corresponds in each case to a line of Table A.

Table 2-7: Compounds of general formula (I.2) wherein $(R_5)_S$ is 4-Br and the substituent A—R$_7$ corresponds in each case to a line of Table A.

Table 28: Compounds of general formula (I.2) wherein $(R_5)_S$ is 3-Br and the substituent A—R$_7$ corresponds in each case to a line of Table A.

Table 2-9: Compounds of general formula (I.2) wherein $(R_5)_S$ is 2-Br and the substituent A—R$_7$ corresponds in each case to a line of Table A.

Table 2-10: Compounds of general formula (I.2) wherein $(R_5)_S$ is 4-F and the substituent A—R$_7$ corresponds in each case to a line of Table A.

Table 2-11: Compounds of general formula (I.2) wherein $(R_5)_S$ is 3-F and the substituent A—$R_7$ corresponds in each case to a line of Table A.

Table 2-12: Compounds of general formula (I.2) wherein $(R_5)_S$ is 2-F and the substituent A—$R_7$ corresponds in each case to a line of Table A.

Table 2-13: Compounds of general formula (I.2) wherein $(R_5)_S$ is 2,4-$Cl_2$ and the substituent A—$R_7$ corresponds in each case to a line of Table A.

Table 2-14: Compounds of general formula (I.2) wherein $(R_5)_S$ is 3,4-$Cl_2$ and the substituent A—$R_7$ corresponds in each case to a line of Table A.

Table 2-15: Compounds of general formula (I.2) wherein $(R_5)_S$ is 4-O—$CF_3$ and the substituent A—$R_7$ corresponds in each case to a line of Table A.

Table 2-16: Compounds of general formula (I.2) wherein $(R_5)_S$ is 4-$CH_3$ and the substituent A—$R_7$ corresponds in each case to a line of Table A.

Table 2-17: Compounds of general formula (I.2) wherein $(R_5)_S$ is 4-$C_2H_5$ and the substituent A—$R_7$ corresponds in each case to a line of Table A.

Table 2-18: Compounds of general formula (I.2) wherein $(R_5)_S$ is 4-n-$C_3H_7$ and the substituent A—$R_7$ corresponds in each case to a line of Table A.

Table 2-19: Compounds of general formula (I.2) wherein $(R_5)_S$ is 4-iso-$C_3H_7$ and the substituent A—$R_7$ corresponds in each case to a line of Table A.

Table 2-20: Compounds of general formula (I.2) wherein $(R_5)_S$ is 4-n-$C_4H_9$ and the substituent A—$R_7$ corresponds in each case to a line of Table A.

Table 2-21: Compounds of general formula (I.2) wherein $(R_5)_S$ is 4-isobutyl and the substituent A—$R_7$ corresponds in each case to a line of Table A.

Table 2-22: Compounds of general formula (I.2) wherein $(R_5)_S$ is 4-sec-butyl and the substituent A—$R_7$ corresponds in each case to a line of Table A.

Table 2-23: Compounds of general formula (I.2) wherein $(R_5)_S$ is 4-tert-butyl and the substituent A—$R_7$ corresponds in each case to a line of Table A.

Table 2-24: Compounds of general formula (I.2) wherein $(R_5)_S$ is 4-CN and the substituent A—$R_7$ corresponds in each case to a line of Table k Table 2-25: Compounds of general formula (I.2) wherein $(R_5)_S$ is 4-O—$CH_3$ and the substituent A—$R_7$ corresponds in each case to a line of Table A.

Table 2-26: Compounds of general formula (I.2) wherein $(R_5)_S$ is 2,4-$F_2$ and the substituent A—$R_7$ corresponds in each case to a line of Table A.

Compound of formula (I.2) wherein A—$R_7$ is ethyl and $(R_5)_S$ is 4-chlorine: m.p.: 111–113° C. (compound 2-4.2).

Table 3-1: Compounds of general formula

TABLE 3-1

Compounds of general formula (I.3)

wherein $(R_5)_S$ is 4-$CF_3$ and the substituent A—$R_7$ corresponds in each case to a line of Table A.

Table 3-2: Compounds of general formula (I.3) wherein $(R_5)_S$ is 3-$CF_3$ and the substituent A—$R_7$ corresponds in each case to a line of Table A.

Table 3-3: Compounds of general formula (I.3) wherein $(R_5)_S$ is 2-$CF_3$ and the substituent A—$R_7$ corresponds in each case to a line of Table A.

Table 3-4: Compounds of general formula (I.3) wherein $(R_5)_S$ is 4-Cl and the substituent A—$R_7$ corresponds in each case to a line of Table A.

Table 3-5: Compounds of general formula (I.3) wherein $(R_5)_S$ is 3-Cl and the substituent A—$R_7$ corresponds in each case to a line of Table A.

Table 3-6: Compounds of general formula (I.3) wherein $(R_5)_S$ is 2-Cl and the substituent A—$R_7$ corresponds in each case to a line of Table A.

Table 3-7: Compounds of general formula (I.3) wherein $(R_5)_S$ is 4-Br and the substituent A—$R_7$ corresponds in each case to a line of Table A.

Table 3-8: Compounds of general formula (I.3) wherein $(R_5)_S$ is 3-Br and the substituent A—$R_7$ corresponds in each case to a line of Table A.

Table 3-9: Compounds of general formula (I.3) wherein $(R_5)_S$ is 2-Br and the substituent A—$R_7$ corresponds in each case to a line of Table A.

Table 3-10: Compounds of general formula (I.3) wherein $(R_5)_S$ is 4-F and the substituent A—$R_7$ corresponds in each case to a line of Table A.

Table 3-11: Compounds of general formula (I.3) wherein $(R_5)_S$ is 3-F and the substituent A—$R_7$ corresponds in each case to a line of Table A.

Table 3-12: Compounds of general formula (I.3) wherein $(R_5)_S$ is 2-F and the substituent A—$R_7$ corresponds in each case to a line of Table A.

Table 3-13: Compounds of general formula (I.3) wherein $(R_5)_S$ is 2,4-Cl and the substituent A—$R_7$ corresponds in each case to a line of Table A.

Table 3-14: Compounds of general formula (I.3) wherein $(R_6)_S$ is 3,4-$Cl_2$ and the substituent A—$R_7$ corresponds in each case to a line of Table A.

Table 3-15: Compounds of general formula (I.3) wherein $(R_5)_S$ is 4-O—$CF_3$ and the substituent A—$R_7$ corresponds in each case to a line of Table A.

Table 3-16: Compounds of general formula (I.3) wherein $(R_5)_S$ is 4-$CH_3$ and the substituent A—$R_7$ corresponds in each case to a fine of Table A.

Table 3-17: Compounds of general formula (I.3) wherein $(R_5)_S$ is 4-$C_2H_5$ and the substituent A—$R_7$ corresponds in each case to a line of Table A.

Table 3-18: Compounds of general formula (I.3) wherein $(R_5)_S$ is 4-n-$C_3H_7$ and the substituent A—$R_7$ corresponds in each case to a line of Table A.

Table 3-19: Compounds of general formula (I.3) wherein $(R_5)_S$ is 4iso-$C_3H_7$ and the substituent A—$R_7$ corresponds in each case to a line of Table A Table 3-20: Compounds of general formula (I.3) wherein $(R_5)_S$ is 4-n-$C_4H_9$ and the substituent A—$R_7$ corresponds in each case to a line of Table A.

Table 3-21: Compounds of general formula (I.3) wherein $(R_5)_S$ is 4-isobutyl and the substituent A—$R_7$ corresponds in each case to a line of Table A.

Table 3-22: Compounds of general formula (I.3) wherein $(R_5)_S$ is 4-sec-butyl and the substituent A—$R_7$ corresponds in each case to a line of Table A.

Table 3-23: Compounds of general formula (I.3) wherein $(R_5)_S$ is 4-tert-butyl and the substituent A—$R_7$ corresponds in each case to a line of Table A.

Table 324: Compounds of general formula (I.3) wherein $(R_5)_S$ is 4-CN and the substituent A—$R_7$ corresponds in each case to a line of Table A.

Table 3-25: Compounds of general formula (I.3) wherein $(R_5)_S$ is 4-O—$CH_3$ and the substituent A—$R_7$ corresponds in each case to a line of Table A.

Table 3-26: Compounds of general formula (I.3) wherein $(R_5)_S$ is 2,4-$F_2$ and the substituent A—$R_7$ corresponds in each case to a line of Table A.

Compound of formula (I.3) wherein A—$R_7$ is ethyl and $(R_5)_S$ is 4-chlorine: m.p.: 81–83° C. (compound 3-4.2).

Compounds of Formula

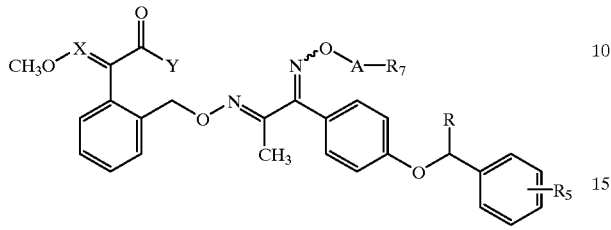

(I.A)

The figures given in the column "Phys. data" denote melting points in ° C.

| X | Y | A$R_7$ | R | $R_5$ | Phys. data |
|---|---|---|---|---|---|
| CH | O—CH$_3$ | CH$_3$ | CH$_3$ | 4-Cl | 128–130 |
| CH | O—CH$_3$ | CH$_3$ | CH$_3$ | 4-CF$_3$ | 116–118 |
| CH | O—CH$_3$ | CH$_2$CH$_3$ | CH$_3$ | 4-CF$_3$ | 98–100 |
| CH | O—CH$_3$ | CH$_3$ | CH$_2$CH$_3$ | 4-Cl | 105–107 |
| CH | O—CH$_3$ | CH$_2$CH$_3$ | CH$_2$CH$_3$ | 4-F | resin |
| CH | O—CH$_3$ | CH$_2$CH$_3$ | CH$_2$CH$_3$ | 4-Cl | 89–91 |
| CH | O—CH$_3$ | CH$_3$ | CH$_2$CH$_3$ | 4-F | 101–103 |
| CH | O—CH$_3$ | CH$_3$ | CH$_2$CH$_3$ | 4-tert-butyl | 101–102 |
| CH | O—CH$_3$ | CH$_3$ | CH$_2$CH$_3$ | 4-CF$_3$ | 124–126 |
| CH | O—CH$_3$ | CH$_2$CH$_3$ | CH$_2$CH$_3$ | 4-CF$_3$ | 112–114 |
| N | O—CH$_3$ | CH$_3$ | CH$_3$ | 4-Cl | 121–123 |
| N | O—CH$_3$ | CH$_3$ | CH$_3$ | 4-CF$_3$ | 116–118 |
| N | O—CH$_3$ | CH$_2$CH$_3$ | CH$_3$ | 4-CF$_3$ | 112–114 |
| N | O—CH$_3$ | CH$_3$ | CH$_2$CH$_3$ | 4-Cl | 100–102 |
| N | O—CH$_3$ | CH$_2$CH$_3$ | CH$_2$CH$_3$ | 4-F | 102–104 |
| N | O—CH$_3$ | CH$_2$CH$_3$ | CH$_2$CH$_3$ | 4-Cl | 103–105 |
| N | O—CH$_3$ | CH$_3$ | CH$_2$CH$_3$ | 4-F | 116–118 |
| N | O—CH$_3$ | CH$_2$CH$_3$ | CH$_2$CH$_3$ | 4-tert-butyl | resin |
| N | O—CH$_3$ | CH$_3$ | CH$_2$CH$_3$ | 4-tert-butyl | 106–107 |
| N | O—CH$_3$ | CH$_3$ | CH$_2$CH$_3$ | 4-CF$_3$ | 114–116 |
| N | O—CH$_3$ | CH$_2$CH$_3$ | CH$_2$CH$_3$ | 4-CF$_3$ | 72–74 |
| N | NHCH$_3$ | CH$_3$ | CH$_3$ | 4-Cl | 146–148 |
| N | NHCH$_3$ | CH$_3$ | CH$_3$ | 4-CF$_3$ | 130–132 |
| N | NHCH$_3$ | CH$_2$CH$_3$ | CH$_3$ | 4-CF$_3$ | 148–150 |
| N | NHCH$_3$ | CH$_3$ | CH$_2$CH$_3$ | 4-Cl | 139–141 |
| N | NHCH$_3$ | CH$_2$CH$_3$ | CH$_2$CH$_3$ | 4-F | 112–114 |
| N | NHCH$_3$ | CH$_2$CH$_3$ | CH$_2$CH$_3$ | 4-Cl | 131–133 |
| N | NHCH$_3$ | CH$_3$ | CH$_2$CH$_3$ | 4-F | 124–126 |
| N | NHCH$_3$ | CH$_3$ | CH$_2$CH$_3$ | 4-CF$_3$ | 149–151 |
| N | NHCH$_3$ | CH$_2$CH$_3$ | CH$_2$CH$_3$ | 4-CF$_3$ | 134–136 |

Example P3: Preparation of 2-[2-(2-{4-[2-(4-chlorophenyl-2-methoxyimino-ethoxy]-phenyl}-2-ethoxyimino-1-methyl-ethylideneaminooxymethyl)-phenyl]-3-methoxy-acrylic acid methyl ester of the formula

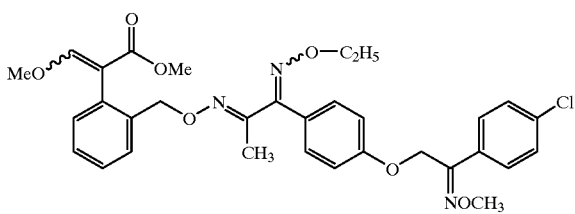

a) 4-Chlorophenacyl bromide O-methyloxime 50.3 g of 4-chlorophenacyl bromide in 300 ml of glacial acetic acid are stirred with 23 g of sodium acetate and 21.6 g O-methylhydroxylamine hydrochloride for 2 hours at 70° C. 150 ml of ethyl acetate are added to the mixture, which is then extracted by washing several times with water and saturated sodium chloride solution. The organic phase is dried over sodium sulfate and concentrated by evaporation in vacuo. Crystallisation from hexane yields 4-chlorophenacyl bromide O-methyloxime having a melting point of 57 to 60° C.

b) Compound of the formula

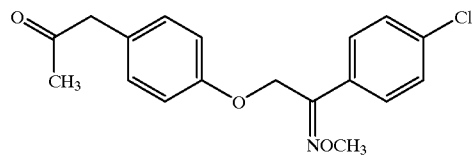

19.7 g of 1-(4-hydroxyphenyl)-propan-2-one, 34.4 g of 4-chlorophenacyl bromide O-methyloxime and 36 g of potassium carbonate are stirred in 200 ml of dimethylformamide for 2 hours at 80° C. 200 ml of ethyl acetate are added to the reaction mixture, which is then washed several times with water and saturated sodium chloride solution, dried over sodium sulfate and concentrated by evaporation in vacuo. The crude product is chromatographed on silica gel using tert-butyl methyl ether/hexane (1:19) to yield the title compound in the form of an oil.

c) Compound of the formula

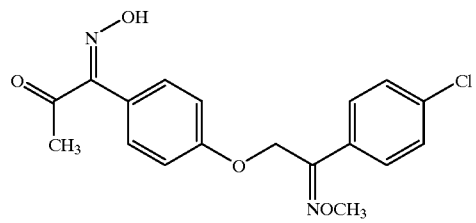

35 g of a compound obtainable according to process P3b) are placed in 200 ml of methanol and 18 ml of isopentyl nitrite. At 0° C., 30 ml of a 30% solution of sodium methanolate in methanol are added dropwise and the mixture is stirred for 2 hours at room temperature. The solvent is evaporated off, and 200 ml of ethyl acetate and 200 ml of water are added; the aqueous phase is separated off and the organic phase is then washed several times with water. Evaporating off the solvent and recrystallisation of the residue from dichloromethane/hexane yield the title product having a melting point of 131–133° C.

d) 1-{4-[2-(4-Chlorophenyl)-2-methoxyimino-ethoxy]-phenyl}-propane-1,2-dione 1-(O-ethyloxime) of the formula

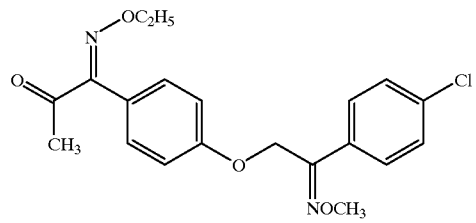

16.7 g of a compound obtainable according to process P3c) are stirred together with 5 ml of ethyl bromide and 10 g of potassium carbonate in 150 ml of dimethylformamide for 2 hours at room temperature. 300 ml of diethyl ether are added to the reaction mixture, which is then washed several times with water and saturated sodium chloride solution and the ether phase is concentrated to dryness by evaporation. Recrystallisation of the residue from diethyl ether/hexane yields the title product having a melting point of 76–81° C.

e) 1-{4-[2-(4-Chlorophenyl)-2-methoxyimino-ethoxy]-phenyl}-propane-1,2-dione 1-(O-ethyloxime) 2-oxime of the formula

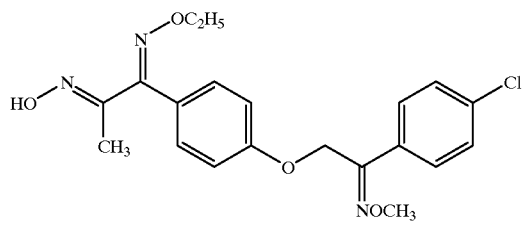

14.5 g of a compound obtainable according to process P3d) are stirred together with 3.1 g of hydroxylammonium chloride in 50 ml of pyridine for a period of 2 hours at 70° C. The reaction mixture is concentrated and 200 ml of ethyl acetate are added; the mixture is washed several times with water and saturated sodium chloride solution and the organic phase is concentrated to dryness by evaporation. Recrystallisation of the residue from dichloromethane/hexane yields the title product having a melting point of 136–137° C.

f) 2-[2-(2-{4-[2-(4-Chlorophenyl)-2-methoxyimino-ethoxy]-phenyl}-2-ethoxyimino-1-methylethylideneaminooxymethyl)-phenyl]-3-methoxy-acrylic acid methyl ester 2.9 g of a compound obtainable according to process P3e) in 30 ml of dimethylformamide are combined with 0.34 g of sodium hydride under an argon atmosphere. After evolution of hydrogen has ceased, 2 g of 2-(bromomethyl)-(methoxymethylene)-phenylacetic acid methyl ester are added and the mixture is stirred for one hour at room temperature. The mixture is rendered acidic with acetic acid and 150 ml of ethyl acetate are added; the mixture is washed several times with water and saturated sodium chloride solution and dried over sodium sulfate; the solvent is evaporated off. Chromatography of the residue on silica gel using tert-butyl methyl ether/hexane (1:9) yields the title compound in the form of a resin (compound 4-1.7).

Example P4: It is also possible to prepare the other compounds listed in Table 4 in a manner analogous to that described in Example P3. The figures given in the column "Phys. data" denote melting points in ° C.

TABLE 4-1

Compounds of general formula (I.4.1)

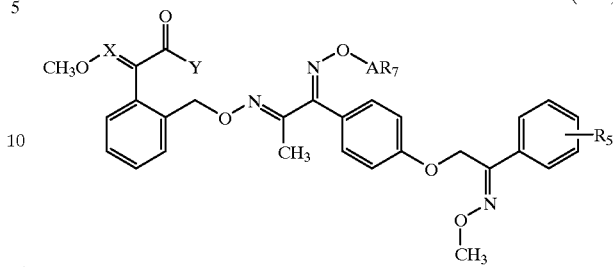

| Compd. | X | Y | AR$_7$ | R$_5$ | Phys. data |
|---|---|---|---|---|---|
| 4-1.1 | CH | OCH$_3$ | CH$_2$CH$_3$ | 4-F | resin |
| 4-1.2 | N | O—CH$_3$ | CH$_2$CH$_3$ | 4-F | resin |
| 4-1.3 | N | NH—CH$_3$ | CH$_2$CH$_3$ | 4-F | 87–89 |
| 4-1.4 | CH | OCH$_3$ | CH$_3$ | 4-F | foam |
| 4-1.5 | N | O—CH$_3$ | CH$_3$ | 4-F | resin |
| 4-1.6 | N | NH—CH$_3$ | CH$_3$ | 4-F | 106–108 |
| 4-1.7 | CH | OCH$_3$ | CH$_2$CH$_3$ | 4-Cl | resin |
| 4-1.8 | N | O—CH$_3$ | CH$_2$CH$_3$ | 4-Cl | resin |
| 4-1.9 | N | NH—CH$_3$ | CH$_2$CH$_3$ | 4-Cl | 108–111 |
| 4-1.10 | CH | OCH$_3$ | CH$_3$ | 4-Cl | resin |
| 4-1.11 | N | O—CH$_3$ | CH$_3$ | 4-Cl | resin |
| 4-1.12 | N | NH—CH$_3$ | CH$_3$ | 4-Cl | 104–107 |
| 4-1.13 | CH | OCH$_3$ | CH$_2$CH$_3$ | 4-CF$_3$ | oil |
| 4-1.14 | N | O—CH$_3$ | CH$_2$CH$_3$ | 4-CF$_3$ | 106–109 |
| 4-1.15 | N | NH—CH$_3$ | CH$_2$CH$_3$ | 4-CF$_3$ | 116–118 |
| 4-1.16 | CH | OCH$_3$ | CH$_3$ | 4-CF$_3$ | resin |
| 4-1.17 | N | O—CH$_3$ | CH$_3$ | 4-CF$_3$ | resin |
| 4-1.18 | N | NH—CH$_3$ | CH$_3$ | 4-CF$_3$ | 126–129 |
| 4-1.19 | CH | OCH$_3$ | CH$_2$CH$_3$ | H | resin |
| 4-1.20 | N | O—CH$_3$ | CH$_2$CH$_3$ | H | resin |
| 4-1.21 | N | NH—CH$_3$ | CH$_2$CH$_3$ | H | 124–126 |
| 4-1.22 | CH | OCH$_3$ | CH$_3$ | H | resin |
| 4-1.23 | N | O—CH$_3$ | CH$_3$ | H | resin |
| 4-1.24 | N | NH—CH$_3$ | CH$_3$ | H | 116–119 |
| 4-1.25 | CH | OCH$_3$ | CH$_3$ | 4-CH$_3$ | resin |
| 4-1.26 | N | O—CH$_3$ | CH$_3$ | 4-CH$_3$ | resin |
| 4-1.27 | N | NH—CH$_3$ | CH$_3$ | 4-CH$_3$ | 92–96 |
| 4-1.28 | CH | OCH$_3$ | CH$_2$CH$_3$ | 4-CH$_3$ | resin |
| 4-1.29 | N | O—CH$_3$ | CH$_2$CH$_3$ | 4-CH$_3$ | resin |
| 4-1.30 | N | NH—CH$_3$ | CH$_2$CH$_3$ | 4-CH$_3$ | 117–119 |
| 4-1.31 | CH | OCH$_3$ | CH$_2$—C≡CH | 4-CH$_3$ | resin |
| 4-1.32 | N | O—CH$_3$ | CH$_2$—C≡CH | 4-CH$_3$ | resin |
| 4-1.33 | N | NH—CH$_3$ | CH$_2$—C≡CH | 4-CH$_3$ | 103–105 |

TABLE 4-2

Compounds of formula (I.4.2)

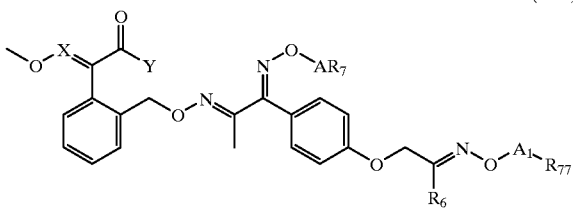

| No. | X | Y | R$_6$ | AR$_7$ | A$_1$R$_{77}$ | Phys. data |
|---|---|---|---|---|---|---|
| 4-2.1 | CH | OCH$_3$ | CH$_3$ | C$_2$H$_5$ | CH$_3$ | oil |
| 4-2.2 | N | OCH$_3$ | CH$_3$ | C$_2$H$_5$ | CH$_3$ | oil |
| 4-2.3 | N | NHCH$_3$ | CH$_3$ | C$_2$H$_5$ | CH$_3$ | 121–123 |
| 4-2.4 | CH | OCH$_3$ | p-tolyl | CH$_3$ | benzyl | 123–125 |
| 4-2.5 | N | OCH$_3$ | p-tolyl | CH$_3$ | benzyl | resin |
| 4-2.6 | N | NHCH$_3$ | p-tolyl | CH$_3$ | benzyl | 129–132 |

TABLE 4-2-continued

Compounds of formula (I.4.2)

| No. | X | Y | $R_6$ | $AR_7$ | $A_1R_{77}$ | Phys. data |
|---|---|---|---|---|---|---|
| 4-2.7 | CH | $OCH_3$ | $CH_3$ | $C_2H_5$ | benzyl | oil |
| 4-2.8 | N | $OCH_3$ | $CH_3$ | $C_2H_5$ | benzyl | oil |
| 4-2.9 | N | $NHCH_3$ | $CH_3$ | $C_2H_5$ | benzyl | resin |
| 4-2.10 | CH | $OCH_3$ | $CH_3$ | $CH_3$ | benzyl | oil |
| 4-2.11 | N | $OCH_3$ | $CH_3$ | $CH_3$ | benzyl | oil |
| 4-2.12 | N | $NHCH_3$ | $CH_3$ | $CH_3$ | benzyl | 83–85 |
| 4-2.13 | CH | $OCH_3$ | $CH_3$ | $CH_2C\equiv CH$ | benzyl | oil |
| 4-2.14 | N | $OCH_3$ | $CH_3$ | $CH_2C\equiv CH$ | benzyl | oil |
| 4-2.15 | N | $NHCH_3$ | $CH_3$ | $CH_2C\equiv CH$ | benzyl | resin |
| 4-2.16 | N | $OCH_3$ | $CH_3$ | $C_2H_5$ | 4-$CF_3$-benzyl | oil |

Example P5-1: 2-[[[(1-Methyl-2-(4-[{dimethyl-(4-fluorophenyl)-silyl}methoxy]phenyl)-[ethoxyimino]ethylidene)amino]oxy]methyl]-α-(methoxyimino)-phenylacetic acid methyl ester and 2-[[[(1-methyl-2-(4-[{dimethyl-(4-fluorophenyl)-silyl}methoxy]phenyl)-[ethoxyimino]ethyidene) amino]oxy]methyl]-α-(methoxyimino)-phenylacetic acid methylamide a) Chloromethyl-dimethyl-(4-fluorophenyl)-silane 250 ml of n-butyl lithium (1.6M in hexane) are added to 39 ml of 4-bromo-fluoro-benzene in 400 ml of tetrahydrofuran within a period of 45 minutes with stirring at −70° C. The mixture is stirred for a further 30 minutes and then 53 ml of chloromethyl-dimethyl-chlorosilane dissolved in 50 ml of tetrahydrofuran are added dropwise. The mixture is stirred at −70° C. for a further 30 minutes and the temperature of the reaction mixture is then allowed to rise to 0° C. The reaction mixture is poured onto 200 ml of ice, and 300 ml of diethyl ether are added; the mixture is washed with water and saturated sodium chloride solution and dried over sodium sulfate; the solvent is evaporated off in vacuo. Distillation of the residue at 97–105° C. (21 mbar) yields the title product.

b) 1-(4-[{Dimethyl-(4-fluorophenyl)-silyl}methoxy]phenyl)-propan-2-one 30 g of 1-(4-hydroxyphenyl)-propan-2-one and 45.5 g of chloromethyl-dimethyl-(4-fluorophenyl)-silane in 400 ml of dimethyl sulfoxide are stirred with 42 g of potassium carbonate and 2 g of potassium iodide for 12 hours at 70° C. The reaction mixture is poured into 1.6 liters of ice water and 500 ml of diethyl ether are added; the ether phase is extracted by washing several times with water and saturated sodium chloride solution and dried over sodium sulfate; the solvent is evaporated off. Distillation at 150° C. (0.01 mbar) yields the title product.

c) 1-(4-[{Dimethyl-(4-fluorophenyl)-silyl}methoxy]phenyl)propane-1,2-dione-1-oxime 28 ml of a 30% solution of sodium methanolate in methanol are added at room temperature to 31.6 g of 1-(4-[{dimethyl-(4-fluorophenyl)-silyl}methoxy]phenyl)-propan-2-one in 300 ml of methanol, and 27 ml of isopentyl nitrite are then added dropwise. The reaction mixture is stirred for a further hour and rendered neutral with acetic acid; the solvent is evaporated off in vacuo. 200 ml of ethyl acetate are added to the residue; the organic phase is washed with water and saturated sodium chloride solution and dried over sodium sulfate; the solvent is evaporated off in vacuo. Recrystallisation from diethyl ether/hexane yields the title product having a melting point of 115–117° C.

d) 1-(4-[{Dimethyl-(4-fluorophenyl)silyl}methoxy]phenyl)propane-1,2-dione-1-ethyloxime 13.8 g of 1-(4-[{dimethyl-(4-fluorophenyl)-silyl}methoxy]phenyl)-propane-1,2-dione-1-oxime, 4 ml of ethyl bromide and 9 g of potassium carbonate are stirred in 150 ml of dimethylformamide for 2 hours at room temperature. 200 ml of diethyl ether are added to the reaction mixture, which is then washed with water and saturated sodium chloride solution; the organic phase is dried and the solvent is evaporated off to yield the title product in the form of an oil.

e) 1-(4-[{Dimethyl-(4-fluorophenyl)-silyl}methoxy]phenyl)-propane-1,2-dione-1-ethyloxime-2-oxime 14.3 g of 1-(4-[{dimethyl-(4-fluorophenyl)-silyl}methoxy]phenyl)-propane-1,2-dione-1-ethyl-oxime in 50 ml of pyridine are stirred with 3.5 g of hydroxylammonium chloride for 2 hours at 70° C. The reaction mixture is concentrated in vacuo and ethyl acetate is added to the residue; the organic phase is washed with water and saturated sodium chloride solution and dried over sodium sulfate; the solvent is evaporated off. Recrystallisation from hexane yields the title product having a melting point of 100–102° C.

f) 2-[[[(1-Methyl-2-(4-[{dimethyl-(4-fluorophenyl)-silyl}methoxy]phenyl)-[ethoimino]-ethylidene) amino]oxy]methyl]-α-(methoxyimino)-phenylacetic acid methyl ester 3.9 g of 1-(4-[{dimethyl-(4-fluorophenyl)-silyl}methoxy]phenyl-propane-1,2-dione-1-ethyloxime-2-oxime are added at room temperature to 0.31 g of sodium hydride in 60 ml of dimethylformamide. After evolution of hydrogen has ceased, 2.9 g of 2-(bromomethyl)-α-(methoxyimino)-phenylacetic acid methyl ester are added and stirring is carried out for 1 hour at room temperature. The mixture is rendered neutral with acetic acid and 100 ml of ethyl acetate are added; the mixture is washed with water and saturated sodium chloride solution and dried over sodium sulfate; the solvent is evaporated off. Chromatography on silica gel using tert-butyl methyl ether/hexane (1:3) yields the title product in the form of an oil (compound 5.22).

g) 2-[[[(1-Methyl-2-(4-[{dimethyl-(4-fluorophenyl)-silyl}methoxy]phenyl)-[ethoxyimino]-ethylidene)amino]oxy]methyl]-α-(methoxyimino)-phenylacetic acid methylamide 3 ml of a 8M solution of methylamine in ethanol are added to 2.9 g of 2-[[[(1-methyl-2-(4-[{dimethyl-(4-fluorophenyl)-silyl}methoxy]phenyl)-[ethoxyimino]ethylidene) amino]oxy]-methyl]-α-(methoxyimino)-phenylacetic acid methyl ester in 30 ml of methanol and stirring is carried out for 2 days at room temperature. The reaction mixture is concentrated to dryness by evaporation. Recrystallisation of the residue from hexane yields the title compound having a melting point of 88-90° C. (compound 5.23).

Example P5-2: It is also possible to prepare the other compounds listed in Table 5 in a manner analogous to that described in Example P51. The figures given in the column "Phys. data" denote melting points in ° C.

TABLE 5

Compounds of general formula

| Compd. | X | Y | AR$_7$ | R$_5$ | Phys. data |
|---|---|---|---|---|---|
| 5.1 | CH | OCH$_3$ | CH$_3$ | H | oil |
| 5.2 | N | OCH$_3$ | CH$_3$ | H | oil |
| 5.3 | N | NH—CH$_3$ | CH$_3$ | H | 128–130 |
| 5.4 | CH | OCH$_3$ | CH$_2$CH$_3$ | H | oil |
| 5.5 | N | OCH$_3$ | CH$_2$CH$_3$ | H | oil |
| 5.6 | N | NH—CH$_3$ | CH$_2$CH$_3$ | H | oil |
| 5.7 | CH | OCH$_3$ | CH$_2$CH$_3$ | 3-CF$_3$ | oil |
| 5.8 | N | OCH$_3$ | CH$_2$CH$_3$ | 3-CF$_3$ | oil |
| 5.9 | CH | OCH$_3$ | CH$_3$ | 3-CF$_3$ | oil |
| 5.10 | N | OCH$_3$ | CH$_3$ | 3-CF$_3$ | oil |
| 5.11 | N | NH—CH$_3$ | CH$_3$ | 3-CF$_3$ | resin |
| 5.12 | CH | OCH$_3$ | CH$_2$CH$_3$ | 4-CF$_3$ | resin |
| 5.13 | N | OCH$_3$ | CH$_2$CH$_3$ | 4-CF$_3$ | 85–87 |
| 5.14 | N | NH—CH$_3$ | CH$_2$CH$_3$ | 4-CF$_3$ | 129–131 |
| 5.15 | CH | OCH$_3$ | CH$_2$CH$_3$ | 4-Cl | oil |
| 5.16 | N | OCH$_3$ | CH$_2$CH$_3$ | 4-Cl | oil |
| 5.17 | N | NH—CH$_3$ | CH$_2$CH$_3$ | 4-Cl | 108–110 |
| 5.18 | CH | OCH$_3$ | CH$_3$ | 4-Cl | oil |
| 5.19 | N | OCH$_3$ | CH$_3$ | 4-Cl | oil |
| 5.20 | N | NH—CH$_3$ | CH$_3$ | 4-Cl | 99–101 |
| 5.21 | CH | OCH$_3$ | CH$_2$CH$_3$ | 4-F | resin |
| 5.22 | N | OCH$_3$ | CH$_2$CH$_3$ | 4-F | resin |
| 5.23 | N | NH—CH$_3$ | CH$_2$CH$_3$ | 4-F | 88–90 |
| 5.24 | CH | OCH$_3$ | CH$_3$ | 4-F | 101–103 |
| 5.25 | N | OCH$_3$ | CH$_3$ | 4-F | 75–77 |
| 5.26 | N | NH—CH$_3$ | CH$_3$ | 4-F | 100–102 |
| 5.27 | CH | OCH$_3$ | CH$_2$CH$_3$ | 2-F | oil |
| 5.28 | N | OCH$_3$ | CH$_2$CH$_3$ | 2-F | oil |
| 5.29 | N | NH—CH$_3$ | CH$_2$CH$_3$ | 2-F | 75–79 |
| 5.30 | CH | OCH$_3$ | CH$_2$CH$_3$ | 2-CH$_3$ | oil |
| 5.31 | N | OCH$_3$ | CH$_2$CH$_3$ | 2-CH$_3$ | 77–80 |
| 5.32 | N | NH—CH$_3$ | CH$_2$CH$_3$ | 2-CH$_3$ | 125–127 |
| 5.33 | CH | OCH$_3$ | CH$_3$ | 2-CH$_3$ | oil |
| 5.34 | N | OCH$_3$ | CH$_3$ | 2-CH$_3$ | oil |
| 5.35 | N | NH—CH$_3$ | CH$_3$ | 2-CH$_3$ | 81–84 |
| 5.36 | CH | OCH$_3$ | CH$_2$—C≡CH | 2-CH$_3$ | resin |
| 5.37 | N | OCH$_3$ | CH$_2$—C≡CH | 2-CH$_3$ | 85–87 |
| 5.38 | N | NH—CH$_3$ | CH$_2$—C≡CH | 2-CH$_3$ | 99–102 |
| 5.39 | CH | OCH$_3$ | CH$_3$ | 3-CH$_3$ | |
| 5.40 | N | OCH$_3$ | CH$_2$CH$_3$ | 3-F | |
| 5.41 | N | NH—CH$_3$ | CH$_3$ | 3-F | |
| 5.42 | CH | OCH$_3$ | CH$_3$ | 3-OCF$_3$ | |
| 5.43 | N | OCH$_3$ | CH$_3$ | 4-O—CF$_3$ | |
| 5.44 | N | NH—CH$_3$ | CH$_3$ | 2-OCF$_3$ | |
| 5.45 | CH | OCH$_3$ | CH$_2$CH$_3$ | 3-OCF$_3$ | |
| 5.46 | N | OCH$_3$ | CH$_2$CH$_3$ | 4-O—CF$_3$ | |
| 5.47 | N | NH—CH$_3$ | CH$_2$CH$_3$ | 2-OCF$_3$ | |

Example P6-1: 2-[[[(1-Methyl-2-(4-{2-(3-methylphenyl)-ethanedione}-phenyl)-[methoxyimino]ethylidene)amino]oxy]methyl]-α-(methoxyimino)-phenylacetic acid methylamide 2.2 g of 2-[[[(1-methyl-2-(4-(3-methylphenyl-ethynyl)-phenyl)-2-E-[ethoxyimino]ethylidene)amino]oxy]methyl]-α-(methoxyimino)-phenylacetic acid methylamide in 12 ml of dimethyl sulfoxide are stirred with 0.7 g of iodine for a period of 6 hours at 150° C. After cooling, the reaction mixture is purified on silica gel using ether/hexane (3:1), yielding the title compound in the form of a resin (compound 6.3).

Example P6-2: It is also possible to prepare the other compounds listed in Table 6 in a manner analogous to that described in Example P6-1. The figures given in the column "Phys. data" denote melting points in ° C.

TABLE 6

Compounds of general formula (I.6)

| Compd. | X | Y | AR$_7$ | R$_5$ | Phys. data |
|---|---|---|---|---|---|
| 6.1 | CH | OCH$_3$ | CH$_3$ | 2-CH$_3$ | |
| 6.2 | N | O—CH$_3$ | CH$_3$ | 4-CH$_3$ | |
| 6.3 | N | NH—CH$_3$ | CH$_3$ | 3-CH$_3$ | resin |
| 6.4 | CH | OCH$_3$ | CH$_2$CH$_3$ | 2-Cl | |
| 6.5 | N | O—CH$_3$ | CH$_2$CH$_3$ | 4-Cl | |
| 6.6 | N | NH—CH$_3$ | CH$_2$CH$_3$ | 3-Cl | |
| 6.7 | CH | OCH$_3$ | CH$_2$CH$_3$ | 2-F | |
| 6.8 | N | O—CH$_3$ | CH$_2$CH$_3$ | 4-F | |
| 6.9 | CH | OCH$_3$ | CH$_3$ | 3-F | |
| 6.10 | N | O—CH$_3$ | CH$_3$ | 2-CF$_3$ | |
| 6.11 | N | NH—CH$_3$ | CH$_3$ | 4-CF$_3$ | |
| 6.12 | CH | OCH$_3$ | CH$_2$CH$_3$ | 3-CF$_3$ | |
| 6.13 | N | O—CH$_3$ | CH$_2$CH$_3$ | 2-OCF$_3$ | |
| 6.14 | N | NH—CH$_3$ | CH$_2$CH$_3$ | 4-OCF$_3$ | |
| 6.15 | CH | OCH$_3$ | CH$_2$CH$_3$ | 3-OCF$_3$ | |

Example P7-1: 2-[[[(1-Methyl-2-(4-{3-(3-trifluoromethylphenyl)-prop-2-yn-1-yl-oxy}-phenyl)-[methoxyimino]ethylidene)amino]oxy]methyl]-α-(methoxymethylene)-phenylacetic acid methyl ester 1.5 ml of 3-iodobenzotrifluoride and 0.1 g of bis(triphenylphosphine)palladium(II) chloride are added to a solution of 2.2 g of 2-[[[(1-methyl-2-({4-propargyloxy}-phenyl)-[methoxyimino]ethylidene)amino]oxy]methyl]-α-(methoxymethylene)-phenylacetic acid methyl ester in 100 ml of triethylamine and 40 ml of tetrahydrofuran. The mixture is stirred for 3 hours at 60° C. and filtered, and the filtrate is concentrated by evaporation. The residue is purified on silica gel using ethyl acetate/hexane (1:2) to yield the title compound in the form of a resin (compound 7.10).

Example P7-2: It is also possible to prepare the other compounds listed in Table 7 in a manner analogous to that described in Example P7-1. The figures given in the column "Phys. data" denote melting points in ° C.

TABLE 7

Compounds of general formula (I.7)

| Compd. | X | Y | AR$_7$ | R$_5$ | Phys. data |
|---|---|---|---|---|---|
| 7.1 | CH | OCH$_3$ | CH$_3$ | 2-CH$_3$ | |
| 7.2 | N | O—CH$_3$ | CH$_3$ | 4-CH$_3$ | |
| 7.3 | N | NH—CH$_3$ | CH$_3$ | 3-CH$_3$ | |

TABLE 7-continued

Compounds of general formula (I.7)

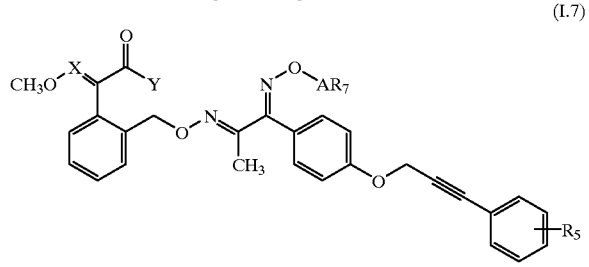

| Compd. | X | Y | AR7 | R5 | Phys. data |
|---|---|---|---|---|---|
| 7.4 | CH | OCH3 | CH2CH3 | 2-Cl | |
| 7.5 | N | O—CH3 | CH2CH3 | 4-Cl | |
| 7.6 | N | NH—CH3 | CH2CH3 | 3-Cl | |
| 7.7 | CH | OCH3 | CH2CH3 | 2-F | |
| 7.8 | N | O—CH3 | CH2CH3 | 4-F | |
| 7.9 | CH | OCH3 | CH3 | 3-F | |
| 7.10 | CH | O—CH3 | CH3 | 3-CF3 | resin |
| 7.11 | N | NH—CH3 | CH3 | 4-CF3 | |
| 7.12 | CH | OCH3 | CH2CH3 | 2-CF3 | |
| 7.13 | N | O—CH3 | CH2CH3 | 2-OCF3 | |
| 7.14 | N | NH—CH3 | CH2CH3 | 4-OCF3 | |
| 7.15 | CH | OCH3 | CH2CH3 | 3-OCF3 | |

Example P8-1: 2-[[[(1-Methyl-2-(4-{3-(3-trifluoromethylphenyl)-n-propyl-oxy}-phenyl)-[methoxyimino]ethylidene)amino]oxy]methyl]-α-(methoxymethylene)-phenylacetic acid methyl ester 100 mg of palladium on carbon (5% Pd) are added to 1.8 g of 2-[[[(1-methyl-2-(4-{3-(3-trifluoromethylphenyl)-propyn-2-yl-oxy}-phenyl-[methoxyimino]ethylidene)amino]oxy]-methyl]-α-(methoxymethylene)-phenylacetic acid methyl ester in 30 ml of tetrahydrofuran. Hydrogen is introduced at normal pressure until one equivalent has been used. The reaction mixture is then filtered and the filtrate is concentrated to dryness by evaporation. The residue is purified on silica gel using ethyl acetate/hexane (1:2) to yield the title compound in the form of an oil (compound 8.10).

Example P8-2: It is also possible to prepare the other compounds listed in Table 8 in a manner analogous to that described in Example P8-1.

TABLE 8

Compounds of general formula (I.8)

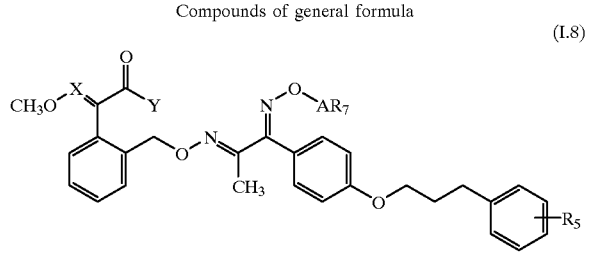

| Compd. | X | Y | AR7 | R5 | Phys. data |
|---|---|---|---|---|---|
| 8.1 | CH | OCH3 | CH3 | 2-CH3 | |
| 8.2 | N | O—CH3 | CH3 | 4-CH3 | |
| 8.3 | N | NH—CH3 | CH3 | 3-CH3 | |
| 8.4 | CH | OCH3 | CH2CH3 | 2-Cl | |
| 8.5 | N | O—CH3 | CH2CH3 | 4-Cl | |
| 8.6 | N | NH—CH3 | CH2CH3 | 3-Cl | |

TABLE 8-continued

Compounds of general formula (I.8)

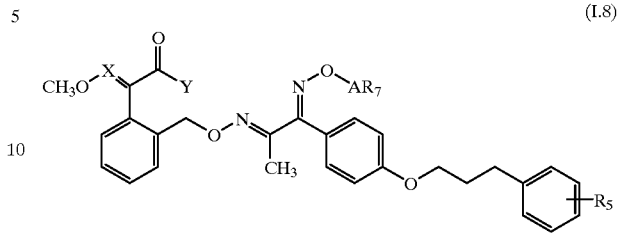

| Compd. | X | Y | AR7 | R5 | Phys. data |
|---|---|---|---|---|---|
| 8.7 | CH | OCH3 | CH2CH3 | 2-F | |
| 8.8 | N | O—CH3 | CH2CH3 | 4-F | |
| 8.9 | CH | OCH3 | CH3 | 3-F | |
| 8.10 | CH | O—CH3 | CH3 | 3-CF3 | oil |
| 8.11 | N | NH—CH3 | CH3 | 4-CF3 | |
| 8.12 | CH | OCH3 | CH2CH3 | 2-CF3 | |
| 8.13 | N | O—CH3 | CH2CH3 | 2-OCF3 | |
| 8.14 | N | NH—CH3 | CH2CH3 | 4-COF3 | |
| 8.15 | CH | OCH3 | CH2CH3 | 3-OCF3 | |

Example P9-1: Compound of the formula

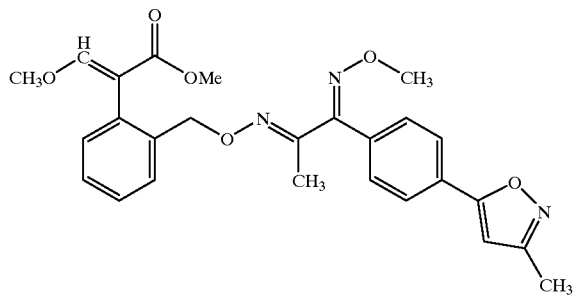

1.1 g of phenyl isocyanate, 0.45 ml of nitioethane and 0.5 ml of triethylamine are added to 2.1 g of 2-[[[(1-methyl-2-(4-ethynyl-phenyl)-[methoxyimino]ethylidene)amino]oxy] methyl]-α-(methoxymethylene)-phenylacetic acid methyl ester in 40 ml of toluene. Stirring is carried out for a period of 5 hours at 80° C., the reaction mixture is filtered and the filtrate is concentrated by evaporation. Purification on silica gel using ethyl acetate/hexane 1:2 yields the title product having a melting point of 116–118° C. (compound 9-1.1).

Example P9-2: Preparation of the compound of formula

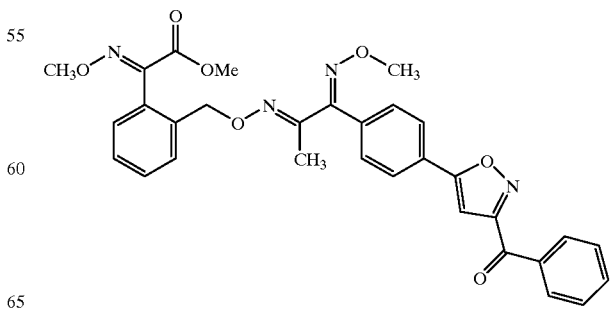

1.8 g of the compound of formula

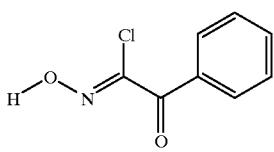

and 2 ml of triethylamine are added to 1.2 g of 2-[[[(1-methyl-2-(4-ethynyl-phenyl)-[methoxyimino]ethylidene)amino]oxy]methyl]-α-(methoxyimino)-phenylacetic acid methyl ester in toluene. Stirring is carried out for 4 hours at 65° C., the reaction mixture is filtered and the filtrate is concentrated by evaporation. Purification on silica gel using toluene/diisopropyl ether/hexane (1:1:2) yields the title compound having a melting point of 127–129° C. (compound 9-2.2).

Example P9-3: It is also possible to prepare the other compounds listed in Tables 9-1 and 9-2 in a manner analogous to that described in Examples P9-1 and P9-2. The figures given in the column "Phys. data" denote melting points in ° C.

TABLE 9-1

Compounds of general formula (I.9-1)

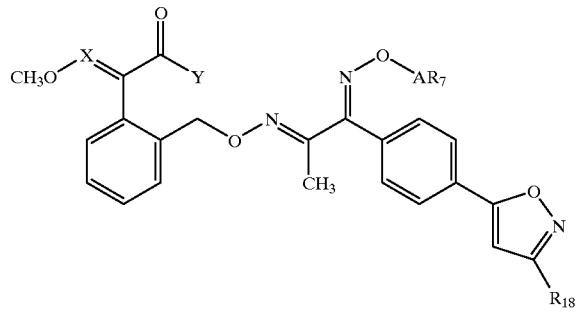

| Compd. | X | Y | AR$_7$ | R$_{18}$ | Phys. data |
|---|---|---|---|---|---|
| 9-1.1 | CH | OCH$_3$ | CH$_3$ | CH$_3$ | 116–118° C. |
| 9-1.2 | N | O—CH$_3$ | CH$_3$ | CH$_3$ | |
| 9-1.3 | N | NH—CH$_3$ | CH$_3$ | CH$_3$ | |
| 9-1.4 | CH | OCH$_3$ | CH$_2$CH$_3$ | CH$_3$ | |
| 9-1.5 | N | O—CH$_3$ | CH$_2$CH$_3$ | CH$_3$ | |
| 9-1.6 | N | NH—CH$_3$ | CH$_2$CH$_3$ | CH$_3$ | |
| 9-1.7 | CH | OCH$_3$ | CH$_2$CH$_3$ | CH$_2$CH$_3$ | |
| 9-1.8 | N | O—CH$_3$ | CH$_2$CH$_3$ | CH$_2$CH$_3$ | |
| 9-1.9 | CH | OCH$_3$ | CH$_3$ | CH$_2$CH$_3$ | |
| 9-1.10 | CH | O—CH$_3$ | CH$_3$ | CH$_2$CH$_3$ | |
| 9-1.11 | N | NH—CH$_3$ | CH$_3$ | —C$_6$H$_5$ | |
| 9-1.12 | CH | OCH$_3$ | CH$_3$ | —C$_6$H$_5$ | |
| 9-1.13 | N | O—CH$_3$ | CH$_3$ | —C$_6$H$_5$ | |
| 9-1.14 | N | O—CH$_3$ | CH$_2$CH$_3$ | —C$_6$H$_5$ | |
| 9-1.15 | N | NH—CH$_3$ | CH$_2$CH$_3$ | —C$_6$H$_5$ | |
| 9-1.16 | CH | OCH$_3$ | CH$_2$CH$_3$ | —C$_6$H$_5$ | |
| 9-1.17 | N | NH—CH$_3$ | CH$_3$ | —C$_6$H$_4$-3-CF$_3$ | |
| 9-1.18 | CH | OCH$_3$ | CH$_3$ | —C$_6$H$_4$-4-CF$_3$ | |
| 9-1.19 | N | O—CH$_3$ | CH$_3$ | —C$_6$H$_4$-3-Cl | |
| 9-1.20 | N | O—CH$_3$ | CH$_2$CH$_3$ | —C$_6$H$_4$-4-Cl | |
| 9-1.21 | N | NH—CH$_3$ | CH$_2$CH$_3$ | —C$_6$H$_4$-3-F | |
| 9-1.22 | CH | OCH$_3$ | CH$_2$CH$_3$ | —C$_6$H$_4$-4-F | |

TABLE 9-2

Compounds of general formula (I.9-2)

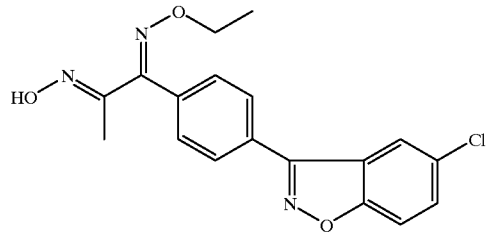

| Compd. | X | Y | AR$_7$ | R$_5$ | Phys. data |
|---|---|---|---|---|---|
| 9-2.1. | CH | OCH$_3$ | CH$_3$ | H | |
| 9-2.2. | N | O—CH$_3$ | CH$_3$ | H | 127–129 |
| 9-2.3. | N | NH—CH$_3$ | CH$_3$ | H | |
| 9-2.4. | CH | OCH$_3$ | CH$_2$CH$_3$ | H | |
| 9-2.5. | N | O—CH$_3$ | CH$_2$CH$_3$ | H | |
| 9-2.6. | N | NH—CH$_3$ | CH$_2$CH$_3$ | H | |
| 9-2.7. | CH | OCH$_3$ | CH$_3$ | 4-Cl | |
| 9-2.8. | N | O—CH$_3$ | CH$_3$ | 3-Cl | |
| 9-2.9. | N | NH—CH$_3$ | CH$_3$ | 2-Cl | |
| 9-2.10. | CH | OCH$_3$ | CH$_2$CH$_3$ | 4-CF$_3$ | |
| 9-2.11. | N | O—CH$_3$ | CH$_2$CH$_3$ | 3-CF$_3$ | |
| 9-2.12. | N | NH—CH$_3$ | CH$_2$CH$_3$ | 2-CF$_3$ | |
| 9-2.13. | CH | OCH$_3$ | CH$_3$ | 4-F | |
| 9-2.14. | N | O—CH$_3$ | CH$_3$ | 3-F | |
| 9-2.15. | N | NH—CH$_3$ | CH$_3$ | 2-F | |
| 9-2.16. | CH | OCH$_3$ | CH$_2$CH$_3$ | 4-OCF$_3$ | |
| 9-2.17. | N | O—CH$_3$ | CH$_2$CH$_3$ | 3-OCF$_3$ | |
| 9-2.18. | N | NH—CH$_3$ | CH$_2$CH$_3$ | 2-OCF$_3$ | |

Example P9-4: Preparation of 6-chloro-3-(4'-(1-ethoxyimino-2-hydroxyimino)propyl)benzisoxazole of the formula

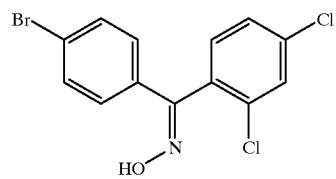

a) 4-Bromo-2',4'-dichlorobenzophenone oxime:

Hydroxylammonium chloride (6.4 g) and pyridine (7.2 g) are added at room temperature to a solution of 4-bromo-2', 4'-dichlorobenzophenone (15.1 g) in ethanol (75 ml). After being boiled for 10 hours under reflux, the reaction mixture is concentrated by evaporation using a rotary evaporator, and water and ethyl acetate are added to the residue. After washing the organic phase and evaporating the solution, a residue is obtained which is dissolved in hexane at 30° C. and left to stand at 5° C. The solid that forms is filtered off with suction and dried in air, thereby yielding the title compound having a melting point of 125–126° C.

b) 3-(4'-Bromophenyl)-6-chlorobenzisoxazole:

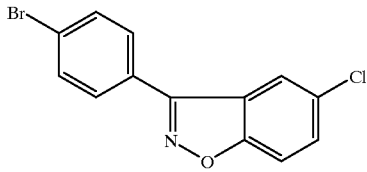

20 ml of dimethylformamide are added to 10.4 g of the compound obtainable according to a). At 30–35° C., KOH (5.63 g) is added in portions. The mixture is then stirred at 45° C. for 1 hour and then a further 0.94 g portion of KOH is added at 30° C. and the mixture is stirred for a further 1 hour at 45° C. to complete the reaction. Methanol (30 ml) and, after 10 minutes' stirring, water (120 ml) are added to the reaction mixture. After cooling to −5° C., the solid formed is filtered off and dried in air to yield the title compound having a melting point of 126–127° C.

c) 4-(6'-Chlorobenzoxazol-3'-yl)benzaldehyde:

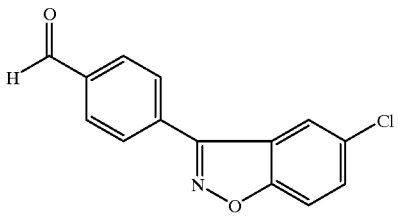

A solution of 3-(4'-bromophenyl)-6-chlorobenzoxazole (43.2 g) in tetrahydrofuran (470 ml) is cooled to −70° C. under argon. Within a period of one hour, an approx. 1.6M n-butyl lithium solution in hexane (100 ml) is added dropwise. After 1 hour at −70° C., the reaction mixture is brought to −45° C. and a solution of N-formylpiperidine (17.5 g) in tetrahydrofuran (145 ml) is added within a period of 30 minutes. The temperature is then allowed to rise to room temperature and the mixture is stirred for two hours. 2N hydrochloric acid (280 ml) is added and the mixture is stirred for a further 2 hours at room temperature. The reaction mixture is taken up in methylene chloride and washed with saturated NaHCO$_3$ solution and saturated NaCl solution. After evaporating off the solvent, the residue is stirred together with 200 ml of diethyl ether. Filtration yields the title compound having a melting point of 159–160° C.

d) 6Chloro-3-(4'-(2-nitropropenyl)phenyl)benzisoxazole

Ammonium acetate (12.0 g) is added to 4-(6'-chlorobenzoxazol-3'-yl)benzaldehyde (35.2 g) and nitroethane (160 ml). The mixture is then stirred for 4 hours under reflux. The reaction mixture is cooled to approx. 60° C. and at that temperature concentrated by evaporation in vacuo. The residue is taken up in ethyl acetate and washed with brine. Drying over Na$_2$SO$_4$ and evaporating off solvent at 50° C. yields a residue, which is stirred together with tert-butyl methyl ether. The solid product obtained is filtered off with suction and dried in air, yielding the title compound having a melting point of 160–162° C.

e) 6-Chloro-3-(4'-(2-oxopropyl)phenyl)benzisoxazole

Alcohol (30 ml) and water (29 ml) are added to 6-chloro+4'-(2-nitropropenyl)phenyl)benzisoxazole (18.2 g), iron granules (11.3 g) and iron(ill) chloride (0.18 g) and the mixture is heated to 70° C. with stirring. Once the temperature has reached 70° C., 20 ml of concentrated hydrochloric acid are added dropwise in such a manner that the reaction temperature can be maintained at 70° C. After the addition is complete, the batch is stirred at 70° C. for 90 minutes, a further 10 ml of concentrated hydrochloric acid are added dropwise and the stirring is continued for a further 2 hours. The reaction mixture is cooled, filtered over silica gel and diluted with ethyl acetate; the organic phase is extracted by shaking with water and saturated NaCl solution. After drying over MgSO$_4$ and evaporating off the solvent, a sticky residue is obtained, which is purified by means of column chromatography (ethyl acetate/hexane 1:5), yielding the title compound having a melting point of 109–110° C.

f) 6-Chloro-3-(4'-(1-hydroxyimino-2-oxo)propyl)benzisoxazole

Isopentyl nitrite (3.0 g) is slowly added dropwise at 20° C. to 7.2 g of 6-chloro-3-(4'-(2-oxo-propyl)phenyl)benzisoxazole in methanol (37 ml). After the addition of 30% sodium methanolate (5.7 g), stirring is carried out overnight at room temperature. The reaction mixture is concentrated by evaporation at 50° C.; the residue is dissolved in water and rendered acidic with 10% hydrochloric acid at 10° C. Ethyl acetate is added, the water phase separated and the organic phase washed with water. Drying over MgSO$_4$ and concentration by evaporation yield a solid, which is stirred together with hexane, filtered off with suction and dried in air to yield the title compound having a melting point of 224–226° C.

g) 6-Chloro-3-(4'-(1-ethoxyimino-2-oxo)propyl)benzisoxazole

Ethyl iodide (5.45 g) is added to 6chloror(4-(1-hydroxyimino-2-oxo)propyl)benzisoxazole (7.01 g), acetonitrile (44 ml) and potassium carbonate (4.3 g). The batch is heated for 3 hours under reflux, cooled to room temperature and filtered, the filter being rinsed with acetonitrile. The filtrate is concentrated by evaporation using a rotary evaporator; the residue is taken up in ethyl acetate and washed with water and brine. Drying of the organic phase over Na$_2$SO$_4$ and concentration by evaporation yield the title compound having a melting point of 106–107° C.

h) 6-Chloro-3-(4'-(1-ethoxymino-2-hydroxymino)propyl)benzisoxazole

Pyridine (3.6 g) is added to 6-chloro-3-(4'-(1-ethoxyimino-2-oxo)propyl)benzisoxazole (7.20 g), ethanol (37 ml) and hydroxylammonium chloride (3.2 g). The batch is boiled under reflux for 2 hours. The reaction mixture is evaporated; the residue is washed with water, taken up in ethyl acetate and then washed with water. After drying of the organic phase over Mg$_2$SO$_4$ and concentration using a rotary evaporator, the residue is stirred when cold together with a little diethyl ether. The resulting solid product is filtered off with suction and dried in air to yield the title compound having a melting point of 218–21 9° C.

Starting from the compounds according to Examples P9-4/g) and P9-4/h), compounds 9-3.1 to 9-3.3 can be prepared analogously to the process variants a1), a2) and b).

Example P9-5: It is also possible to prepare the intermediates required for the other compounds listed in Table 9-3 in a manner analogous to that described in Example P9-4. The figures given in the column "Phys. data" denote melting points in ° C.

TABLE 9-3

Compounds of the formula

[Structure: CH3O-X with C(=O)-Y group, phenyl-CH2-O-N=C(CH3)- linked to aryl with isoxazole ring bearing R5, OAR7]

| Compd. | X | Y | AR7 | R5 | Phys. data |
|---|---|---|---|---|---|
| 9-3.1 | CH | OCH₃ | CH₂CH₃ | 6-Cl | 105–110 |
| 9-3.2 | N | O—CH₃ | CH₂CH₃ | 6-Cl | 128–130 |
| 9-3.3 | N | NH—CH₃ | CH₂CH₃ | 6-Cl | 124–126 |
| 9-3.4 | CH | OCH₃ | CH₂CH₃ | 6-Cl | |
| 9-3.5 | N | O—CH₃ | CH₂CH₃ | 6-Cl | |
| 9-3.6 | N | NH—CH₃ | CH₂CH₃ | 6-Cl | |
| 9-3.7 | CH | OCH₃ | CH₂CH₃ | 5-Cl | |
| 9-3.8 | N | O—CH₃ | CH₂CH₃ | 5-Cl | |
| 9-3.9 | N | NH—CH₃ | CH₂CH₃ | 5-Cl | |
| 9-3.10 | CH | OCH₃ | CH₂CH₃ | 5,6-Cl₂ | |
| 9-3.11 | N | O—CH₃ | CH₂CH₃ | 5,6-Cl₂ | |
| 9-3.12 | N | NH—CH₃ | CH₂CH₃ | 5,6-Cl₂ | |
| 9-3.13 | CH | OCH₃ | CH₂CH₃ | 6-CF₃ | |
| 9-3.14 | N | O—CH₃ | CH₂CH₃ | 6-CF₃ | |
| 9-3.15 | N | NH—CH₃ | CH₂CH₃ | 6-CF₃ | |
| 9-3.16 | CH | OCH₃ | CH₂CH₃ | 6-OCF₃ | |
| 9-3.17 | N | O—CH₃ | CH₂CH₃ | 6-OCF₃ | |
| 9-3.18 | N | NH—CH₃ | CH₂CH₃ | 6-OCF₃ | |

Example P10-1: Preparation of

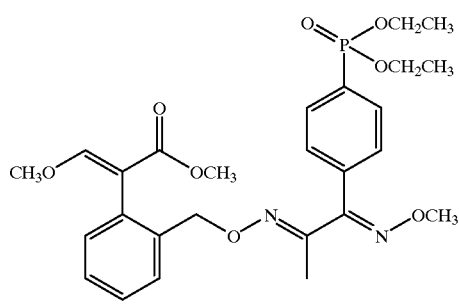

0.95 g of 2-{2-[2-(4-bromophenyl)-2-methoxyimino-1-methyl-ethylideneaminooxymethyl]-phenyl}-3-methoxyacrylic acid methyl ester, 0.4 g of triethylamine, 0.25 g of tetrakistriphenylphosphine-palladium(O), 3 ml of toluene and 0.28 g of diethyl phosphite are stirred under argon for 2 hours at 90° C. The reaction mixture is taken up in ethyl acetate, washed with water, dried and concentrated. Chromatography of the crude product on silica gel using ethyl acetatehexane (1:1) yields 0.93 g of product having a melting point of 125–126° C. (compound 10-1.16).

Example P11: It is also possible to prepare the other compounds listed in Tables 10 and 11 in a manner analogous to that described in Example P10-1.

TABLE B

Compounds of general formula (I.10)

[Structure of formula I.10]

| No. | X | Y | R₁₁ | R₁₂ | (W)w |
|---|---|---|---|---|---|
| B.1 | CH | OCH₃ | C₆H₅ | C₆H₅ | O |
| B.2 | N | OCH₃ | C₆H₅ | C₆H₅ | O |
| B.3 | N | NHCH₃ | C₆H₅ | C₆H₅ | O |
| B.4 | CH | OCH₃ | 4-Cl—C₆H₅ | 4-Cl—C₆H₅ | O |
| B.5 | N | OCH₃ | 4-Cl—C₆H₅ | 3-Cl—C₆H₅ | O |
| B.6 | N | NHCH₃ | 4-Cl—C₆H₅ | 2-Cl—C₆H₅ | O |
| B.7 | CH | OCH₃ | 2,4-Cl₂—C₆H₅ | 2,4-Cl₂—C₆H₅ | O |
| B.8 | N | OCH₃ | 2,4-Cl₂—C₆H₅ | 3,4-Cl₂—C₆H₅ | O |
| B.9 | N | NHCH₃ | 2,4-Cl₂—C₆H₅ | 2,5-Cl₂—C₆H₅ | O |
| B.10 | CH | OCH₃ | 3-CF₃—C₆H₅ | 3-CF₃—C₆H₅ | O |
| B.11 | N | OCH₃ | 4-CF₃—C₆H₅ | 4-CF₃—C₆H₅ | O |
| B.12 | CH | OCH₃ | C₆H₅O | C₆H₅O | O |
| B.13 | N | OCH₃ | C₆H₅O | C₆H₅O | O |
| B.14 | CH | OCH₃ | 3,5-Cl₂—C₆H₅O | 3,5-Cl₂—C₆H₅O | O |
| B.15 | CH | OCH₃ | CH₃O | CH₃O | O |
| B.16 | CH | OCH₃ | CH₃CH₂O | CH₃CH₂O | O |
| B.17 | N | NHCH₃ | CH₃O | CH₃O | O |
| B.18 | CH | OCH₃ | 4-Cl—C₆H₅O | 4-Cl—C₆H₅O | O |
| B.19 | N | NHCH₃ | 3,5-Cl₂—C₆H₅O | 3,5-Cl₂—C₆H₅O | O |
| B.20 | CH | OCH₃ | 4-Cl—C₆H₅S | 4-Cl—C₆H₅S | O |
| B.21 | N | NHCH₃ | 4-Br—C₆H₅S | 4-Br—C₆H₅S | O |
| B.22 | N | OCH₃ | CH₃CH₂S | CH₃CH₂S | S |
| B.23 | CH | OCH₃ | 4-Cl—C₆H₅S | 4-Cl—C₆H₅S | S |
| B.24 | N | OCH₃ | 4-Cl—C₆H₅S | 3,5-Cl₂—C₆H₅O | S |
| B.25 | N | NHCH₃ | CH₃CH₂S | 4-Cl—C₆H₅S | S |
| B.26 | CH | OCH₃ | CH₃CH₂O | 4-Cl—C₆H₅S | S |
| B.27 | N | OCH₃ | CH₃CH₂O | 4-Cl—C₆H₅S | S |
| B.28 | N | OCH₃ | 4-CF₃—C₆H₅ | CH₃CH₂S | O |
| B.29 | N | NHCH₃ | 4-CF₃—C₆H₅ | CH₃CH₂S | O |
| B.30 | CH | OCH₃ | 4-CF₃—C₆H₅ | CH₃S | S |
| B.31 | N | NHCH₃ | 4-CF₃—C₆H₅ | CH₃S | S |
| B.32 | CH | OCH₃ | 4-Br—C₆H₅ | CH₃CH₂O | O |
| B.33 | N | OCH₃ | 4-Cl—C₆H₅S | 3,5-Cl₂—C₆H₅O | O |
| B.34 | CH | OCH₃ | CH₃CH₂S | CH₃CH₂S | w = 0 |
| B.35 | N | OCH₃ | 4-Cl—C₆H₅S | 4-Cl—C₆H₅S | w = 0 |
| B.36 | CH | OCH₃ | 4-Cl—C₆H₅S | 3,5-Cl₂—C₆H₅O | w = 0 |
| B.37 | N | OCH₃ | 4-Cl-C₆H₅S | 3,5-Cl₂—C₆H₅O | w = 0 |
| B.38 | N | OCH₃ | CH₃CH₂O | 4-Cl—C₆H₅S | w = 0 |
| B.39 | CH | OCH₃ | C₆H₅O | C₆H₅O | w = 0 |
| B.40 | N | NHCH₃ | C₆H₅O | C₆H₅O | w = 0 |
| B.41 | CH | OCH₃ | 4-CF₃—C₆H₅ | CH₃S | w = 0 |
| B.42 | N | NHCH₃ | 4-CF₃—C₆H₅ | CH₃S | w = 0 |

Table 10-1: Compounds of general formula (1.10) wherein AR₇ is CH₃ and the combination of substituents X, Y, (W)$_w$, R₁₁ and R₁₂ for each compound corresponds to a line of Table B.

Compound of formula I.10 wherein A—R₇ is methyl and the substituents X, Y, (W)$_w$, R₁₁ and R₁₂ correspond to line B.1 of Table B; m.p.: 103–104° C. (compound 10-1.1).

Compound of formula I.10 wherein A—R₇ is methyl and the substituents X, Y, (W)$_w$, R₁₁ and R₁₂ correspond to line B.12 of Table B; m.p.: 95–96° C. (compound 10-1.12).

Table 10-2: Compounds of formula (I.10) wherein AR₇ is CH₂CH₃ and the combination of substituents X, Y, (W)$_w$, R₁₁ and R₁₂ for each compound corresponds to a line of Table B.

Table 10-3: Compounds of formula (I.10) wherein $AR_7$ is $CH_2CH=CH_2$ and the combination of substituents X, Y, $(W)_w$, $R_{11}$ and $R_{12}$ for each compound corresponds to a line of Table B.

Table 10-4: Compounds of formula (I.10) wherein $AR_7$ is $CH_2C\equiv CH$ and the combination of substituents X, Y, $(W)_w$, $R_{11}$ and $R_{12}$ for each compound corresponds to a line of Table B.

Table 10-5: Compounds of formula (I.10) wherein $AR_7$ is $CH_2CH_2CH_3$ and the combination of substituents X, Y, $(W)_w$, $R_{11}$ and $R_{12}$ for each compound corresponds to a line of Table B.

Table 10-6: Compounds of formula (I.10) wherein ARE is $CH(CH_3)_2$ and the combination of substituents X, Y, $(W)_w$, $R_{11}$ and $R_{12}$ for each compound corresponds to a line of Table B.

Table 10-7: Compounds of formula (I.10) wherein $AR_7$ is $CH_2CH_2CH_2CH_3$ and the combination of substituents X, Y, $(W)_w$, $R_{11}$ and $R_{12}$ for each compound corresponds to a line of Table B.

Table 10-8: Compounds of formula (I.10) wherein $AR_7$ is $CH(CH_3)(CH_2CH_3)$ and the combination of substituents X, Y, $(W)_w$, $R_{11}$ and $R_{12}$ for each compound corresponds to a line of Table B.

Table 10-9: Compounds of formula (I.10) wherein $AR_7$ is $C(CH_3)_3$ and the combination of substituents X, Y, $(W)_w$, $R_{11}$ and $R_{12}$ for each compound corresponds to a line of Table B.

Table 10-10: Compounds of formula (I.10) wherein $AR_7$ is $CH_2CF_3$ and the combination of substituents X, Y, $(W)_w$, $R_{11}$ and $R_{12}$ for each compound corresponds to a line of Table B.

Table 10-11: Compounds of formula (I.10) wherein $AR_7$ is $CH_2CH=C(CH_3)_2$ and the combination of substituents X, Y, $(W)_w$, $R_{11}$ and $R_{12}$ for each compound corresponds to a line of Table B.

Table 10-12: Compounds of formula (I.10) wherein $AR_7$ is $CH_2CH=CCl_2$ and the combination of substituents X, Y, $(W)_w$, $R_{11}$ and $R_{12}$ for each compound corresponds to a line of Table B.

Table 10-13: Compounds of formula (I.10) wherein $AR_7$ is $CH_2Si(CH_3)_3$ and the combination of substituents X, Y, $(W)_w$, $R_{11}$ and $R_{12}$ for each compound corresponds to a line of Table B.

Table 10-14: Compounds of formula (I.10) wherein $AR_7$ is $CH_2$c.propyl-2,2-$Cl_2$ and the combination of substituents X, Y, $(W)_w$, $R_{11}$ and $R_{12}$ for each compound corresponds to a line of Table B.

Table 10-15: Compounds of formula (I.10) wherein $AR_7$ is $CH_2CN$ and the combination of substituents X, Y, $(W)_w$, $R_{11}$ and $R_{12}$ for each compound corresponds to a line of Table B.

Table 10-16: Compounds of formula (I.10) wherein $AR_7$ is $CH_2COOCH_3$ and the combination of substituents X, Y, $(W)_w$, $R_{11}$ and $R_{12}$ for each compound corresponds to a line of Table B.

Table 10-17: Compounds of formula (I.10) wherein $AR_7$ is $CH_2COO$-iso-$C_3H_7$ and the combination of substituents X, Y, $(W)_w$, $R_{11}$ and $R_{12}$ for each compound corresponds to a line of Table B.

Table 10-18: Compounds of formula (I.10) wherein $AR_7$ is $C(=O)OC_2H_5$ and the combination of substituents X, Y, $(W)_w$, $R_{11}$ and $R_{12}$ for each compound corresponds to a line of Table B.

Table 10-19: Compounds of formula (I.10) wherein $AR_7$ is $C(=O)NHCH_3$ and the combination of substituents X, Y, $(W)_w$, $R_{11}$ and $R_{12}$ for each compound corresponds to a line of Table B.

Table 10-20: Compounds of formula (I.10) wherein $AR_7$ is $C(=O)C(=O)OC_2H_5$ and the combination of substituents X, Y, $(W)_w$, $R_{11}$ and $R_{12}$ for each compound corresponds to a line of Table B.

Table 10-21: Compounds of formula (I.10) wherein $AR_7$ is $CH_2C_6H_5$ and the combination of substituents X, Y, $(W)_w$, $R_{11}$ and $R_{12}$ for each compound corresponds to a line of Table B.

Table 10-22: Compounds of formula (I.10) wherein $AR_7$ is $CH_2C_6H_4$-2-F and the combination of substituents X, Y and $(W)_w$, $R_{11}$ and $R_{12}$ for each compound corresponds to a line of Table B.

Table 10-23: Compounds of formula (I.10) wherein $AR_7$ is $CH_2C_6H_4$-3-Cl and the combination of substituents X, Y, $(W)_w$, $R_{11}$ and $R_{12}$ for each compound corresponds to a line of Table B.

Table 10-24: Compounds of formula (I.10) wherein $AR_7$ is $CH_2C_6H_4$-4-Br and the combination of substituents X, Y, $(W)_w$, $R_{11}$ and $R_{12}$ for each compound corresponds to a line of Table B.

Table 10-25: Compounds of formula (I.10) wherein $AR_7$ is $CH_2C_6H_4$-3-$CF_3$ and the combination of substituents X, Y, $(W)_w$, $R_{11}$ and $R_{12}$ for each compound corresponds to a line of Table B.

Table 10-26: Compounds of formula (I.10) wherein $AR_7$ is $CH_2CrH_4$-4-$CF_3$ and the combination of substituents X, Y, $(W)_w$, $R_{11}$ and $R_{12}$ for each compound corresponds to a line of Table B.

TABLE 11-1

Compounds of formula (I.11)

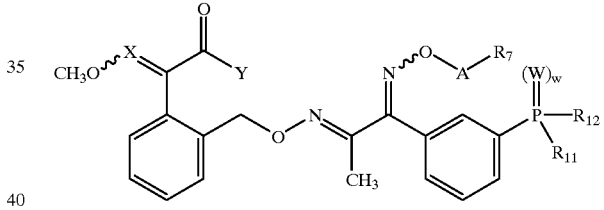

wherein $AR_7$ is $CH_3$ and the combination of substituents X, Y, $(W)_w$, $R_{11}$ and $R_{12}$ for each compound corresponds to a line of Table B.

Table 11-2: Compounds of formula (I.11) wherein $AR_7$ is $CH_2CH_3$ and the combination of substituents X, Y, $(W)_w$, $R_{11}$ and $R_{12}$ for each compound corresponds to a line of Table B.

Table 11-3: Compounds of formula (I.11) wherein $AR_7$ is $CH_2CH=CH_2$ and the combination of substituents X, Y, $(W)_w$, $R_{11}$ and $R_{12}$ for each compound corresponds to a line of Table B.

Table 114: Compounds of formula (I.11) wherein $AR_7$ is $CH_2CCH$ and the combination of substituents X, Y, $(W)_w$, $R_{11}$ and $R_{12}$ for each compound corresponds to a line of Table B.

Table 1 1-5: Compounds of formula (I.11) wherein $AR_7$ is $CH_2CH_2CH_3$ and the combination of substituents X, Y, $(W)_w$, $R_{11}$ and $R_{12}$ for each compound corresponds to a line of Table B.

Table 11-6: Compounds of formula (I.11) wherein $AR_7$ is $CH(CH_3)_2$ and the combination of substituents X, Y, $(W)_w$, $R_{11}$ and $R_{12}$ for each compound corresponds to a line of Table B.

Table 11-7: Compounds of formula (I.11) wherein $AR_7$ is $CH_2CH_2CH_2CH_3$ and the combination of substituents X, Y, $(W)_w$, $R_{11}$ and $R_{12}$ for each compound corresponds to a line of Table B.

Table 11-8: Compounds of formula (I.11) wherein AR$_7$ is CH(CH$_3$)(CH$_2$CH$_3$) and the combination of substituents X, Y, (W)$_w$, R$_{11}$ and R$_{12}$ for each compound corresponds to a line of Table B.

Table 11-9: Compounds of formula (I.11) wherein AR$_7$ is C(CH$_3$)$_3$ and the combination of substituents X, Y, (W)$_w$, R$_{11}$ and R$_{12}$ for each compound corresponds to a line of Table B.

Table 11-10: Compounds of formula (I.11) wherein AR$_7$ is CH$_2$CF$_3$ and the combination of substituents X, Y, (W)$_w$, R$_{11}$ and R$_{12}$ for each compound corresponds to a line of Table B.

Table 11-11: Compounds of formula (I.11 ) wherein AR$_7$ is CH$_2$CH=C(CH$_3$)$_2$ and the combination of substituents X, Y, (W)$_w$, R$_{11}$ and R$_{12}$ for each compound corresponds to a line of Table B.

Table 11-12: Compounds of formula (I.11) wherein AR$_7$ is CH$_2$CH=CC$_{12}$ and the combination of substituents X, Y, (W)$_w$, R$_{11}$ and R$_{12}$ for each compound corresponds to a line of Table B.

Table 11-13: Compounds of formula (I.11) wherein AR$_7$ is CH$_2$Si(CH$_3$)$_3$ and the combination of substituents X, Y, (W)$_w$, R$_{11}$ and R$_{12}$ for each compound corresponds to a line of Table B.

Table 11-14: Compounds of formula (I.11) wherein AR$_7$ is CH$_2$-c.propyl-2,2-Cl$_2$ and the combination of substituents X, Y, (W)$_w$, R$_{11}$ and R$_{12}$ for each compound corresponds to a line of Table B.

Table 11-15: Compounds of formula (I.11) wherein AR$_7$ is CH$_2$CN and the combination of substituents X, Y, (W)$_w$, R$_{11}$ and R$_{12}$ for each compound corresponds to a line of Table B.

Table 11-16: Compounds of formula (I.11) wherein AR$_7$ is CH$_2$COOCH$_3$ and the combination of substituents X, Y, (W)$_w$, R$_{11}$ and R$_{12}$ for each compound corresponds to a line of Table B.

Table 11-17: Compounds of formula (I.11) wherein AR$_7$ is CH$_2$COO-iso-C$_3$H$_7$ and the combination of substituents X, Y, (W)$_w$, R$_{11}$ and R$_{12}$ for each compound corresponds to a line of Table B.

Table 11-18: Compounds of formula (I.11) wherein AR$_7$ is C(=O)OC$_2$H$_5$ and the combination of substituents X, Y, (W)$_w$, R$_{11}$ and R$_{12}$ for each compound corresponds to a line of Table B.

Table 11-19: Compounds of formula (I.11) wherein AR$_7$ is C(=O)NHCH$_3$ and the combination of substituents X, Y, (W)$_w$, R$_{11}$ and R$_{12}$ for each compound corresponds to a line of Table B.

Table 11-20: Compounds of formula (I.11) wherein AR$_7$ is C(=O)C(=O)OC$_2$H$_5$ and the combination of substituents X, Y, (W)$_w$, R$_{11}$ and R$_{12}$ for each compound corresponds to a line of Table B.

Table 11-21: Compounds of formula (I.11) wherein AR$_7$ is CH$_2$C$_6$H$_5$ and the combination of substituents X, Y, (W)$_w$, R$_{11}$ and R$_{12}$ for each compound corresponds to a line of Table B.

Table 11-22: Compounds of formula (I.11) wherein AR$_7$ is CH$_2$C$_6$H$_4$-2-F and the combination of substituents X, Y, and (W)$_w$, R$_{11}$ and R$_{12}$ for each compound corresponds to a line of Table B.

Table 11-23: Compounds of formula (I.11) wherein AR$_7$ is CH$_2$C$_6$H$_4$-4-Br and the combination of substituents X, Y, (W)$_w$, R$_{11}$ and R$_{12}$ for each compound corresponds to a line of Table B.

Table 11-24: Compounds of formula (I.11) wherein AR$_7$ is CH$_2$C$_6$H$_4$-3-CF$_3$ and the combination of substituents X, Y, (W)$_w$, R$_{11}$ and R$_{12}$ for each compound corresponds to a line of Table B.

Table 11-25: Compounds of formula (I.11) wherein AR$_7$ is CH$_2$C$_6$H$_4$-4-CF$_3$ and the combination of substituents X, Y, (W)$_w$, R$_{11}$ and R$_{12}$ for each compound corresponds to a line of Table B.

Example P12-1: Preparation of the compounds of the formula

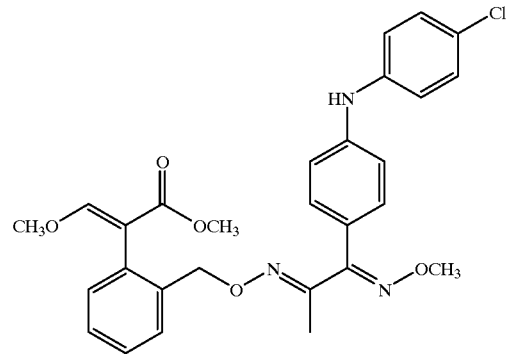

2.4 g of 2-{2-[2-(4-bromophenyl)$_2$-methoxyimino-methyl-ethylideneaminooxymethyl]-phenyl}-3-methoxy-acrylic acid methyl ester, 0.7 g of sodium tert-butanolate, 0.25 g of tris(dibenzylacetone)dipalladium(O), 110 mg of 1,1-bis(diphenylphosphine)ferrocene, 40 ml of toluene and 0.77 g of 4-chloroaniline are stirred under an argon atmosphere for 4 hours at 70° C. The reaction mixture is taken up in diethyl ether, washed with brine, dried and concentrated. Chromatography of the crude product on silica gel using ethyl acetate/hexane (1:19) yields 0.8 g of the crude product having a melting point of 82–83° C. (compound 12-1.3).

Example P1 2-2: Preparation of the compound of formula

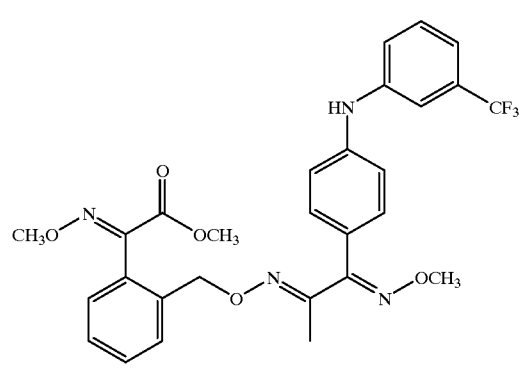

0.55 g of sodium hydride (55%) is added in portions to 3.5 g of 3-(4-(3-fluoromethylphenylamino)phenyl-2-hydroximino-3-methoximinopropane in 40 ml of dimethyl-formamide under an argon atmosphere in an ice bath. After one hour, 3.4 g of 2-(α-bromo-o-tolyl)-2-methoxyimino-acetic acid methyl ester are added and stirring is carried out for a further 20 hours at room temperature. 0.6 g of acetic acid is then added and the reaction mixture is concentrated. The residue is taken up in ethyl acetate; the mixture is washed with water, dried and concentrated. Chromatography of the residue on silica gel using ethyl acetate/hexane (1:9) yields 3.6 g of 2-{2-[2-(4-(3-fluoromethylphenylamino)-phenyl)-2-ethoxyimino-1-methyl-ethylideneaminooxymethyl]-phenyl}-3-methoxy-acrylic acid methyl ester having a melting point of 119–120° C. (compound 12-1.69).

Example P12-3: Preparation of the compound of the formula

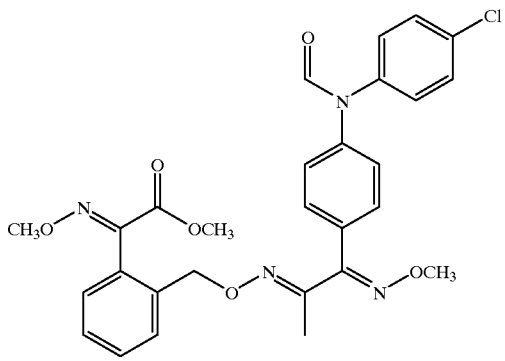

0.2 g of 2-{2-[2-(4-(4-chlorophenylamino)-phenyl)-2-methoxyimino-1-methyl-ethylideneaminooxymethyl]-phenyl}-3-methoxy-acrylic acid methyl ester and 7 ml of a 1M solution of formylacetic acid anhydride in diethyl ether are stirred under argon for 12 hours at 25° C. The reaction mixture is concentrated. Chromatography of the residue on silica gel using ethyl acetate/hexane (1:5) yields 0.03 g of the title product having a melting point of 145–146° C. (compound 12-1.64).

Example P12-4: It is also possible to prepare the other compounds listed in Tables 12 and 13 in a manner analogous to that described in Examples P1 2-1 to P12-3.

TABLE C

Compounds of general formulae (I.12)

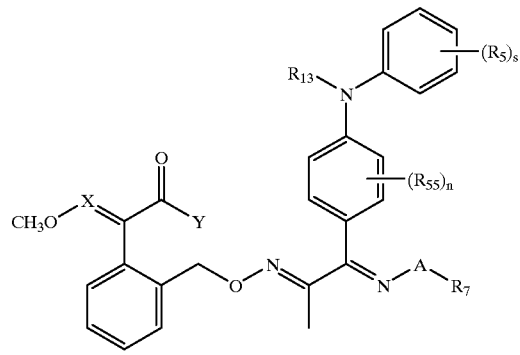

and (I.13)

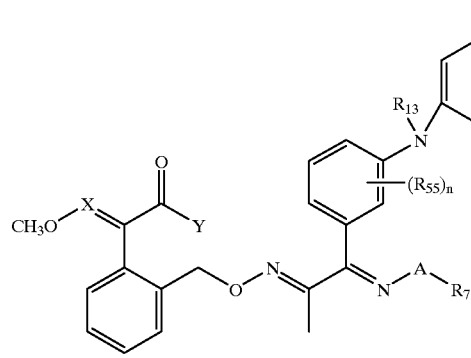

| No. | X | Y | $(R_5)_s$ | $(R_{55})_n$ | $R_{13}$ |
|---|---|---|---|---|---|
| C.1 | N | $OCH_3$ | 4-Cl | n = 0 | H |
| C.2 | N | $NHCH_3$ | 3-Cl | n = 0 | H |
| C.3 | CH | $OCH_3$ | 4-Cl | n = 0 | H |

TABLE C-continued

Compounds of general formulae (I.12)

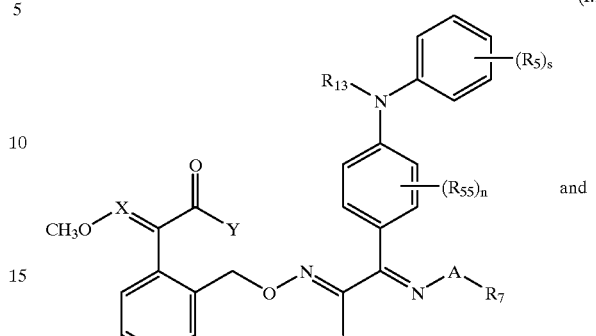

and (I.13)

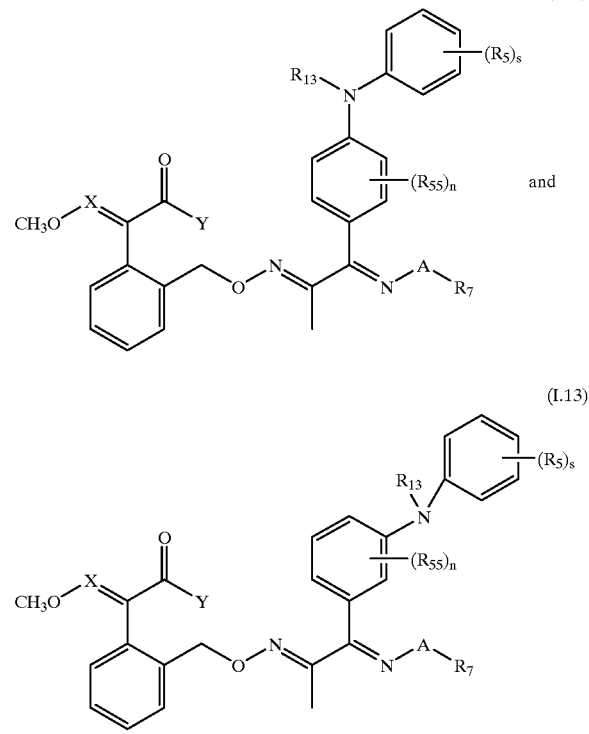

| No. | X | Y | $(R_5)_s$ | $(R_{55})_n$ | $R_{13}$ |
|---|---|---|---|---|---|
| C.4 | CH | $OCH_3$ | 4-Cl | n = 0 | $CH_3$ |
| C.5 | N | $OCH_3$ | 4-Cl | n = 0 | $CH_3$ |
| C.6 | N | $NHCH_3$ | 3-Cl | n = 0 | $CH_3$ |
| C.7 | CH | $OCH_3$ | 2-Cl | n = 0 | $CH_2CH_3$ |
| C.8 | N | $OCH_3$ | 4-Cl | n = 0 | $CH_2CH_3$ |
| C.9 | N | $NHCH_3$ | 4-Cl | n = 0 | $CH_2CH_3$ |
| C.10 | N | $NHCH_3$ | 4-Cl | n = 0 | C(O)H |
| C.11 | CH | $OCH_3$ | 4-Cl | n = 0 | $C(O)CH_3$ |
| C.12 | CH | $OCH_3$ | 2,4-$Cl_2$ | n = 0 | H |
| C.13 | CH | $OCH_3$ | 2,4-$Cl_2$ | n = 0 | $CH_3$ |
| C.14 | N | $OCH_3$ | 2,4-$Cl_2$ | n = 0 | $CH_3$ |
| C.15 | CH | $OCH_3$ | 2,4-$Cl_2$ | n = 0 | $CH_2CH_3$ |
| C.16 | N | $OCH_3$ | 2,4-$Cl_2$ | n = 0 | C(O)H |
| C.17 | CH | $OCH_3$ | 2,4-$Cl_2$ | n = 0 | $C(O)CH_3$ |
| C.18 | N | $NHCH_3$ | 2,4-$Cl_2$ | n = 0 | $C(O)CH_3$ |
| C.19 | N | $OCH_3$ | 4-$CF_3$ | n = 0 | H |
| C.20 | N | $NHCH_3$ | 4-$CF_3$ | n = 0 | H |
| C.21 | CH | $OCH_3$ | 4-$CF_3$ | n = 0 | $CH_3$ |
| C.22 | N | $NHCH_3$ | 3-$CF_3$ | n = 0 | $CH_3$ |
| C.23 | CH | $OCH_3$ | 4-$CF_3$ | n = 0 | $CH_2CH_3$ |
| C.24 | N | $NHCH_3$ | 4-$CF_3$ | n = 0 | $CH_2CH_3$ |
| C.25 | CH | $OCH_3$ | 3-$CF_3$ | n = 0 | C(O)H |
| C.26 | N | $NHCH_3$ | 4-$CF_3$ | n = 0 | C(O)H |
| C.27 | N | $NHCH_3$ | 4-$CF_3$ | n = 0 | $C(O)CH_3$ |
| C.28 | CH | $OCH_3$ | 3-$CF_3$ | n = 0 | H |
| C.29 | N | $NHCH_3$ | 3-$CF_3$ | n = 0 | H |
| C.30 | CH | $OCH_3$ | 3-$CF_3$ | n = 0 | $CH_2CH_3$ |
| C.31 | N | $NHCH_3$ | 3-$CF_3$ | n = 0 | $CH_2CH_3$ |
| C.32 | N | $OCH_3$ | 3-$CF_3$ | n = 0 | C(O)H |
| C.33 | N | $NHCH_3$ | 3-$CF_3$ | n = 0 | $C(O)CH_3$ |
| C.34 | CH | $OCH_3$ | 3-Cl | n = 0 | H |
| C.35 | CH | $OCH_3$ | 4-$NHCH_3$ | n = 0 | H |
| C.36 | CH | $OCH_3$ | 3-$OCH_3$ | n = 0 | $CH_3$ |
| C.37 | CH | $OCH_3$ | 3,5-$Cl_2$ | n = 0 | $CH_3$ |
| C.38 | CH | $OCH_3$ | 3,4-$Cl_2$ | n = 0 | iso-$CH_2CH_2CH_3$ |
| C.39 | CH | $OCH_3$ | 4-Br | n = 0 | $CH_2CH_3$ |
| C.40 | CH | $OCH_3$ | 4-$C_6H_5$ | n = 0 | n-$CH_2CH_2CH_3$ |
| C.41 | CH | $OCH_3$ | 2-CN | n = 0 | $CH_2OCH_3$ |
| C.42 | CH | $OCH_3$ | 3-$NO_2$ | n = 0 | C(O)H |

TABLE C-continued

Compounds of general formulae (I.12) and (I.13)

| No. | X | Y | $(R_5)_s$ | $(R_{55})_n$ | $R_{13}$ |
|---|---|---|---|---|---|
| C.43 | CH | OCH$_3$ | 3-C(O)CH$_3$ | n = 0 | C(O)C(O)CH$_3$ |
| C.44 | CH | OCH$_3$ | 4-NHC(O)CH$_3$ | n = 0 | C(O)C(O)OCH$_3$ |
| C.45 | CH | OCH$_3$ | 4-SF$_5$ | n = 0 | C(O)CH$_2$CH$_3$ |
| C.46 | CH | OCH$_3$ | 3-OCF$_3$ | n = 0 | C(S)CH$_3$ |
| C.47 | CH | OCH$_3$ | 4-Cl | n = 0 | C(S)SCH$_3$ |
| C.48 | CH | OCH$_3$ | 3-Cl | 3-Cl | H |
| C.49 | CH | OCH$_3$ | 4-CH$_3$ | 2-Br | H |
| C.50 | CH | OCH$_3$ | 4-NHCH$_3$ | 2-CN | H |
| C.51 | CH | OCH$_3$ | 3-OCH$_3$ | 3-Cl | CH$_3$ |
| C.52 | CH | OCH$_3$ | 3,5-Cl$_2$ | 2-F | CH$_3$ |
| C.53 | CH | OCH$_3$ | 3,4-Cl$_2$ | 2-OCH$_3$ | iso-CH$_2$CH$_2$CH$_3$ |
| C.54 | CH | OCH$_3$ | 4-Br | 3,5-Cl$_2$ | CH$_2$CH$_3$ |
| C.55 | CH | OCH$_3$ | 4-C$_6$H$_5$ | 3-CH$_3$ | n-CH$_2$CH$_2$CH$_3$ |
| C.56 | CH | OCH$_3$ | 2-CN | 3,5-F$_2$ | CH$_2$OCH$_3$ |
| C.57 | CH | OCH$_3$ | 3-NO$_2$ | 2,3-F$_2$ | C(O)H |
| C.58 | CH | OCH$_3$ | 3-C(O)CH$_3$ | 3-NHCH$_3$ | C(O)C(O)CH$_3$ |
| C.59 | CH | OCH$_3$ | 4-NHC(O)CH$_3$ | 3-Cl | C(O)C(O)OCH$_3$ |
| C.60 | CH | OCH$_3$ | 4-SF$_5$ | 2-Cl | C(O)CH$_2$CH$_3$ |
| C.61 | CH | OCH$_3$ | 3-OCF$_3$ | 3-SCH$_3$ | C(S)CH$_3$ |
| C.62 | CH | OCH$_3$ | 4-Cl | 2,6-Cl$_2$ | C(S)SCH$_3$ |
| C.63 | CH | OCH$_3$ | 4-CF$_3$ | n = 0 | H |
| C.64 | CH | OCH$_3$ | 4-Cl | n = 0 | C(O)H |
| C.65 | CH | OCH$_3$ | 4-CF$_3$ | n = 0 | C(O)H |
| C.66 | CH | OCH$_3$ | 4-OCF$_3$ | n = 0 | H |
| C.67 | CH | OCH$_3$ | 4-OCF$_3$ | n = 0 | C(O)H |
| C.68 | CH | OCH$_3$ | 2,4-F$_2$ | n = 0 | H |
| C.69 | N | OCH$_3$ | 3-CF$_3$ | n = 0 | H |
| C.70 | N | OCH$_3$ | 4-OCF$_3$ | n = 0 | H |
| C.71 | N | OCH$_3$ | 4-OCF$_3$ | n = 0 | C(O)H |
| C.72 | N | OCH$_3$ | 2,4-F$_2$ | n = 0 | H |
| C.73 | N | NCH$_3$ | 4-OCF$_3$ | n = 0 | H |
| C.74 | N | NCH$_3$ | 2,4-F$_2$ | n = 0 | H |

Table 12-1: Compounds of formula 1.12 wherein AR$_7$ is CH$_3$ and the combination of substituents X, Y, $(R_5)_s$, $(R_{55})_n$ and $R_{13}$ for each compound corresponds to a line of Table C.

Compound of formula (I.12) wherein A—R$_7$ is methyl and the substituents X, Y, $(R_5)_s$, $(R_{55})_n$ and $R_{13}$ correspond to line C.4 of Table C: m.p.: 126–127° C. (compound 12-1.4).

Compound of formula (I.12) wherein A—R$_7$ is methyl and the substituents X, Y, $(R_5)_s$, $(R_{55})_n$ and $R_{13}$ correspond to line C.12 of Table C: m.p.: 132–133° C. (compound 12-1.12).

Compound of formula (I.12) wherein A—R$_7$ is methyl and the substituents X, Y, $(R_5)_s$, $(R_{55})_n$ and $R_{13}$ correspond to line C.24 of Table C: amorphous (compound 12-1.24).

Compound of formula (I.12) wherein A—R$_7$ is methyl and the substituents X, Y, $(R_5)_s$, $(R_{55})_n$ and $R_{13}$ correspond to line C.28 of Table C: m.p.: 83–84° C. (compound 12-1.28).

Compound of formula (I.12) wherein A—R$_7$ is methyl and the substituents X, Y, $(R_5)_s$, $(R_{55})_n$ and $R_{13}$ correspond to line C.29 of Table C: m.p.: 76–77° C. (compound 12-1.29).

Compound of formula (I.12) wherein A—R$_7$ is methyl and the substituents X, Y, $(R_5)_s$, $(R_{55})_n$ and $R_{13}$ correspond to line C.63 of Table C: m.p.: 83–84° C. (compound 12-1.63).

Compound of formula (I.12) wherein A—R$_7$ is methyl and the substituents X, Y, $(R_5)_s$, $(R_{55})_n$ and $R_{13}$ correspond to line C.64 of Table C: m.p.: 146–148° C. (compound 12-1.64).

Compound of formula (I.12) wherein A—R$_7$ is methyl and the substituents X, Y, $(R_5)_s$, $(R_{55})_n$ and $R_{13}$ correspond to line C.65 of Table C: m.p.: 109–110° C. (compound 12-1.65).

Compound of formula (I.12) wherein A—R$_7$ is methyl and the substituents X, Y, $(R_5)_s$, $(R_{55})_n$ and $R_{13}$ correspond to line C.32 of Table C: m.p.: 104–105° C. (compound 12-1.32).

Compound of formula (I.12) wherein A—R$_7$ is methyl and the substituents X, Y, $(R_5)_s$, $(R_{55})_n$ and $R_{13}$ correspond to line C.66 of Table C: m.p.: 74–85° C. (compound 12-1.66).

Compound of formula (I.12) wherein A—R$_7$ is methyl and the substituents X, Y, $(R_5)_s$, $(R_{55})_n$ and $R_{13}$ correspond to line C.67 of Table C: m.p.: 65–76° C. (compound 12-1.67).

Compound of formula (I.12) wherein A—R$_7$ is methyl and the substituents X, Y, $(R_5)_s$, $(R_{55})_n$ and $R_{13}$ correspond to line C.68 of Table C: m.p.: 126–127° C. (compound 12-1.68).

Compound of formula (I.12) wherein A—R$_7$ is methyl and the substituents X, Y, $(R_5)_s$, $(R_{55})_n$ and $R_{13}$ correspond to line C.70 of Table C: m.p.: 122–123° C. (compound 12-1.70).

Compound of formula (I.12) wherein A—R$_7$ is methyl and the substituents X, Y, $(R_5)_s$, $(R_{55})_n$ and $R_{13}$ correspond to line C.71 of Table C: m.p.: 58–59° C. (compound 12-1.71).

Compound of formula (I.12) wherein A—R$_7$ is methyl and the substituents X, Y, $(R_5)_s$, $(R_{55})_n$ and $R_{13}$ correspond to line C.73 of Table C: m.p.: 63–64° C. (compound 12-1.73).

Table 12-2: Compounds of formula (I.12) wherein AR$_7$ is CH$_2$CH$_3$ and the combination of substituents X, Y, $(R_5)_s$, $(R_{55})_n$ and $R_{13}$ for each compound corresponds to a line of Table 2.

Compound of formula (I.12) wherein A—R$_7$ is ethyl and the substituents X, Y, $(R_5)_s$, $(R_{55})_n$ and $R_{13}$ correspond to line C.24 of Table C: m.p.: 56–57° C. (compound 12-2.24).

Compound of formula (I.12) wherein A—R$_7$ is ethyl and the substituents X, Y, $(R_5)_s$, $(R_{55})_n$ and $R_{13}$ correspond to line C.28 of Table C: m.p.: 90–91° C. (compound 12-2.28).

Compound of formula (I.12) wherein A—R$_7$ is ethyl and the substituents X, Y, (R$_5$)$_s$, (R$_{55}$R$_6$)$_n$ and R$_{13}$ correspond to line C.29 of Table C: m.p.: 168–169° C. (compound 12-2.29).

Compound of formula (I.12) wherein A—R$_7$ is ethyl and the substituents X, Y, (R$_5$)$_s$, (R$_6$)$_n$ and R$_{13}$ correspond to line C.33 of Table C: m.p.: 59–60° C. (compound 12-2.33).

Compound of formula (I.12) wherein A—R$_7$ is ethyl and the substituents X, Y, (R$_5$)$_s$, (R$_6$)$_n$ and R$_{13}$ correspond to line C.69 of Table C: resin (compound 12-2.69).

Compound of formula (I.12) wherein A—R$_7$ is ethyl and the substituents X, Y, (R$_5$)$_s$, (R$_6$)$_n$ and R$_{13}$ correspond to line C.70 of Table C: m.p.: 132–133° C. (compound 12-2.70).

Compound of formula (I.12) wherein A—R$_7$ is ethyl and the substituents X, Y, (R$_5$)$_s$, (R$_6$)$_n$ and R$_{13}$ correspond to line C.71 of Table C: m.p.: 131–132° C. (compound 12-2.72).

Compound of formula (I.12) wherein A—R$_7$ is ethyl and the substituents X, Y, (R$_{15}$)$_s$ (R$_6$)$_n$ and R$_{13}$ correspond to line C.73 of Table C: m.p.: 69–70° C. (compound 12-2.73).

Compound of formula (I.12) wherein A—R$_7$ is ethyl and the substituents X, Y, (R$_5$)$_s$, (R$_{55}$)$_n$ and R$_{13}$ correspond to line C.74 of Table C: m.p.: 70–71° C. (compound 12-2.74).

Table 12-3: Compounds of formula (I.12) wherein AR$_7$ is CH$_2$CH=CH$_2$ and the combination of substituents X, Y, (R$_5$)$_s$, (R55)$_n$ and R$_{13}$ for each compound corresponds to a line of Table 2.

Table 12-4: Compounds of formula (I.12) wherein AR$_7$ is CH$_2$C=CH and the combination of substituents X, Y, (R$_5$)$_s$, (R$_{55}$)$_n$ and R$_{13}$ for each compound corresponds to a line of Table 2.

Table 12-5: Compounds of formula (I.12) wherein AR$_7$ is CH$_2$CH$_2$CH$_3$ and the combination of substituents X, Y, (R$_5$)$_s$, (R$_{55}$)$_n$ and R$_{13}$ for each compound corresponds to a line of Table 2.

Table 12-6: Compounds of formula (I.12) wherein AR$_7$ is CH(CH$_3$)$_2$ and the combination of substituents X, Y, (R$_5$)$_s$, (R$_{55}$)$_n$ and R$_{13}$ for each compound corresponds to a line of Table C. Table 12-7: Compounds of formula (I.12) wherein AR$_7$ is CH$_2$CH$_2$CH$_2$CH$_3$ and the combination of substituents X, Y, (R$_5$)$_s$, (R$_{55}$)$_n$ and R$_{13}$ for each compound corresponds to a line of Table C.

Table 12-8: Compounds of formula (I.12) wherein AR$_7$ is CH(CH$_3$)(CH$_2$CH$_3$) and the combination of substituents X, Y, (R$_5$)$_s$, (R$_{55}$)$_n$ and R$_{13}$ for each compound corresponds to a line of Table C.

Table 12-9: Compounds of formula (I.12) wherein AR$_7$ is C(CH$_3$)$_3$ and the combination of substituents X, Y, (R$_5$)$_s$, (R$^{55}$)$_n$ and R$_{13}$ for each compound corresponds to a line of Table C.

Table 12-10: Compounds of formula (I.12) wherein AR$_7$ is CH$_2$CF$_3$ and the combination of substituents X, Y, (R$_5$)$_s$, (R$_{55}$)$_n$ and R$_{13}$ for each compound corresponds to a line of Table C.

Table 12-11: Compounds of formula (I.12) wherein AR$_7$ is CH$_2$CH=C(CH$_3$)$_2$ and the combination of substituents X, Y, (R$_5$)$_s$, (R$_{55}$)$_n$ and R$_{13}$ for each compound corresponds to a line of Table C.

Table 12-12: Compounds of formula (I.12) wherein AR$_7$ is CH$_2$CH=CCl$_2$ and the combination of substituents X, Y, (R$_5$)$_s$, (R$_{55}$)$_n$ and R$_{13}$ for each compound corresponds to a line of Table C.

Table 12-13: Compounds of formula (I.12) wherein AR$_7$ is CH$_2$Si(CH$_3$)$_3$ and the combination of substituents X, Y, (R$_5$)$_s$, (R$_{55}$)$_n$ and R$_{13}$ for each compound corresponds to a line of Table C.

Table 12-14: Compounds of formula (I.12) wherein AR$_7$ is CH$_2$-c.propyl-2,2-Cl$_2$ and the combination of substituents X, Y, (R$_5$)$_s$, (R$_{55}$)$_n$ and R$_{13}$ for each compound corresponds to a line of Table C.

Table 12-15: Compounds of formula (I.12) wherein AR$_7$ is CH$_2$CN and the combination of substituents X, Y, (R$_5$)$_s$, (R$_{55}$)$_n$ and R$_{13}$ for each compound corresponds to a line of Table C.

Table 12-16: Compounds of formula (I.12) wherein AR$_7$ is CH$_2$COOCH$_3$ and the combination of substituents X, Y, (R$_5$)$_s$, (R$_{55}$)$_n$ and R$_{13}$ for each compound corresponds to a line of Table C.

Table 12-17: Compounds of formula (I.12) wherein AR$_7$ is CH$_2$COO-iso-C$_3$H$_7$ and the combination of substituents X, Y, (R$_5$)$_s$, (R$_{55}$)$_n$ and R$_{13}$ for each compound corresponds to a line of Table C.

Table 12-18: Compounds of formula (I.12) wherein AR$_7$ is C(=O)OC$_2$H$_5$ and the combination of substituents X, Y, (R$_5$)$_s$, (R$_{55}$)$_n$ and R$_{13}$ for each compound corresponds to a line of Table C.

Table 12-19: Compounds of formula (I.12) wherein AR$_7$ is C(=O)NHCH$_3$ and the combination of substituents X, Y, (R$_5$)$_s$, (R$_{55}$)$_n$ and R$_{13}$ for each compound corresponds to a line of Table C.

Table 12-20: Compounds of formula (I.12) wherein AR$_7$ is C(=O)C(=O)OC$_2$H$_5$ and the combination of substituents X, Y, (R$_5$)$_s$, (R$_{55}$)$_n$ and R$_{13}$ for each compound corresponds to a line of Table C.

Table 12-21: Compounds of formula (I.12) wherein AR$_7$ is CH$_2$C$_6$H$_5$ and the combination of substituents X, Y, (R$_5$)$_s$, (R$_{55}$)$_n$ and R$_{13}$ for each compound corresponds to a line of Table C.

Table 12-22: Compounds of formula (I.12) wherein AR$_7$ is CH$_2$C$_6$H$_4$-2-F and the combination of substituents X, Y, (R$_5$)$_s$, (R$_{55}$)$_n$ and R$_{13}$ for each compound corresponds to a line of Table C.

Table 12-23: Compounds of formula (I.12) wherein AR$_7$ is CH$_2$C$_6$H$_4$-3-Cl and the combination of substituents X, Y, (R$_5$)$_s$, (R$_{55}$)$_n$ and R$_{13}$ for each compound corresponds to a line of Table C.

Table 12-24: Compounds of formula (I.12) wherein AR$_7$ is CH$_2$C$_6$H$_4$-4-Br and the combination of substituents X, Y, (R$_5$)$_s$, (R$_{55}$)$_n$ and R$_{13}$ for each compound corresponds to a line of Table C.

Table 12-25: Compounds of formula (I.12) wherein AR$_7$ is CH$_2$C$_6$H$_4$-3-CF$_3$ and the combination of substituents X, Y, (R$_5$)$_s$, (R$_{55}$)$_n$ and R$_{13}$ for each compound corresponds to a line of Table C.

Table 12-26: Compounds of formula (I.12) wherein AR$_7$ is CH$_2$C$_6$H$_4$-4-CF$_3$ and the combination of substituents X, Y, (R$_5$)$_s$, (R$_{55}$)$_n$ and R$_{13}$ for each compound corresponds to a line of Table C.

Table 13-1: Compounds of formula (I.13) wherein AR$_7$ is CH$_3$ and the combination of substituents X, Y, (R$_5$)$_s$, (R$_{55}$)$_n$ and R$_{13}$ for each compound corresponds to a line of Table C.

Table 13-2: Compounds of formula (I.13) wherein AR$_7$ is CH$_2$CH$_3$ and the combination of substituents X, Y, (R$_5$)$_s$, (R$_{55}$)$_n$ and R$_{13}$ for each compound corresponds to a line of Table C.

Table 13-3: Compounds of formula (I.13) wherein AR$_7$ is CH$_2$CH=CH$_2$ and the combination of substituents X, Y, (R$_5$)$_s$, (R$_{55}$)$_n$ and R$_{13}$ for each compound corresponds to a line of Table C.

Table 13-4: Compounds of formula (I.13) wherein AR$_7$ is CH$_2$C=CH and the combination of substituents X, Y, (R$_5$)$_s$, (R$_{55}$)$_n$ and R$_{13}$ for each compound corresponds to a line of Table C.

Table 13-5: Compounds of formula (I.13) wherein AR$_7$ is CH$_2$CH$_2$CH$_3$ and the combination of substituents X, Y, $(R_5)_s$, $(R_{55})_n$ and $R_{13}$ for each compound corresponds to a line of Table C.

Table 13-6: Compounds of formula (I.13) wherein $AR_7$ is $CH(CH_3)_2$ and the combination of substituents X, Y, $(R_5)_s$, $(R_{55})_n$ and $R_{13}$ for each compound corresponds to a line of Table C.

Table 13-7: Compounds of formula (I.13) wherein $AR_7$ is $CH_2CH_2CH_2CH_3$ and the combination of substituents X, Y, $(R_5)_s$, $(R_{55})_n$ and $R_{13}$ for each compound corresponds to a line of Table C.

Table 13-8: Compounds of formula (I.13) wherein $AR_7$ is $CH(CH_3)(CH_2CH_3)$ and the combination of substituents X, Y, $(R_5)_s$, $(R_{55})_n$ and $R_{13}$ for each compound corresponds to a line of Table C.

Table 13-9: Compounds of formula (I.13) wherein $AR_7$ is $C(CH_3)_3$ and the combination of substituents X, Y, $(R_5)_s$, $(R_{55})_n$ and $R_{13}$ for each compound corresponds to a line of Table C.

TABLE 14

Compounds of formula

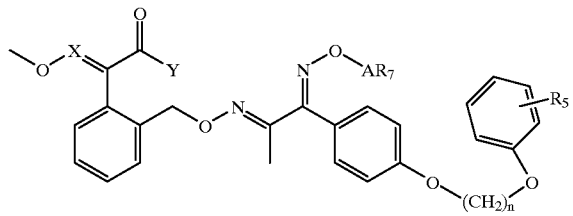

(I.14)

The figures in the column "Phys. data" denote melting points in °C.

| No. | $R_5$ | $AR_7$ | X | Y | n | Phys. data |
|---|---|---|---|---|---|---|
| 14.1 | 2-Cl | $C_2H_5$ | CH | $OCH_3$ | 2 | oil |
| 14.2 | 2-Cl | $C_2H_5$ | N | $OCH_3$ | 2 | m.p. 83–85° C. |
| 14.3 | 2-Cl | $C_2H_5$ | N | $NHCH_3$ | 2 | oil |
| 14.4 | 4-Cl | $C_2H_5$ | CH | $OCH_3$ | 2 | m.p. 90–92° C. |
| 14.5 | 4-Cl | $C_2H_5$ | N | $OCH_3$ | 2 | m.p. 85–87° C. |
| 14.6 | 4-Cl | $C_2H_5$ | N | $NHCH_3$ | 2 | oil |
| 14.7 | 4-$CF_3$ | $C_2H_5$ | CH | $OCH_3$ | 2 | |
| 14.8 | 4-$CF_3$ | $C_2H_5$ | N | $OCH_3$ | 2 | |
| 14.9 | 4-$CF_3$ | $C_2H_5$ | N | $NHCH_3$ | 2 | |
| 14.10 | 2-$CF_3$ | $C_2H_5$ | CH | $OCH_3$ | 2 | |
| 14.11 | 2-$CF_3$ | $C_2H_5$ | N | $OCH_3$ | 2 | |
| 14.12 | 2-$CF_3$ | $C_2H_5$ | N | $NHCH_3$ | 2 | |
| 14.13 | 4-$CF_3$ | $C_2H_5$ | N | $OCH_3$ | 3 | oil |
| 14.14 | 4-$CF_3$ | $CH_3$ | CH | $OCH_3$ | 3 | resin |
| 14.15 | 3-$CF_3$ | $CH_3$ | CH | $OCH_3$ | 4 | oil |
| 14.16 | 4-$CF_3$ | $CH_3$ | CH | $OCH_3$ | 4 | resin |
| 14.17 | 4-$CF_3$ | $C_2H_5$ | N | $OCH_3$ | 4 | oil |
| 14.18 | 3-$CF_3$ | $CH_3$ | CH | $OCH_3$ | 4 | oil |
| 14.19 | 3-$CF_3$ | $C_2H_5$ | N | $OCH_3$ | 4 | oil |
| 14.20 | 3-$CF_3$ | $C_2H_5$ | N | $NHCH_3$ | 4 | oil |
| 14.21 | 3-$CF_3$ | $C_2H_5$ | N | $OCH_3$ | 3 | oil |
| 14.22 | 3-$CF_3$ | $C_2H_5$ | N | $NHCH_3$ | 3 | resin |

TABLE 15

Compounds of formula

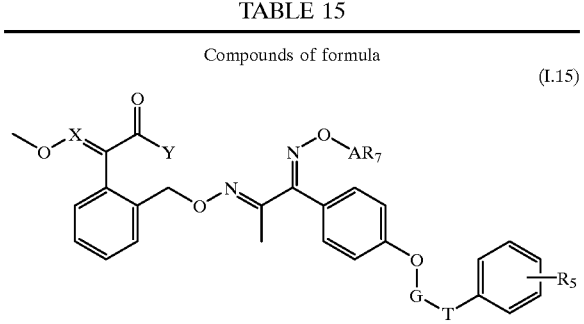

(I.15)

The figures in the column "Phys. data" denote melting points in °C.

| No. | $R_5$ | $AR_7$ | X | Y | G–T | Phys. data |
|---|---|---|---|---|---|---|
| 15.1 | H | $C_2H_5$ | CH | $OCH_3$ | $CH_2$—$CH_2$ | oil |
| 15.2 | H | $C_2H_5$ | N | $OCH_3$ | $CH_2$—$CH_2$ | oil |
| 15.3 | H | $C_2H_5$ | N | $NHCH_3$ | $CH_2$—$CH_2$ | resin |
| 15.4 | H | $CH_3$ | CH | $OCH_3$ | $CH_2$—S | oil |
| 15.5 | H | $CH_3$ | N | $OCH_3$ | $CH_2$—S | resin |
| 15.6 | H | $CH_3$ | N | $NHCH_3$ | $CH_2$—S | 111–113 |
| 15.7 | H | $C_2H_5$ | CH | $OCH_3$ | $CH_2$—S | oil |
| 15.8 | H | $C_2H_5$ | N | $OCH_3$ | $CH_2$—S | oil |
| 15.9 | H | $C_2H_5$ | N | $NHCH_3$ | $CH_2$—S | resin |
| 15.10 | H | $CH_2C\equiv CH$ | CH | $OCH_3$ | $CH_2$—S | oil |
| 15.11 | H | $CH_2C\equiv CH$ | N | $OCH_3$ | $CH_2$—S | oil |
| 15.12 | H | $CH_2C\equiv CH$ | N | $NHCH_3$ | $CH_2$—S | resin |
| 15.13 | 4-F | $C_2H_5$ | N | $OCH_3$ | $CH_2$—CO— | resin |

Formulation Examples

Formulations such as emulsifiable concentrates, solutions granules, dusts, wettable powders, emulsifiable concentrates, extruder granules, coated granules and suspension concentrates are of the same kind as mentioned in EP-A-736 252, examples F1 to F10. Accordingly, the said formulations mentioned in EP-A-736 252 are included by reference in the subject matter of the present invention.

Biological Examples

A) Microbicidal action

Example B1: Action against *Phytophthora infestans* on tomatoes a) Curative action After a cultivation period of three weeks, tomato plants of the "Red Gnome" variety are sprayed with a zoospore suspension of the fungus and incubated in a humidity chamber at 18 to 20° C. and saturated humidity. Humidifying is discontinued after 24 hours. When the plants have dried off, they are sprayed with a mixture containing a wettable powder formulation of the test compound at a concentration of 200 ppm. After the spray-coating has dried, the plants are again placed in the humidity chamber for 4 days. The number and size of the typical leaf blotches that have appeared after that time serve as a measure for evaluating the effectiveness of the test compounds.

b) Preventive-systemic action

A wettable powder formulation of the test compound at a concentration of 60 ppm (based on the volume of soil) is used to water the surface of the soil in which three-week-old tomato plants of the "Red Gnome" variety have been potted. After a waiting period of three days, the undersides of the leaves of the plants are sprayed with a zoospore suspension of Phytophthora infestans. The treated plants are then placed in a spraying cabinet for 5 days at 18 to 20° C. and saturated humidity. After that period, typical leaf blotches appear, the number and size of which are used to evaluate the effectiveness of the test compounds.

Whereas infestation in untreated and infected control plants is 100%, with the compounds of Tables 1 to 15 infestation is reduced to 20% or less in both tests. In particular, with the compounds 1-4.2, 24.2, 34.2, 4-1.1, 5.5, 6.3, 8.10 and 9-2.2 the infestation is still fully suppressed even at a concentration of 20 ppm of the test compound.

Example B2: Action against *Plasmopara viticola* (Bert. et Curt.) (Berd. et DeToni) on vines Vine cuttings of the "Chasselas" variety are cultivated in a greenhouse and are infected at the 10-leaf stage, on the undersides of the leaves, with a spore suspension of *Plasmopara viticola*. After being kept in a humidity chamber for 24 hours, the plants are sprayed with mixtures comprising the active ingredient in concentrations of 200 ppm, 60 ppm and 20 ppm. The plants are then kept in the humidity chamber for a further 7 days. After that time, the disease symptoms appear in the control plants. The number and size of the infection sites on the treated plants serve as a measure for evaluating the effectiveness of the test compounds.

In comparison with the control plants, the plants treated with compounds of Tables 1 to 15 exhibit an infestation of 20% or less. In particular, with the compounds 1-4.2, 3-4.2, 4-1.2, 6.3, 8.10 and 9-2.2 complete curative action is still obtained even at a concentration of 20 ppm of the test compound.

Example B3: Action against *Puccinia graminis* on wheat a) Residual-protective action 6 days after sowing, wheat plants are sprayed to drip point with an aqueous spray mixture (0.02% active ingredient), and infected 24 hours later with a uredospore suspension of the fungus. After an incubation period of 48 hours (conditions: 95 to 100% relative humidity at 20° C.), the plants are placed in a greenhouse at 22° C. Evaluation of rust pustule development is made 12 days after infection.

b) Systemic action

Wheat plants are watered 5 days after sowing with an aqueous spray mixture (0.006% active ingredient, based on the volume of soil). Care is taken that the spray mixture does not come into contact with the parts of the plants above the soil. The treated plants are infected 48 hours later with a uredospore suspension of the fungus. After an incubation period of 48 hours (conditions: 95 to 100% relative humidity at 20° C. ), the plants are placed in a greenhouse at 22° C. Evaluation of rust pustule development is made 12 days after infection.

The compounds of Tables 1 to 15 bring about a distinct reduction in the fungus infestation, in some cases to from 10 to 0%. In particular, with the compounds 3-4.2, 4.1-1, 5.4, 8.10, 12-1.3, 10-1.16 and 12-1.4 the disease is suppressed completely (0–5% infestation).

Example B4: Action against *Pyricularia oryzae* on rice plants a) Residual-protective action After a cultivation period of 2 weeks, rice plants are sprayed to drip point with an aqueous spray mixture (0.02% active ingredient), and are infected 48 hours later with a conidia suspension of the fungus. Evaluation of fungus infestation is made 5 days after infection, during which period 95 to 100% relative humidity and a temperature of 22° C. are maintained.

b) Systemic action 2-week-old rice plants are watered with an aqueous spray mixture (0.006% active ingredient, based on the volume of soil). Care is taken that the spray mixture does not come into contact with the parts of the plant above the soil. The pots are then filled with water so that the lowermost parts of the stems of the rice plants stand in water. After 96 hours, the plants are infected with a conidia suspension of the fungus and kept for 5 days at 95 to 100% relative humidity and a temperature of 24° C.

The compounds of Tables 1 to 15 largely prevent the disease from breaking out on the infected plants.

Example B5: Action against *Erysiphe graminis* on barley

) Residual-protective action

Barley plants about 8 cm in height are sprayed to drip point with an aqueous spray mixture (0.02% active ingredient) and dusted 3 to 4 hours later with conidia of the fungus. The infected plants are placed in a greenhouse at 22° C. The fungus infestation is evaluated 10 days after infection.

b) Systemic action

Barley plant s about 8 cm in height are watered with an aqueous spray mixture (0.002% active ingredient, based on the volume of soil). Care is taken that the spray mixture does not come into contact With the parts of the plants above the soil. The treated plants are dusted 48 hours later with conidia of the fungus. The infected plants are placed in a greenhouse at 22° C. The fungus infestation is evaluated 10 days after infection.

The compounds of Tables 1 to 15 in general are able to suppress infestation with the disease to less than 20% and, in some cases, to suppress it completely.

Example B6: Action against *Botryis cinerea* on apple fruits, Residual-protective action Artificially damaged apples are treated by applying drops of a spray mixture (0.02% active ingredient) onto the damage sites. The treated fruits are then inoculated with a spore suspension of the fungus and incubated for one week at high humidity and about 20° C. The fungicidal action of the test compound is derived from the number of rotted damage sites.

Compounds of Tables 1 to 15 are able to prevent the rot from spreading, in some cases completely.

B. Insecticidal action

Example B7: Action against *Aphis craccivora*

Pea seedlings are infested with *Aphis craccivora,* subsequently sprayed with a spray mixture comprising 100 ppm of the test compound and then incubated at 20° C. 3 and 6 days later the percentage reduction in population (% activity) is determined by comparing the number of dead aphids on the treated plants with that on untreated plants.

The compounds of Tables 1 to 15 generally exhibit good activity in this test. In particular, compounds 1-4.2, 4.2, 34.2, 4-1.3, 4-1.7, 5.1, 5.3 and 8.10 are more than 80% effective in this test.

Example B8: Action against *Diabrotica balteata*

Maize seedlings are sprayed with an aqueous emulsion spray mixture comprising 100 ppm of the test compound. After the spray-coating has dried, the maize seedlings are populated with 10 *Diabrotica balteata* larvae in the second stage and then placed in a plastics container. 6 days later, the percentage reduction in population (% activity) is determined by comparing the number of dead larvae on the treated plants with that on untreated plants. The compounds of Tables 1 to 15 exhibit good activity in this test. In particular, compounds 1-4.2, 2-4.2, 4-1.2, 4-1.8, 5.5, 9-2.2, 12-1.3, 10-1.16 and 12-1.4 are more than 80% effective in this test.

Example B9: Action against *Heliothis virescens*

Young soybean plants are sprayed with an aqueous emulsion spray mixture comprising 100 ppm of the test compound. After the spray-coating has dried, the plants are populated with 10 *Heliothis virescens* caterpillars in the first stage and then placed in a plastics container. 6 days later, the percentage reduction in population and the percentage reduction in feeding damage (% activity) are determined by comparing the number of dead caterpillars and the feeding damage on the treated plants with that on untreated plants. Most compounds of Tables 1 to 15 exhibit good activity in this test. In particular, compound 5.1 is more than 80% effective in this test Example B10: Action against *Spodoptera littoralis*

Young soybean plants are sprayed with an aqueous emulsion spray mixture comprising 100 ppm of the test compound. After the spray-coating has dried, the plants are populated with 10 *Spodoptera littoralis* caterpillars in the third stage and then placed in a plastics container. 3 days later, the percentage reduction in population and the percentage reduction in feeding damage (% activity) are determined by comparing the number of dead caterpillars and the feeding damage on the treated plants with that on untreated plants. The compounds of Tables 1 to 15 exhibit good activity in this test.

C. Acarcidal action

Example B11: Action against *Tetranychus urticae*

Young bean plants are populated with a mixed population of *Tetranychus urticae* and sprayed one day later with an aqueous emulsion spray mixture comprising 100 ppm of the test compound. The plants are then incubated for 6 days at 25° C. and subsequently evaluated. The percentage reduction in population (% activity) is determined by comparing the number of dead eggs, larvae and adults on the treated plants with that on untreated plants. The compounds of Tables 1 to 15 generally exhibit good activity in this test. In particular, compounds 1-4.2, 2-4.2, 3-4.2, 4-1.1, 5.5, 6.3, 8.10, 9-2.2, 12-1.3, 10-1.16 and 12-1.4 are more than 80% effective in this test

What is claimed is:

1. A compound of formula

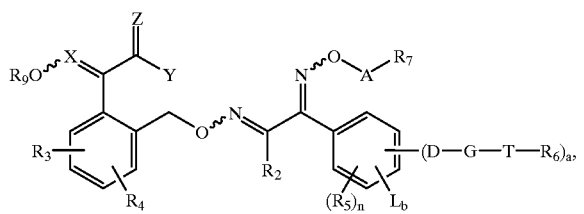

(I)

wherein either X is CH or N, Y is $OR_1$ and Z is O, or
X is N, Y is $NHR_8$ and Z is O, S or S(=O);

$R_1$ is hydrogen or $C_1$–$C_4$alkyl;

$R_8$ is hydrogen or $C_1$–$C_4$alkyl;

$R_2$ is H, $C_1$–$C_4$alkyl, halo-$C_1$–$C_4$alkyl, $C_6$cycloalkyl, $C_1$–$C_4$alkoxymethyl, $C_1$–$C_4$alkoxy, halo-$C_1$–$C_4$alkoxy, $C_1$–$C_4$alkylthio, halo C-$C_4$alkylthio or CN;

$R_3$ and $R_4$ are each independently of the other H, $C_1$–$C_4$alkyl, $C_1$–$C_4$alkoxy, OH, CN, $NO_2$, a ($C_1$–$C_4$alkyl)$_3$—Si group, the alkyl groups being the same or different, halogen, ($C_1$–$C_4$alkyl)S(=O)$_m$, (halo-$C_1$–$C_4$alkyl)S(=O)$_m$, halo-$C_1$–$C_4$alkyl or halo-$C_1$–$C_4$alkoxy;

m is 0, 1 or 2;

$R_5$ independently of any other is halogen, $C_1$–$C_6$-alkyl, halo-$C_1$–$C_6$alkyl, $C_3$–$C_6$-cycloalkyl, halo-$C_3$–$C_6$cycloalkyl, $C_1$–$C_6$alkoxy, halo-$C_1$–$C_6$alkoxy, $C_1$–$C_6$-alkylthio, halo-$C_1$–$C_6$-alkylthio, $C_1$–$C_6$alkylsulfinyl, halo-$C_1$–$C_6$alkylsulfinyl, $C_1$–$C_6$alkylsulfonyl, halo-$C_1$–$C_6$alkylsulfonyl, $C_1$–$C_6$alkylsulfonyloxy, halo-$C_1$–$C_6$alkylsulfonyloxy, $C_1$–$C_6$alkoxy-$C_1$–$C_6$alkyl, halo-$C_1$–$C_6$alkoxy-$C_1$–$C_6$alkyl, $C_1$–$C_6$alkylthio-$C_1$–$C_6$alkyl, halo-$C_1$–$C_6$alkylthio-$C_1$–$C_6$alkyl, $C_1$–$C_6$alkylsulfinyl-$C_1$–$C_6$alkyl, halo-$C_1$–$C_6$alkylsulfinyl-$C_1$–$C_6$alkyl, $C_1$–$C_6$alkylsulfonyl-$C_1$–$C_6$alkyl, halo-$C_1$–$C_6$alkylsulfonyl-$C_1$–$C_6$alkyl, $C_1$–$C_6$alkylcarbonyl, halo-$C_1$–$C_6$alkylcarbonyl, $C_1$–$C_6$alkoxycarbonyl, halo-$C_1$–$C_6$alkoxycarbonyl, $C_1$–$C_6$alkylaminocarbonyl, $C_1$–$C_4$alkoxyiminomethyl, di($C_1$–$C_6$alkyl)aminocarbonyl, the alkyl groups being the same or different; $C_1$–$C_6$alkylaminothiocarbonyl, di($C_1$–$C_6$alkylaminothiocarbonyl, the alkyl groups being the same or different; $C_1$–$C_6$alkylamino, di($C_1$–$C_6$alkyl)amino, the alkyl groups being the same or different; $NO_2$, CN, $SF_5$, thioamido, thiocyanatomethyl, trimethylsilyl; $C_1$–$C_4$alkylenedioxy or —CH=CH—CH=CH- each of which is unsubstituted or, depending on its substitution possibilities, mono- to tetra-substituted, the substituents of the $C_1$–$C_4$alkylenedioxy or —CH=CH—CH=CH— group being selected from the group consisting of $C_1$–$C_4$alkyl and halogen; aryl-Q, heterocyclyl, aryl-Q—$C_1$–$C_6$alkyl, aryl-Q—$C_2C_6$alkenyl, heterocyclyl-$C_1$–$C_6$alkyl or heterocyclyl-Q—$C_2$–$C_6$alkenyl, or aryl-Q—, heterocyclyl-Q—, aryl-Q—$C_1$–$C_6$alkyl, aryl-$C_2$–$C_6$alkenyl, heterocyclyl ($C_1$–$C_6$alkyl or heterocyclyl-Q—$C_2$–$C_2$alkenyl each of which is, depending on its substitution possibilities, mono- to penta-substituted in the aryl or heterocyclyl ring, the substituents being selected independently of one another from the group consisting of halogen, $C_1$–$C_6$alkyl, halo-$C_1$–$C_6$alkyl, $C_3$–$C_6$cycloalkyl, halo-$C_3$–$C_6$cycloalkyl, $C_1$–$C_6$alkoxy, halo-$C_1$–$C_6$alkoxy, CN, nitro and $C_1$–$C_6$alkoxycarbonyl; and, when n is greater than 1, the radicals $R_5$ are the same or different;

n is 0, 1, 2, 3 or, if either a or b is 0, the n may also be 4;

Q is a direct bond, —CH(OH), —C(=O), —S—, —S(=O) or —S(=O)$_2$;

$R_9$ is methyl, fluoromethyl or difluoromethyl; either

A is a direct bond, $C_1$–$C_{10}$alkylene, —C(=O)—, —C(=S)— or halo-$C_1$–$C_{10}$alkylene and $R_7$ is a radical $R_{10}$; or A is $C_1$–$C_{10}$alkylene, —C(=O)—, —C(=S) or halo-$C_1$–$C_{10}$alkylene and $R_7$ is —CN, $OR_{10}$, $N(R_{10})_2$, the radicals $R_{10}$ being the same or different, —$SR_{10}$, —S(=O)$R_{10}$ or —S(=O)$_2R_{10}$;

$R_{10}$ is H, $C_1$–$C_6$alkyl, $C_2$–$C_8$alkenyl, $C_2C_8$alkynyl or $C_3$–$C_6$cycloalkyl, or $C_1$–$C_6$alkyl, $C_2$–$C_8$alkenyl, $C_2$–$C_8$alkynyl or $C_3$–$C_6$cycloalkyl each mono- or polysubstituted by substituents from the group consisting of halogen; —Si($C_1$–$C_4$alkyl)$_3$, the alkyl groups being the same or different; $C_1$–$C_4$alkoxycarbonyl or an aryl or heterocyclyl group that is unsubstituted or mono- or poly-substituted by substituents selected from the group consisting of halogen, $C_1$–$C_4$alkyl and halo-$C_1$–$C_4$alkyl; and D is O, S, —S(=O) or S(=O)$_2$;

G is —CH(CH$_3$)—;

T—R$_6$ is R$_6$; —C(=N—O—A$_1$—R$_{77}$)R$_8$; —SiR$_{14}$(R$_{15}$)—R$_6$; —C(=O)—R$_6$; —C(R$_{16}$)=C(R$_{17}$)—R$_6$; C≡C—R$_6$ or —D—R$_6$;

R$_6$ is $C_1$–$C_4$alkyl, aryl or heteroaryl; or aryl or heteroaryl each of which is 0, 1, 2, 3, 4 or 5, the substituents R$_5$ being independent of one another when s is greater than 1;

A$_1$ and R$_{77}$ are as defined above for A and R$_7$;

a is 0 or 1;

L is U—R$_{18}$, P(O)$_v$R$_{11}$R$_{12}$, P(S)$_w$R$_{11}$R$_{12}$ or N(aryl)R$_{13}$, the aryl radical being either unsubstituted or mono- to penta-substituted by substituents selected independently of one another from the group consisting of R$_5$;

v and w are 0 or 1;

U—R$_{18}$ is —C(=O)—C(=O)—R$_{18}$; —C(OH)—C(OH)—R$_{18}$; —C(=N—O—A$_1$—R$_7$)—R$_{18}$;

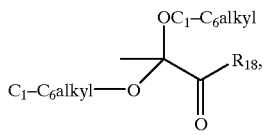

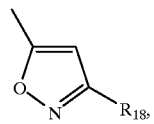

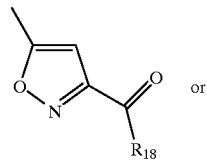

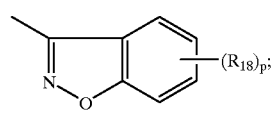

p is from 0 to 4;

R$_{11}$ and R$_{12}$ are each independently of the other $C_1$–$C_6$alkyl, halo-$C_1$–$C_6$alkyl, $C_3$–$C_6$cycloalkyl, halo-$C_3$–$C_6$cycloalkyl, $C_1$–$C_6$alkoxy, halo-$C_1$–$C_6$alkoxy, $C_1$–$C_6$alkylthio, halo-$C_1$–$C_6$alkylthio, aryl, heteroaryl, aryloxy, arylthio, heteroaryloxy or heteroarylthio; or aryl, heteroaryl, aryloxy, arylthio, heteroaryloxy or heteroarylthio each mono- to penta-substituted by R$_5$, the substituents R$_5$ being independent of one another;

b is 0 or 1, but a and b are not simultaneously 0;

R$_{13}$ is hydrogen, $C_1$–$C_6$alkyl, halo-$C_1$–$C_6$alkyl, $C_3$–$C_6$cycloalkyl, halo-$C_3$–$C_6$cycloalkyl, $C_1$–$C_6$alkylsulfinyl, halo-$C_1$–$C_6$alkylsulfinyl, $C_1$–$C_6$alkylsulfonyl, halo-$C_1$–$C_6$alkylsulfonyl, $C_1$–$C_6$alkoxy-$C_1$–$C_6$alkyl, halo-$C_1$–$C_6$alkoxy-$C_1$–$C_6$alkyl, $C_1$–$C_6$alkylthio-$C_1$–$C_6$alkyl, halo-$C_1$–$C_6$alkylthio-$C_1$–$C_6$alkyl, $C_1$–$C_6$alkylsulfinyl-$C_1$–$C_6$alkyl, halo-$C_1$–$C_6$alkylsulfinyl-$C_1$–$C_6$alkyl, $C_1$–$C_6$alkylsulfonyl-$C_1$–$C_6$alkyl, halo-$C_1$–$C_6$alkylsulfonyl-$C_1$–$C_6$alkyl, formyl, $C_1$–$C_6$alkylcarbonyl, $C_1$–$C_6$alkyl-C(=S)—, $C_1$–$C_6$alkylthio-C(=S)—, halo-$C_1$–$C_6$alkylcarbonyl, $C_1$–$C_6$alkoxycarbonyl, halo-$C_1$–$C_6$alkoxycarbonyl, $C_1$–$C_6$alkylaminocarbonyl, $C_1$–$C_4$-alkoxyiminomethyl, di($C_1$–$C_6$alkyl)aminocarbonyl, the alkyl groups being the same or different; $C_1$–$C_6$alkylaminothiocarbonyl, di($C_1$–$C_6$alkyl)aminothiocarbonyl, the alkyl groups being the same or different; $C_1$–$C_6$alkydicarbonyl, halo-$C_1$–$C_6$alkyldicarbonyl, $C_1$–$C_6$alkoxydicarbonyl, halo-$C_1$–$C_6$alkoxydicarbonyl, $C_1$–$C_6$alkylaminodicarbonyl, di($C_1$–$C_6$alkyl)aminodicarbonyl, the alkyl groups being the same or different; $C_1$–$C_6$alkylaminodithiocarbonyl, di($C_1$–$C_6$alkylaminodithiocarbonyl, the alkyl groups being the same or different; aryl, arylsulfinyl, aryl-$C_1$–$C_6$alkylsulfinyl, arylsulfonyl, aryl-$C_1$–$C_6$alkylsulfonyl, aryloxy-$C_1$–$C_6$alkyl, arylthio-$C_1$–$C_6$alkyl, aryl-$C_1$–$C_6$alkylsulfinyl-$C_1$–$C_6$alkyl, aryl-$C_1$–$C_6$alkylsulfonyl-$C_1$–$C_6$alkyl, arylcarbonyl, arylalkylcarbonyl, aryloxycarbonyl, arylalkoxycarbonyl, arylaminocarbonyl, aryloxyiminomethyl, di(aryl)aminocarbonyl, the aryl groups being the same or different arylaminothiocarbonyl, di(aryl)aminothiocarbonyl, the aryl groups being the same or different; aryldicarbonyl, aryl-$C_1$–$C_6$alkyldicarbonyl, aryloxydicarbonyl, aryl-$C_1$–$C_6$alkoxydicarbonyl, arylaminodicarbonyl, di(aryl)aminodicarbonyl, the aryl groups being the same or different; arylaminodithiocarbonyl, di(arylaminodithiocarbonyl, the aryl groups being the same or different; and the aryl groups in the aforementioned substituents being unsubstituted or mono- to penta-substituted by substituents R$_5$, the substituents R$_5$ being independent of one another, unsubstituted or substituted heteroaryl, unsubstituted or substituted heteroarylcarbonyl, unsubstituted or substituted heteroarylsulfinyl, or unsubstituted or substituted heteroarylsulfonyl;

R$_{14}$ and R$_{15}$ are each independently of the other $C_1C_4$-alkyl;

R$_{16}$ and R$_{17}$ are each independently of the other hydrogen, $C_1$–$C_4$alkyl or halogen and R$_{18}$ is R$_6$;

and their possible E/Z isomers, mixtures of E/Z isomers and/or tautomers, in each case in free form or in salt form.

2. The compound according to claim 1 of formula (I) in free form.

3. The compound according to claim 2 of formula (I) wherein X is CH and Z is O.

4. The compound according to claim 2 of formula (I) wherein X is N and Z is O.

5. The compound according to claim 2 of formula (I) wherein Y is O$C_1$–$C_4$alkyl.

6. The compound according to claim 1 of the formula:

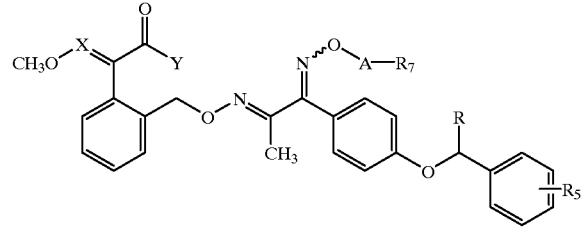

X is N;

Y is methoxy;

AR$^7$ is ethyl;

R is methyl; and

R$^5$ is 4-CF$_3$.

7. The compound according to claim 3 of formula (I) wherein R$_2$ is H, C$_1$–C$_4$alkyl or C$_3$–C$_6$cycloalkyl.

8. The compound according to claim 3 of formula (I) wherein R$_3$ is H, C$_1$–C$_4$alkyl, C$_1$–C$_4$alkoxy, OH, CN, NO$_2$, halogen, halo-C$_1$–C$_4$alkyl or halo-C$_1$–C$_4$alkoxy.

9. The compound according to claim 3 of formula (I) wherein R$_4$ is H, C$_1$–C$_4$alkyl, C$_1$–C$_4$alkoxy, OH, CN, NO$_2$, halogen, halo-C$_1$–C$_4$alkyl or halo-C$_1$–C$_4$alkoxy.

10. The compound according to claim 3 of formula (I) wherein R$_8$ is H or C$_1$–C$_2$alkyl.

11. The compound according to claim 3 of formula (I) wherein R$_9$ is methyl or fluoromethyl.

12. The compound according to claim 3 of formula (I) wherein A is a direct bond, C$_1$–C$_{10}$alkylene or halo C$_1$–C$_{10}$alkylene, and R$_7$ is a radical R$_{10}$.

13. The compound according to claim 12 of formula (I) wherein AR$_7$ is methyl or ethyl.

14. The compound according to claim 3 of formula (I) wherein a is 1, n is 0, b is 0 and D is oxygen.

15. The compound according to claim 14 of formula (I) wherein a is 1 and G is C$_1$–C$_4$alkylene.

16. The compound according to claim 3 of formula (I) wherein R$_6$ is C$_1$–C$_4$alkyl, aryl, or arylmono- to penta-substituted by substituents selected independently of one another from the group consisting of R$_5$.

* * * * *